United States Patent
Sherman et al.

(10) Patent No.: US 8,895,016 B2
(45) Date of Patent: *Nov. 25, 2014

(54) ANTAGONISTS OF ACTIVIN-ACTRIIA AND USES FOR INCREASING RED BLOOD CELL LEVELS

(75) Inventors: Matthew L. Sherman, Newton, MA (US); Jasbir Seehra, Lexington, MA (US); Niels Borgstein, Medfield, MA (US)

(73) Assignee: Acceleron Pharma, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/459,188

(22) Filed: Jun. 26, 2009

(65) Prior Publication Data

US 2010/0028331 A1    Feb. 4, 2010

Related U.S. Application Data

(63) Continuation-in-part of application No. 12/002,872, filed on Dec. 18, 2007.

(60) Provisional application No. 60/875,682, filed on Dec. 18, 2006, provisional application No. 61/133,368, filed on Jun. 26, 2008.

(51) Int. Cl.
| | | |
|---|---|---|
| *A61K 39/00* | (2006.01) | |
| *A61K 38/00* | (2006.01) | |
| *A61K 38/17* | (2006.01) | |
| *C07K 14/71* | (2006.01) | |
| *A61K 38/22* | (2006.01) | |

(52) U.S. Cl.
CPC .............. *C07K 14/71* (2013.01); *C07K 2319/30* (2013.01); *A61K 38/1709* (2013.01); *C07K 2319/31* (2013.01); *A61K 38/00* (2013.01); *A61K 38/22* (2013.01)
USPC ...................... 424/185.1; 514/13.5; 424/192.1

(58) Field of Classification Search
None
See application file for complete search history.

(56) References Cited

U.S. PATENT DOCUMENTS

| | | |
|---|---|---|
| 4,973,577 A | 11/1990 | Vale, Jr. et al. |
| 5,118,667 A | 6/1992 | Adams et al. |
| 5,658,876 A | 8/1997 | Crowley et al. |
| 5,703,043 A | 12/1997 | Celeste et al. |
| 5,760,010 A | 6/1998 | Klein |
| 5,808,007 A | 9/1998 | Lee et al. |
| 5,824,637 A | 10/1998 | Crowley et al. |
| 5,847,078 A | 12/1998 | Eto et al. |
| 5,885,794 A | 3/1999 | Mathews et al. |
| 6,004,780 A | 12/1999 | Soppet et al. |
| 6,093,547 A | 7/2000 | Jin et al. |
| 6,132,988 A | 10/2000 | Sugino et al. |
| 6,162,896 A | 12/2000 | Mathews et al. |
| 6,287,816 B1 | 9/2001 | Rosen et al. |
| 6,451,334 B2 | 9/2002 | Perrine |
| 6,537,966 B1 | 3/2003 | Duan et al. |
| 6,548,634 B1 | 4/2003 | Ballinger et al. |
| 6,599,876 B2 | 7/2003 | Kojima |
| 6,605,699 B1 | 8/2003 | Ni et al. |
| 6,632,180 B1 | 10/2003 | Laragh |
| 6,656,475 B1 | 12/2003 | Lee et al. |
| 6,656,708 B1 | 12/2003 | Yu et al. |
| 6,692,925 B1 | 2/2004 | Miyazono et al. |
| 6,696,260 B1 | 2/2004 | Lee et al. |
| 6,777,205 B1 * | 8/2004 | Carcagno et al. ............ 435/69.1 |
| 6,835,544 B2 | 12/2004 | Mathews et al. |
| 6,891,082 B2 | 5/2005 | Lee et al. |
| 7,192,717 B2 | 3/2007 | Hill et al. |
| 7,202,210 B2 | 4/2007 | Wolfman et al. |
| 7,261,893 B2 | 8/2007 | Veldman et al. |
| 7,320,789 B2 | 1/2008 | Aghajanian et al. |
| 7,560,441 B2 | 7/2009 | Wolfman et al. |
| 7,612,041 B2 | 11/2009 | Knopf et al. |
| 7,709,605 B2 | 5/2010 | Knopf et al. |
| 7,842,663 B2 | 11/2010 | Knopf et al. |
| 7,893,213 B2 | 2/2011 | Mathews et al. |
| 7,919,296 B2 | 4/2011 | Wang |
| 7,988,973 B2 * | 8/2011 | Sherman ..................... 424/185.1 |
| 8,007,809 B2 * | 8/2011 | Sherman ..................... 424/185.1 |
| 8,058,229 B2 | 11/2011 | Seehra et al. |
| 8,138,142 B2 | 3/2012 | Seehra et al. |
| 8,178,488 B2 | 5/2012 | Knopf et al. |
| 8,216,997 B2 | 7/2012 | Seehra et al. |
| 8,252,900 B2 | 8/2012 | Knopf et al. |
| 8,293,881 B2 | 10/2012 | Seehra et al. |
| 8,343,933 B2 | 1/2013 | Knopf et al. |
| 8,388,968 B2 | 3/2013 | Berger et al. |
| 2001/0039036 A1 | 11/2001 | Mathews et al. |

(Continued)

FOREIGN PATENT DOCUMENTS

| | | |
|---|---|---|
| EP | 1174149 A1 | 1/2002 |
| EP | 1 416 273 A1 | 5/2004 |

(Continued)

OTHER PUBLICATIONS

Kuntz. Structure-based strategies for drug design and discovery. Science. 1992 257(5073):1078-1082.*
Miller et al Ligand binding to proteins: the binding landscape model. Protein Sci. Oct. 1997;6(10):2166-79.*
Wang et al. A single amino acid determines lysophospholipid specificity of the S1 P1 (EDG1) and LPA1 (EDG2) phospholipid growth factor receptors. JBC 276:49213-49220, 2001.*
Allendorph, G.P., et al., "Structure of the ternary signaling complex of a TGF-β superfamily member," PNAS, 103(20):7643-7648 (2006).

(Continued)

*Primary Examiner* — Maher Haddad
(74) *Attorney, Agent, or Firm* — Ropes & Gray LLP

(57) ABSTRACT

In certain aspects, the present invention provides compositions and methods for increasing red blood cell and/or hemoglobin levels in vertebrates, including rodents and primates, and particularly in humans.

23 Claims, 17 Drawing Sheets

(56) References Cited

U.S. PATENT DOCUMENTS

| | | | |
|---|---|---|---|
| 2003/0083251 A1 | 5/2003 | Westenfelder | |
| 2003/0144203 A1 | 7/2003 | Bowen | |
| 2004/0033511 A2 | 2/2004 | Pfizenmaier et al. | |
| 2004/0132675 A1 | 7/2004 | Kuo et al. | |
| 2004/0138129 A1* | 7/2004 | MacLeod | 514/12 |
| 2004/0197828 A1 | 10/2004 | Gaddy | |
| 2004/0209805 A1 | 10/2004 | Phillips et al. | |
| 2004/0223966 A1 | 11/2004 | Wolfman et al. | |
| 2005/0106148 A1* | 5/2005 | Kay et al. | 424/145.1 |
| 2005/0197292 A1 | 9/2005 | Smithson et al. | |
| 2005/0244867 A1 | 11/2005 | Soppet et al. | |
| 2005/0257278 A1 | 11/2005 | Lee et al. | |
| 2006/0172347 A1 | 8/2006 | Mellor et al. | |
| 2006/0210657 A1 | 9/2006 | Chou | |
| 2007/0048830 A1 | 3/2007 | Gilbert et al. | |
| 2007/0149455 A1 | 6/2007 | Wolfman et al. | |
| 2007/0172956 A1 | 7/2007 | Magari et al. | |
| 2007/0184052 A1 | 8/2007 | Lin et al. | |
| 2007/0249022 A1 | 10/2007 | Knopf et al. | |
| 2007/0275895 A1 | 11/2007 | Duan et al. | |
| 2007/0292885 A1 | 12/2007 | Bejanin et al. | |
| 2008/0021104 A1 | 1/2008 | Tarallo | |
| 2008/0075692 A1 | 3/2008 | Perrine | |
| 2008/0089897 A1 | 4/2008 | Wolfman | |
| 2008/0102065 A1* | 5/2008 | Borges et al. | 424/130.1 |
| 2008/0139590 A1 | 6/2008 | Qian et al. | |
| 2009/0005308 A1 | 1/2009 | Knopf et al. | |
| 2009/0017019 A1 | 1/2009 | Shields et al. | |
| 2009/0047281 A1 | 2/2009 | Sherman | |
| 2009/0074768 A1 | 3/2009 | Knopf et al. | |
| 2009/0087433 A1 | 4/2009 | Wolfman et al. | |
| 2009/0098113 A1 | 4/2009 | Knopf et al. | |
| 2009/0099086 A1 | 4/2009 | Knopf et al. | |
| 2009/0118188 A1 | 5/2009 | Knopf et al. | |
| 2009/0142333 A1 | 6/2009 | Knopf et al. | |
| 2009/0148436 A1 | 6/2009 | LaVallie et al. | |
| 2009/0163417 A1 | 6/2009 | Sherman | |
| 2010/0008918 A1 | 1/2010 | Sherman et al. | |
| 2010/0015144 A1 | 1/2010 | Sherman et al. | |
| 2010/0028332 A1 | 2/2010 | Sherman et al. | |
| 2010/0068215 A1 | 3/2010 | Seehra et al. | |
| 2010/0183624 A1 | 7/2010 | Seehra et al. | |
| 2010/0272734 A1 | 10/2010 | Berger et al. | |
| 2011/0070233 A1 | 3/2011 | Seehra et al. | |
| 2011/0092670 A1 | 4/2011 | Knopf et al. | |
| 2011/0129469 A1 | 6/2011 | Koncarevic et al. | |
| 2011/0135638 A1 | 6/2011 | Seehra et al. | |
| 2011/0218147 A1 | 9/2011 | Knopf et al. | |
| 2012/0003218 A1 | 1/2012 | Sherman et al. | |
| 2012/0015877 A1 | 1/2012 | Seehra et al. | |
| 2012/0052067 A1 | 3/2012 | Sherman | |
| 2012/0148588 A1 | 6/2012 | Knopf et al. | |
| 2012/0156204 A1 | 6/2012 | Seehra et al. | |
| 2012/0237521 A1 | 9/2012 | Berger et al. | |

FOREIGN PATENT DOCUMENTS

| | | |
|---|---|---|
| EP | 1 362 062 | 5/2005 |
| WO | WO 92/04913 A1 | 4/1992 |
| WO | WO-92/20793 A1 | 11/1992 |
| WO | WO-93/00432 A1 | 1/1993 |
| WO | WO 94/15965 A1 | 7/1994 |
| WO | WO-94/26893 A1 | 11/1994 |
| WO | WO-9510611 A1 | 4/1995 |
| WO | WO-95/29685 A1 | 11/1995 |
| WO | WO 97/23613 A2 | 7/1997 |
| WO | WO-99/06559 A1 | 2/1999 |
| WO | WO 00/18932 A2 | 4/2000 |
| WO | WO-00/43781 A2 | 7/2000 |
| WO | WO-02/10214 A2 | 2/2002 |
| WO | WO-02/40501 A2 | 5/2002 |
| WO | WO-02/43759 A2 | 6/2002 |
| WO | WO-02/085306 A2 | 10/2002 |
| WO | WO 02/094852 A2 | 11/2002 |
| WO | WO-03/006057 A1 | 1/2003 |
| WO | WO-03/053219 A2 | 7/2003 |
| WO | WO-03/072808 A1 | 9/2003 |
| WO | WO-2004/016639 | 2/2004 |
| WO | WO-2004/039948 A1 | 5/2004 |
| WO | WO-2004/108157 A2 | 12/2004 |
| WO | WO 2005/003158 A2 | 1/2005 |
| WO | WO-2005/009460 A2 | 2/2005 |
| WO | WO 2005/014650 A2 | 2/2005 |
| WO | WO-2005/028517 A2 | 3/2005 |
| WO | WO-2005/053795 | 6/2005 |
| WO | WO 2005/070967 A2 | 8/2005 |
| WO | WO-2005/094871 A2 | 10/2005 |
| WO | WO-2005/097825 A2 | 10/2005 |
| WO | WO-2005/113590 A2 | 12/2005 |
| WO | WO-2006002387 A2 | 1/2006 |
| WO | WO-2006/012627 A2 | 2/2006 |
| WO | WO-2006/020844 A2 | 2/2006 |
| WO | WO 2006/020884 A2 | 2/2006 |
| WO | WO-2006/039400 A2 | 4/2006 |
| WO | WO-2006/083183 A1 | 8/2006 |
| WO | WO-2006/088972 A2 | 8/2006 |
| WO | WO 2007/038703 A2 | 4/2007 |
| WO | WO-2007/053775 A1 | 5/2007 |
| WO | WO-2007/062188 | 5/2007 |
| WO | WO-2007/067616 A2 | 6/2007 |
| WO | WO-2007/076127 | 7/2007 |
| WO | WO-2008/015383 A2 | 2/2008 |
| WO | WO-2008/031061 | 3/2008 |
| WO | WO-2008060139 | 5/2008 |
| WO | WO 2008/072723 A1 | 6/2008 |
| WO | WO-2008/073292 A2 | 6/2008 |
| WO | WO-2008/076437 | 6/2008 |
| WO | WO 2008/094708 A2 | 8/2008 |
| WO | WO-2008/097541 | 8/2008 |
| WO | WO-2008/100384 | 8/2008 |
| WO | WO-2008/109167 A2 | 9/2008 |
| WO | WO 2008/151078 A1 | 12/2008 |
| WO | WO-2009/009059 | 1/2009 |
| WO | WO 2009/025651 A1 | 2/2009 |
| WO | WO-2009019504 A1 | 2/2009 |
| WO | WO-2009019505 A2 | 2/2009 |
| WO | WO-2009/070243 | 6/2009 |
| WO | WO 2009/137075 A1 | 11/2009 |
| WO | WO-2009137613 A2 | 11/2009 |
| WO | WO-2009/158015 | 12/2009 |
| WO | WO-2009/158025 | 12/2009 |
| WO | WO-2009/158033 A2 | 12/2009 |
| WO | WO-2010/019261 | 2/2010 |
| WO | WO-2010/083034 | 7/2010 |
| WO | WO-2010/125003 A1 | 11/2010 |
| WO | WO-2010/144452 | 12/2010 |
| WO | WO-2010/151426 | 12/2010 |
| WO | WO-2011020045 A1 | 2/2011 |
| WO | WO-2011/031901 A1 | 3/2011 |

OTHER PUBLICATIONS

Berenson, J.R., "Multiple Myeloma," Multiple Myeloma: Plasma Cell Disorders: Merck Manual Professional (2008). Downloaded from the internet on Sep. 17, 2010. <http://www.merk.com/mmpe/print/sec11/ch144/ch144e.html> pp. 1-5.

Colman, P.M., et al., "Effects of amino acid sequence changes on antibody-antigen interactions," Research of Immunology, 145(1):33-36 (1994).

Greenspan, N.S., et al., "Defining epitopes: It's not as easy as it seems," Nature Biotechnology, 17:936-937 (1999).

Greenwald, J., et al., "Three-finger toxin fold for the extracellular ligand-binding domain of the type II activin receptor serine kinase," Nature Structural Biology, 6(1):18-22 (1999).

Herbert, W.J., et al., The Dictionary of Immunology, Academic Press, 3rd Edition, London, pp. 58-59 (1985).

Hsieh, Matthew M, et al., "HIF-prolyl hydroxylase inhibition results in endogenous erythropoietin induction, erythrocytosis, and modest fetal hemoglobin expression in *Rhesus macaques*," Blood, 110(6):2140-2147 (2007).

Merck Manuals Online Medical Library (online). Anemia of Chronic Disease, Jun. 10, 2008. Downloaded from the internet on Jan. 5,

(56) References Cited

OTHER PUBLICATIONS

2010. <http://web.archive.org/web/20080610070226/http://www.merck.com/mmpe/sec11/ch130/ch130d.html> pp. 1-2.
Merck Manuals Online Medical Library (online). Iron Deficiency Anemia, Jun. 10, 2008. Downloaded from the internet on Jan. 5, 2010. <http://web.archive.org/web/20080610070221/http://www.merck.com/mmpe/sec11/ch130/ch130d.html> pp. 1-4.
Rosenzweig et al., "Cloning and characterization of a human type II receptor for bone morphogenetic proteins," PNAS, 92:7632-7636 (1995).
Ukkola, et al., "Adiponectin: A Link Between Excess Adiposity and Associated Comorbidities?", Journal of Molecular Medicine, 80(11):696-702 (2002).
Walsh, F. S, et al., "Myostatin: a modulator of skeletal-muscle stems cells," Biochemical Society Transactions, 33(Pt.6):1513-1517 (2005).
Acceleron Pharma Presents Positive Phase 1 Results Demonstrating ACE-011 Increases Markers of Bone Formation, Acceleron Pharma, pp. 1-2, retrieved from the Internet, www.acceleronpharma.com/contents/news/press-releases/detail.jsp/q/news-id/47> (2007).
Akel, S., et al, "Neutralization of Autocrine Transforming Growth Factor-β," Stem Cells, 21:557-567 (2003).
Broxmeyer, H.E., et al, "Selective and indirect modulation of human multipotential and erythroid hematopoietic progenitor cell proliferation by recombinant human activin and inhibin," Proc. Natl. Acad. Sci. USA, 85:9052-9056 (1988).
Burdette et al., "Activin A mediates growth inhibition and cell cycle arest through Smads in human breast cancer cells." Cancer Research, 65(17):7968-7975; Abstract (2005).
Centrella et al., "Activin-A Binding and Biochemical Effects in Osteoblast-Enriched Cultures from Fetal-Rat Parietal Bone," Molecular and Cellular Biology, 11(1):250-58 (1991).
Coerver, K.A., et al., "Activin Signaling through Activin Receptor Type II Causes the Cachexia-Like Symptoms in Inhibin-Deficient Mice," Molecular Endocrinology, 10(5):534-543 (1996).
Daluiski et al., "Bone Morphogenetic Protein-3 is a Negative Regulator of Bone Density," Nature Genetics, 27:84-88 (2001).
del Re et al., "Reconstitution and Analysis of Soluble Inhibin and Activin Receptor Complexes in a Cell-free System," The Journal of Biological Chemistry, 279(51):53126-53135 (2004).
Donaldson, et al., "Activin and inhibin binding to the soluble extracellular domain of activin receptor II", Endocrinology 140(4):1760-1766(1999).
Donaldson, et al., "Molecular Cloning and Binding Properties of the Human Type II Activin Receptor", Biochemical and Biophysical Research Communications, 184(1):310-316(1992).
Fafioffe, et al.,"Activin and inhibin receptor gene expression in the ewe pituitary throughout the oestrous cycle," Journal of Endocrinology, vol. 182, pp. 55-68 (2004).
Frigon, N.L., et al, "Regulation of Globin Gene Expression in Human K562 Cells by Recombinant Activin A," Blood, 79(3):765-772 (1992).
Fuller et al., "Activin A Is an Essential Cofactor for Osteoclast Induction," Biochemical and Biophysical Research Communications, 268:2-7 (2000).
Funaba et al., "Expression and Localization of Activin Receptors During Endochondral Bone Development," European Journal of Endocrinology, 144:63-71 (2001).
Gaddy-Kurten et al., "Inhibin Suppresses and Activin Stimulates Osteoblastogenesis and Osteoclastogenesis in Murine Bone Marrow Cultures," Endocrinology, 143(1):74-83 (2002).
Gamer et al., "BMP-3 is a Novel Inhibitor of Both Activin and BMP-4 Signaling in Xenopus Embryos," Developmental Biology, 285:156-168 (2005).
Ge, G., et al., "GDF11 Forms a Bone Morphogenetic Protein 1—Activated Latent Complex That Can Modulate Nerve Growth Factor-Induced Differentiation of PC12 Cells", Molecular and Cellular Biology, 25(14):5846-5858 (2005).

GenBank NM_001106, *Homo sapiens* activin A receptor, type IIB (ACVR2B), mRNA, http://www.ncbi.nlm.nih.gov/entrez/viewer.fcgi?db=nucleotide&val=116734707 (Downloaded on Jan. 29, 2007).
Gonzalez-Cadavid, N.F., et al., "Organization of the human myostatin gene and expression in healthy men and HIV-infected men with muscle wasting," PNAS, 95:14938-14943 (1998).
Gray, et al., "Identification of a binding site on the type II activin receptor for activin and inhibin", Journal of Biological Chemistry, 275(5):3206-3212(2000).
Greenwald, et al., "The BMP7/ActRII Extracellular Domain Complex Provides New Insights into the Cooperative Nature of Receptor Assembly," Molecular Cell, vol. 11, 605-617 (2003).
Hamrick et al., "Bone Mineral Content and Density in the Humerus of Adult Myostatin-Deficient Mice," Calcified Tissue International, 71:63-68 (2002).
Hamrick, "Increased Bone Mineral Density in the Femora of GDF8 Knockout Mice," The Anatomical Record, Part A 272A:388-391 (2003).
Hamrick, M.W., et al., "Femoral Morphology and Cross-sectional Geometry of Adult Myostatin-deficient Mice," Bone, 27(3):343-349 (2000).
Harrison, et al., "Antagonists of activin signaling: mechanisms and potential biological applications," Trends in Endocrinology and Metabolism, 16(2):73-78 (2005).
Hashimoto et al., "Functional Regulation of Osteoblastic Cells by the Interaction of Activin-A with Follistatin," The Journal of Biological Chemistry, 267(7):4999-5004 (1992).
Hemmati-Brivanlou, A., et al., "A truncated activin receptor inhibits mesoderm induction and formation of axial structures in Xenopus embryos," Nature, 359:609-614 (1992).
Hilden, K., et al., "Expression of Type II Activin Receptor Genes During Differentiation of Human K562 Cells and cDNA Cloning of the Human Type IIB Activin Receptor," Blood, 83(8):2163-2170 (1994).
Hill, J.J., et al., "Regulation of Myostatin in Vivo by Growth and Differentiation Factor-Associated Serum Protein-1: A Novel Protein with Protease Inhibitor and Follistatin Domains," Molecular Endocrinology, 17(6):1144-1154 (2003).
Ikenoue et al., "Inhibitory Effects of Activin-A on Osteoblast Differentiation During Cultures of Fetal Rat Calvarial Cells," Journal of Cellular Biochemistry, 75:206-214 (1999).
Kaspar, B.K., et al., "Retrograde Viral Delivery of IGF-1 Prolongs Survival in a Mouse ALS Model," Science, 301:839-842 (2003).
Knight, "Roles of Inhibins, Activins, and Follistatin in the Female Reproductive System," Frontiers in Neuroendocrinology, 17:476-509 (1996).
Kosaki, R., et al., "Left-Right Axis Malformations Associated With Mutations in ACVR2B, the Gene for Human Activin Receptor Type IIB," American Journal of Medical Genetics, 82:70-76 (1999).
Koseki, et al., "Role of TCF-b Family in Osteoclastogenesis Induced by RANKL," Cellular Signaling, 14:31-36 (2002).
Krystal et al., "Transforming Growth Factor β1 Is an Inducer of Erythroid Differentiation," J. Exp. Med., 180:851-860 (1994).
Kubanek, B., "Introduction: The Role of the Microenvironment and Cytokines on the Modulation of Erythropoiesis," Annals New York Academy of Sciences, pp. 257-258 (1994).
Lazar, E., et al., "Transforming Growth Factor α: Mutation of Aspartic Acid 47 and Leucine 48 Results in Different Biological Activities," Molecular and Cellular Biology, 8(3):1247-1252 (1988).
Lebrun, J.J., et al, "Activin and Inhibin Have Antagonistic Effects on Ligand-Dependent Heteromerization of the Type I and Type II Activin Receptors and Human Erythroid Differentiation," Molecular and Cellular Biology, 17(3):1682-1691 (1997).
Lee et al., "Regulation of Muscle Growth by Multiple Ligands Signaling Through Activin Type II Receptors," PNAS 102(50):18117-18122 (2005).
Lee, et al., "Regulation of Myostatin Activity and Muscle Growth," PNAS, 98(16):9306-9311 (2001).
Leto et al., "Activin A Circulating Levels in Patients with Bone Metastasis from Breast or Prostate Cancer," Clin Exp Metastasis, 23(2):117-122 (2006).

(56) References Cited

OTHER PUBLICATIONS

Li, Q., et al., "Prevention of cachexia-like syndrome development and reduction of tumor progression in inhibin-deficient mice following administration of a chimeric activin receptor type II-murine Fc protein," Molecular Human Reproduction, 13(9):675-683 (2007).
Maguer-Satta, V., et al, "Regulation of human erythropoiesis by activin A, BMP2, and BMP4, members of the TGFβ family," Experimental Cell Research, 282:110-120 (2003).
Matzuk et al., "Different phenotypes for mice deficient in either activins or activin receptor type II," Nature, 374:356-360 (1995).
McNally, E.M., "Powerful Genes—Myostatin Regulation of Human Muscle Mass," N. Engl. J. Med., 350(26):2642-2644 (2004).
McPherron, A.C., et al., "Regulation of Skeletal Muscle Mass in Mice by a Bew TGF-b Superfamily Member," Nature, 387:83-90 (1997).
Meriggiola et al., "Follistatin Decreases Activin-Stimulated FSH Secretion with No Effect on GnRH-Stimulated FSH Secretion in Prepubertal Male Monkeys," Endocrinology, 134(4):1967-1970 (1994).
Murase et al., "Possible Involvement of Protein Kinases and Smad2 Signaling Pathways on Osteoclast Differentiation Enhanced by Activin A," Journal of Cellular Physiology, 188:236-242 (2001).
Nagamine et al., "Immunohistochemical Detection of Activin A, Follistatin, and Activin Receptors during Fracture Healing in the Rat," Journal of Orthopaedic Research, 16:314-321 (1998).
Nakamura, K., et al, "Effect of Erythroid Differentiation Factor on Maintenance of Human Hematopoietic Cells in Co-cultures with Allogenic Stromal Cells," Biochemical and Biophysical Research Communications, 194(3):1103-1110 (1993).
Ngo, J.T., et al., Computational Complexity, Protein Structure Prediction, and the Levinthal Paradox, The Protein Folding Problem and Tertiary Structure Prediction, Merz et al., eds., Birkhauser, Boston, pp. 492-495 (1994).
Ogawa et al., "Bovine Bone Activin Enhances Bone Morphogenetic Protein-Induced Ectopic Bone Formation," The Journal of Biological Chemistry, 267(20):14233-14237 (1992).
Oh, S.P., et al., "Activin type IIA and IIB receptors mediate Gdf11 signaling in axial vertebral patterning," Genes & Development, 16:2749-2754 (2002).
Oue et al., "Effect of Local Injection of Activin A on Bone Formation in Newborn Rats," Bone, 15(3):361-366 (1994).
Pearsall, et al., "A Soluble Activin Receptor Type IIA (ACTRIIA) Acts As a Novel Bone Anabolic Agent," The Official Journal of the European Calcified Tissue Society, 34th Europena Symposium on Calcified Tissues, May (2007).
Pearsall, et al., "Treatment with a Soluble Activin Type II Receptor Reverses Bone Loss in Ovariectomized Mice," Journal of Bone and Mineral Research 2006 Abstracts, 21(1):s1-s530 (2006).
Rebbapragada, et al., "Myostatin Signals Through a Transforming Growth Fact b-Like Signaling Pathway to Block Adipogenesis," Molecular and Cellular Biology, 23(20):7230-7242 (2003).
"Recombinant Human Activin RIIA/Fc Chimera", R&D Systems 340-R2 (2003).
"Recombinant Human Activin RIIB/Fc Chimera," R&D Systems 339-RB/CF (2003).
Ruzek et al., "Minimal Effects on Immune Parameters Following Chronic Anti-TGF-β Monoclonal Antibody Administration to Normal Mice," Immunopharmacology and Immunotoxicology 25(2):235-257 (2003).
Sakai et al., "Activin Enhances Osteoclast-Like Cell Formation in Vitro," Biochemical and Biophysical Research Communications, 195(1):39-46 (1993).
Sakai et al., "Activin Increases Bone Mass and Mechanical Strength of Lumbar Vertebrae in Aged Ovariectomized Rats," Bone, 27(1):91-96 (2000).
Sakai et al., "Activin release from bone coupled to bone resorption in organ culture of neonatal mouse calvaria," Bone, 26(3):235-240 (2000).
Sakai et al., "Involvement of Activin in the Regulation of Bone Metabolism," Molecular and Cellular Endocrinology, 180:183-188 (2001).
Sakai et al., "Local Administration of Activin Promotes Fracture Healing in the Rat Fibula Fracture Model," Bone, 25(2):191-196 (1999).
Sakai et al., "The Measurement of Activin/EDF in Mouse Serum: Evidence for Extragonadal Production," Biochemical and Biophysical Research Communications, 188(2):921-926 (1992).
Sakai, et al., "Osteogenic Activity of Activin in Young Normal Rats and Young Adult and Aged Rats after Ovarlectomy," Bone, 23:(Suppl.) 467 (1998).
Schuelke, M., et al., "Myostatin Mutation Associated with Gross Muscle Hypertrophy in a Child," New England Journal of Medicine, 350(26):2682-2688 (2004).
Shao, L., et al., "Effect of Activin A on Globin Gene Expression in Purified Human Erythroid Progenitors," Blood, 79(3):773-781 (1992).
Shav-Tal, Y., et al., "The Role of Activin A in Regulation of Hemopoiesis," Stem Cells, 20:493-500 (2002).
Shiozaki, M., et al, "Activin A: A Commitment Factor in Erythroid Differentiation," Biochemical and Biophysical Research Communications, 242:631-635 (1998).
Shiozaki, M., et al, "Evidence for the participation of endogenous activin A/erythroid differentiation factor in the regulation of erythropoiesis," Proc. Natl. Acad. Sci. USA, 89:1553-1556 (1992).
Shiozaki, M., et al., "In Vivo Treatment With Erythroid Differentiation Factor (EDF / Activin A) Increases Erythroid Precursors (CFU-E and BFU-E) in Mice," Biochemical and Biophysical Research Communications, 165(3):1155-1161 (1989).
Shuto et al., "Osteoblasts Express Types I and II Activin Receptors During Early Intramembranous and Endochondral Bone Formation," Journal of Bone Mineral Research, 12(3):403-411 (1997).
Song, J., et al., "The Type II Activin Receptors Are Essential for Egg Cylinder Growth, Gastrulation, and Rostral Head Development in Mice," Development Biology, 213:157-169 (1999).
Springer, et al., "Seventh European Congress on Clinical and Economic Aspects of Osteoporosis and Osteoarthritis," Osteoporosis International, 18(1):S29-S75 (2007).
Sun, et al., "FSH Directly Regulates Bone Mass," Cell, 125:247-260 (2006).
Thompson, et al., "Structures of an ActRIIB: activin A complex reveal a novel binding mode for TGF-beta ligand: receptor interactions", EMBO 22(7):1555-1566(2003).
Tsuchida, et al., "Activin isoforms signal through type I receptor serine/threonine kinase ALK7," Molecular and Cellular Endocrinology, vol. 220, pp. 59-65 (2004).
Weber, et al., A slient H-bond can by mutationally activated for high-affinity interaction of BMP-2 and activin type IIB receptor, BMC Structural Biology, 7:6, 1-20 (2007).
Wells, J.A., "Additivity of Mutational Effects in Proteins," Biochemistry, 29(37):8509-8517 (1990).
Welt, C.K., et al., "Activin: an endocrine or panacrine agent?," European Journal of Endocrinology, 139:469-471 (1998).
Wiater, et al., "Inhibin is an Antagonist of Bone Morphogenetic Protein Signaling," The Journal of Biological Chemistry, 278(10):7934-7941 (2003).
Wolfman, N.M., et al., "Activation of latent myostatin by the BMP-1/tolloid family of metalloproteinases," PNAS, 100(26):15842-15846 (2003).
Yokota, T., et al., "Isolation and characterization of a mouse cDNA clone that expresses mast-cell growth-factor activity in monkey cells," Proc. Natl. Acad. Sci. USA, 81:1070-1074 (1984).
Yu, J., et al., "Importance of FSH-releasing protein and inhibin in erythrodifferentiation," Nature, 330:765-767 (1987).
Yu et al., "Specific roles of activin/inhibin in human erythropoiesis in vitro." Annals New York Academy of Sciences, 20(10):1243-1246 (1991).
Cirillo et al., Hematocrit, blood pressure, and hypertension. The Gubbio Population Study. Hypertension 20(3): 319-326 (1992).
Kim, et al., Type IIa IgG-Fc Fusion Protein, Increases Hemoglobin and Hematocrit Levels in Postmenopausal Healthy Women. Blood, vol. 112, No. 11, pp. 1316 (2008).

(56) References Cited

OTHER PUBLICATIONS

Merck Manuals Online Medical Library (online). Anemia of Chronic Disease. Jun. 10, 2008 <http://web.archive.org/web/20080610070226/http://www.merck.com/mmpe/sec11/ch130/ch130d.html>, p. 1-2 and 6 (2008).
Satoh et al., Hemodynamic changes by recombinant erythropoietin therapy in hemodialyzed patients. Hypertension 15 (3): 262-266 (1990).
Akpan, I., et al., "The effects of a soluble activin type IIB receptor on obesity and insulin sensitivity," International Journal of Obesity, 33(11):1265-1273 (2009).
Banks, G.B., et al., "The Value of Mammalian Models for Duchenne Muscular Dystrophy in Developing Therapeutic Strategies," Current Topics in Developmental Biology, 84:431-453 (2008).
Bodey, B., et al., "Failure of Cancer Vaccines: The Significant Limitations of this Approach to Immunotherapy," Anticancer Research, 20:2665-2676 (2000).
Chamberlain, R.S., et al., "Innovations and strategies for the development of anticancer vaccines," Expert Opinion on Pharmacotherapy, 1(4):603-614 (2000).
Collins, C.D., "Multidisciplinary Symposium: Haematological Malignancies," Cancer Imaging 5:S119-S126 (2005).
Deconinck, N., et al., "Pathophysiology of Duchenne Muscular Dystrophy: Current Hypotheses," Pediatr. Neurol., 36:1-7 (2007).
Gilbert, R., et al., "Prolonged dystrophin expression and functional correction of mdx mouse muscle following gene transfer with a helper-dependent (gutted) adenovirus-encoding murine dystrophin," Human Molecular Genetics, 12(11):1287-1299 (2003).
Gregoriadis, G., et al., "Polysialic acids: potential in drug delivery," FEBS, 315(3):271-276 (1993).
Harrison, C.A., et al., "An Activin Mutant with Disrupted ALK4 Binding Blocks Signaling via Type II Receptors," The Journal of Biological Chemistry, 279(27):28036-28044 (2004).
Kaiser, J., "First Pass at Cancer Genome Reveals Complex Landscape," Science, 313:1370 (2006).
Menstruation: Absent Periods (Amenorrhea), downloaded on Jun. 14, 2010, <about.com/reports/000101_2.htm?p=1> (11 pages).
Mickle, J.E., et al., "Genotype-Phenotype Relationships in Cystic Fibrosis," Med. Clin. North Am., 84(3):597-607 (2000).
Patel, K., et al., "The function of Myostatin and strategies of Myostatin blockade—new hope for therapies aimed at promoting growth of skeletal muscle," Neuromuscular Disorders, 15:117-126 (2005).
Qi, Z., et al., "Blockade of type β transforming growth factor signaling prevents liver fibrosis and dysfunction in the rat," PNAS, 96:2345-2349 (1999).
Raju, T.S., "Glycosylation in the Fc domain of IgG increases resistance to proteolytic cleavage by papain," Biochemical and Biophysical Research Communications, 341:797-803 (2006).
Vallet, S., et al., "Activin A promotes multiple myeloma-induced osteolysis and is a promising target for myeloma bone disease," PNAS, 107(11):5124-5129 (2010).
Zhao, B., et al., "Transgenic expression of myostatin propeptide prevents diet-induced obesity and insulin resistance," Biochemical and Biophysical Research Communications, 337:248-255 (2005).
Krag, T.O.B., et al., "Heregulin ameliorates the dystrophic phenotype in mdx mice," PNAS, 101(38):13856-13860 (2004).
Kunihro, T., et al., "Regulation of Muscle Mass and Hepatic Steatosis by Follistatin-derived Myostatin Inhibitors," Making Muscle in the Embryo and Adult: a joint meeting of Frontiers in Myogenesis and Skeletal Muscle Stem and Satellite Cells, New York, NY, p. 45 (1990).
Miura, P., et al., "Utrophin upregulation for treating Duchenne or Becker muscular dystrophy: how close are we?," Trends in Molecular Medicine, 12(3):122-129 (2006).
Rodriquez, J.E.S., et al., "Enhanced Osteoclastogenesis Causes Osteopenia in Twisted Gastrulation-Deficient Mice Through Increased BMP Signaling," J. Bone Miner. Res., 24:1917-1926 (2009).
Tinsley, J., et al., "Expression of full-length utrophin prevents muscular dystrophy in mdx mice," Nature Medicine, 4(12):1441-1444 (1998).
Tu, P., et al., "Genetic Disruption of Myostatin Reduces the Development of Proatherogenic Dyslipidemia and Atherogenic Lesions in Ldlr Null Mice," Diabetes, 58:1739-1748 (2009).
Wagner, K.R., et al., "A Phase I/II trial of MYO-029 in Adult Subjects with Muscular Dystrophy," Ann. Neurol., 63:561-571 (2008).
Wagner, K.R., et al., "Loss of Myostatin Attenuates Severity of Muscular Dystrophy in mdx Mice," Ann. Neurol., 52:832-836 (2002).
Wagner, K.R., et al., "Muscle regeneration in the prolonged absence of myostatin," PNAS, 102(7):2519-2524 (2005).
Gura, T., "Cancer Models: Systems for Identifying New Drugs Are Often Faulty," Science, 278(5340):1041-1042 (1997).
Benny Klimek, M.E., et al., "Acute inhibition of myostatin-family proteins preserves skeletal muscle in mouse models of cancer cachexia," Biochemical and Biophysical Research Communications, 391:1548-1554 (2010).
Bogdanovich, S., et al., "Functional improvement of dystrophic muscle by myostatin blockade," Nature, 420:418-421 (2002).
Cadena, S.M., et al., "Administration of a Soluble Activin Type IIB Receptor Promotes Skeletal Muscle Growth Independent of Fiber Type," Journal of Applied Physiology, 109:635-642 (2010).
DePaolo, L.V., et al., "Passive Immunoneutralization with a Monoclonal Antibody Reveals a Role for Endogenous Activin-B in Mediating FSH Hypersecretion during Estrus and Following Ovariectomy of Hypophysectomized, Pituitary-Grafted Rats," Endocrinology, 130(3):1741-1743 (1992).
Greenwald et al., "Characterization of the Extracellular Ligand-Binding Domain of the Type II Activin Receptor," Biochemistry, 37(47):16711-16718 (1998).
Murata, T., et al., "Anti-activin A Antibody (IgY) Specifically Neutralizes Various Activin A Activities," Proceedings of the Society for Experimental Biology & Medicine, 211(1):100-107 (1996).
Sako, D., et al., "Characterization of the Ligand Binding Functionality of the Extracellular Domain of Activin Receptor Type IIB," The Journal of Biological Chemistry, 285(27):21037-21048 (2010).
Schmelzer, C.H., et al., "Purification and Characterization of Recombinant Human Activin B," Biochimica et Biophysica Acta, 1039(2):135-141 (1990).
Thompson, T.B., et al., "Beta A versus beta B: is it merely a matter of express?," Molecular and Cellular Endocrinology, 225:9-17 (2004).
Tisdale, M.J., "Cachexia in Cancer Patients," Nat. Rev. Cancer, 2:862-871 (2002).
Abbiotec: ACTR-IIA Antibody: Catalog No. 251303 (http://www.abbiotec.com) Jun. 3, 2010.
Acta Cryst.,"The CCP4 suite: programs for protein crystallography: Collaborative Computational Project, No. 4," D50: 760-763 (1994).
Anonymous "Learning about Thalassemia" <http://www.genome.gov/10001221> Accessed on Internet Jul. 9, 2013. Published Jun. 28, 2010.
Anti-ActRIIA Antibodies: Commercial Monoclonal Antibodies Against Human ActRIIA (2010).
Antibodies for ACVR2A: http://www.genecards.org/cgi-bin/carddisp.pl?gene=Acvr2a (Jun. 8, 2010).
Attie et al., "A Single Ascending-Dose Study of Muscle Regulator Ace-031 in Healthy volunteers," Muscle & Nerve, pp. 1-8 (2012).
Casset et al., "A Peptide mimetic of an anti-CD4 monoclonal antibody by rational design," Biochemical and Biophysical Research Communications, vol. 307:198-205 (2003).
CDR Definitions from Handbook of Therapeutic Antibodies, (2007).
Chardès et al., "Efficient amplification and direct sequencing of mouse variable regions from any immunoglobulin gene family," FEBS Lett. vol. 452(3): 386-394 (1999).
Chavez-Tapia, Norberto-C et al., "Insulin sensitizers in treatment of nonalcoholic fatty liver disease: Systematic review," World Journal of Gastroenterology, vol. 12(48): 7826-7831 (2006).
Chen et al., "Selection and Analysis of an Optimized Anti-VEGF Antibody: Crystal Structure of an Affinity-matured Fab in Complex with Antigen," J. Mol. Biol., vol. 293: 865-881 (1999).
Donald et al., "SDR: a database of predicted specificity-determining residues in proteins," Nucleic Acids Research, vol. 37: D191-D194 (2009).

(56) References Cited

OTHER PUBLICATIONS

Elliot et al., "Enhancement of therapeutic protein in vivo activities through glycoengineering," Nature Biotechnology, vol. 21: 414-421 (2003).
Fan, et al., "Preclinical evaluation of Hematide, a novel erythropoiesis stimulating agent, for the treatment of anemia," Experimental Hematology 34, pp. 1303-1311 (2006).
Foucar, K., Myelodysplastic/ Myeloproliferative Neoplasms, Am J Clin Pathol, vol. 132: 281-289 (2009).
Haidar et al., "Paraspinal extramedullary hematopoiesis in patients with thalassemia intermedia," Eur Spine J., vol. 19: 871-878 (2010).
Harousseau et al., "Multiple Myeloma," American Society of Hematology, pp. 237-256 (2004).
Holm et al., "Functional mapping and single chain construction of the anti-cytokeratin 8 monoclonal antibody TS1," ScienceDirect; Molecular Immunology, vol. 44(6): 1075-1084 (2007).
"The Illustrated Guide to Bone Marrow Diagnosis Second Edition," Ed. By G. Kumar. Originally published 2003.
Ito et al., "Presence of activin signal transduction in normal ovarian cells and epithelial ovarian carcinoma," British Journal of Cancer, vol. 82(8): 1415-1420 (2000).
Koncarevic et al., "A Soluble Activin Receptor Type IIB Prevents the Effects of Angdrogen Deprivation on Body Composition and Bone Health," Endocrinology, vol. 151(9); 4289-4300 (2010).
Kos et al., "Activin type II receptors in embryonic dorsal root ganglion neurons of the chicken," J. Neurobiol., vol. 47(2): 93-108 (2001).
Liu et al., "Characterization of isoforms of activin receptor-interacting protein 2 that augment activin signaling," Journal of Endocrinology, vol. 189: 409-421 (2006).
MacCallum et al., "Antibody-antigen Interactions: Contact Analysis and Binding site Topography," J. Mol. Biol, vol. 262: 732-745 (1996).
Paul, William E., Fundamental Immunology, 3rd edition, Raven Press, New York, 1003: 292-295 (1999).
Pearsall et al., An investigative pharmacology study of a GDF-8 (myostatin) inhibitor, ACE-031, in the common Marmoset (*Callithrix jacchus*), Database Biosis, Biosciences Information Service, Accession No. PREV201200750016; Faseb Journal, vol. 22, Experimental Biology Annual Meeting, San Diego, CA Apr. 5-9, 2008 (Abstract).
Shi et al., "Energy Balance, Myostatin, and GILZ: Factors Regulating Adipocyte Differentiation in Belly and Bone," PPAR Research, pp. 1-12 (2007).
Shoji et al., "Identification and Characterization of a PDZ Protein That Interacts with Activin Type II Receptors," The Journal of Biological Chemistry, vol. 275(8): 5485-5492 (2000).
Suragani et al., "4236 ACE-536, a Modified Type II Activin Receptor Increases Red Blood Cells in Vivo by Promoting Maturation of Late Stage Erythroblasts," 52nd ASH Annual Meeting and Expositions, Orange County Convention Center, Orlando, FL Dec. 4-7, 2010. (abstract).
Swanson et al., "Use of Biosensors to Monitor the Immune Response," Biologics, vol. 109: 71-78 (2000).
Swanson, S. J., "New Technologies for the Detection of Antibodies to Therapeutic Proteins," Immunogenicity of Therapeutics Biological Products, vol. 112: 127-133 (2003).
Thorpe and Swanson, "Current methods for Detecting Antibodies against Erythropoietin and Other Recombinant Proteins," Clinical and Diagnostic Laboratory Immunology, vol. 12(1): 28-39 (2005).
US Biological, Activin Receptor Type IIA (RIIA) A0856-05E www.usbio.net/technicalsheet.php?item=A0856-05E dated Jun. 8, 2010.
Ward, R., "An update on disordered iron metabolism and iron overload," Hematology, vol. 15(5): 311-317 (2010).
Wong et al., "Validation parameters for a novel biosensor assay which simultaneously measures serum concentrations of a humanized monoclonal antibody and detects induced antibodies," Journal of Immunological Methods, vol. 209: 1-15 (1997).

Yamato et al., "Induction of apoptosis in Myeloma Cells with Activin A," Japanese Journal of Clinical Hematology; 37th Annual Meeting, Symposium 3, Apoptosis in Blood Disorders, 37:7, pp. 564-567) (2012). (translated).
Vajdos et al., "Comprehensive Functional Maps of the Antigen-binding Site of an Anti-ErbB2 Antibody Obtained with Shotgun Scanning mutagenesis," J. Mol. Biol., vol. 320(2): 415-428 (2002).
Zatz et al., "Serum creatine-kinase (CK) and pyruvate-kinase (PK) activities in Duchenne (DMD) as compared with Becker (BMD) muscular dystrophy," Journal of the Neurological Sciences, vol. 102: 190-196 (1991).
Zhang et al., Effects of Activin A on the Activities of the Mouse Peritoneal Macrophages, Cellular & Molecular Immunology, vol. 2(1): 63-67 ( 2005).
Binkert, et al., "Cloning, sequence analysis and expression of a cDNA encoding a novel insulin-like growth factor binding protein (IGFBP-2)," The EMBO Journal, 8(9):2497-2502 (1989).
Caricasole, A. A. D., et al., "Human Growth-Differentiation Factor 3 (HGDF3): Developmental Regulation in Human Teratocarcinoma Cell Lines and Expression in Primary Testicular Germ Cell Tumours," Oncogene, 16:95-103 (1998).
Chamow, S.M., and Ashkenazi, A., "Immunoadhesins: Principles and Applications," TIBTECH, 14: 52-60 (1996).
Chapman, B., et al., "Effect of intron A from human cytomegalovirus (Towne) immediate—early gene on heterologous expression in mammalian cells," Nucleic Acids Research, 19(14):3979-3986 (1991).
Delogu, G., Et al., "DNA vaccine combinations expressing either tissue plasminogen activator signal sequence fusion proteins or ubiquitin-conjugated antigens induce sustained protective immunity in a mouse model of pulmonary tuberculosis," Infection and Immunity, 70(1):292-302 (2002).
Gilchrist, A., et al., "Antagonists of the Receptor-G Protein Interface Block Gi-coupled Signal Transduction," Journal of Biological Chemistry, The American Society of Biological Chemists, Inc., 273(24):14912-14919 (1998).
Kumar, T.R., et al., "Regulation of FSHβ and GnRH Receptor Gene Expression in Activin Receptor II Knockout Male Mice," Mol. Cell. Endocrinology, 212(1-2):19-27 (2003).
Lu, S., et al., "Simian Immunodeficiency Virus DNA Vaccine Trial in Macaques," Journal of Virology, 70(6):3978-3991 (1996).
Maguer-Satta, V., et al, "A Novel Role for Fibronectin Type 1 Domain in the Regulation of Human Hematopoietic Cell Adhesiveness Through Binding to Follistatin Domains of FLRG and Follistatin," Experimental Cell Research, Academic Press, 312(4):434-442 (2006).
Maguer-Satta, V., et al., "FLRG, Member of the Follistatin Family, a New Player in Hematopoiesis," Molecular and Cellular Endocrinology, Elsevier Ireland Ltd., 225(1-2):109-118 (2004).
Mathews, L.S., et al., "Expression Cloning of an Activin Receptor, a Predicted Transmembrane Serine Kinase," Cell, 65(6):973-982 (1991).
McPherron, A.C., et al., "GDF-3 and GDF-9: Two New Members of the Transforming Growth Factor-B Superfamily Containing a Novel Pattern of Cysteines," Journal of Endocrinology, 268(5):3444-3449 (1993).
Ruckle et al., "Single-Dose, Randomized, Double-Blind, Placebo-Controlled Study of ACE-011 (ACTRIIA-IgG1) in Postmenopausal Women," Journal of Bone and Mineral Research, vol. 24(4), pp. 744-752 (2009).
Wang, W., et al., "GDF-3 is an adipogenic cytokine under high fat dietary condition," Biochemical and Biophysical Research Communications, 321(4):1024-1031 (2004).
Chen, Y.G., et al. "Regulation of Cell Proliferation, Apoptosis, and Carcinogenesis by Activin," Exp. Biol. Med., 227(2):75-87 (2002).
Deal, C., "Potential New Drug Targets for Osteoporosis," Nature Clinical Practice, 5(1):20-27 (2009).
Eijken, M., "The Activin A-Follistatin System: Potent Regulator of Human Extracellular Matrix Mineralization," The FASEB Journal, 21:2949-2960 (2007).

(56) References Cited

OTHER PUBLICATIONS

Fajardo, R. J., et al., "Treatment with a Soluble Receptor for Activin Improves Bone Mass and Structure in the Axial and Appendicular Skeleton of Female Cynomolgus Macaques (*Macaca fascicularis*)," Bone, 46:64-71 (2010).

Guo, et al., Protein Tolerance to Random Amino Acid Change. Proc. Natl. Acad. Sci. USA, 101(25):9205-9210 (Jun. 22, 2004). Epub Jun. 14, 2004.

Gupta, V. et al., "Transforming Growth Factor-b Superfamily: Evaluation as Breast Cancer Biomarkers and Preventive Agents," Current Cancer Drug Targets, 4:165-182 (2004).

Krneta, J., et al., "Dissociation of Angiogenesis and Tumorigenesis in Follistatin- and Activin-Expressing Tumors," Cancer Research, 66(11):5686-5695 (2006).

Lotinun, S., et al., "A Soluble Activin Receptor Type IIA Fusion Protein (ACE-011) Increases Bone Mass Via a Dual Anabolic-Antiresorptive Effect in Cynomolgus Monkeys," Bone, 46:1082-1088 (2010).

Ludlow, H., et al., "Development of a new antibody to the human inhibin/activin βB subunit and its application to improved inhibin B ELISAs," J. Immunol. Methods, 329:102-111 (2008).

McPherson, S.J., et al., "Growth inhibitory response to activin A and B by human prostate tumour cell lines LNCaP and DU1465", Journal of Endocrinology, 154:535-545 (1997).

Mosekilde, L., et al., "Emerging Anabolic Treatments in Osteoporosis," Current Drug Safety, 6:62-74 (2011).

Ngo, J.T., et al., "Computational Complexity, Protein Structure Prediction, and the Levinthal Paradox," The Protein Folding Problem and Tertiary Structure Prediction, Merz et al., eds., Birkhauser, Boston, 433 and 492-495 (1994).

Pearsall, R.S., et al., "A soluble activin Type IIA receptor induces bone formation and improves skeletal integrity," PNAS, 105(19):7082-7087 (2008).

Perrien, D. S., et al., "Inhibin A Is an Endocrine Stimulator of Bone Mass and Strength," Endocrinology, 148(4):1654-1665 (2007).

Reis, F.M., et al., "Activin, Inhibin and the Human Breast," Molecular and Cellular Edocrinology, 225:77-82 (2004).

Risbridger, G.P, et al., "Activins and Inhibins in Endocrine and Other Tumors," Endocrine Reviews, 22(6):836-858 (2001).

Robinson, G.W., et al., "Inhibins and Activins Regulate Mammary Epithelial Cell Differentiation Through Mesenchymal-epithelial Interactions," Development, 124:2701-2708 (1997).

Smith, L. et al., "The analysis of doxorubicin resistance in human breast cancer cells using antibody microarrays," Mol. Cancer Therapy, vol. 5: 2115-2120 (2006).

Smith, L. et al., The Status, Quality, and Expansion of the NIH Full-Length cDNA Project: The Mammalian Gene Collection (MGC), Genome Res., vol. 14(10b),: 2127-2127 (2004).

Tanno, T. and Miller, J.L., "Iron Loading and Overloading due to Ineffective Erythropoiesis," Advances in Hematology, Article ID 358283, Chapter 2 (Abstract) (2010).

Trivedi, R., et al., "Investigational Anabolic Therapies for Osteoporosis," Expert Opin. Investig. Drugs, 19(8):995-1005 (2010).

Type 2 Diabetes, PubMed Health, Diseases and Conditions, U.S. National Library of Medicine, Bethesda, MD (online), Jun. 28, 2011 [retrieved on Jun. 6, 2012). Retrieved from the Internet:<URL:http://www.ncbi.nlm.nih.gov/pubmedhealth/PMH0001356/>.

Utzschneider, et al., The Role of Insulin Resistance in Nonalcoholic Fatty Liver Disease, J. Clin. Endocrinol. Metab., 91(12):4753-4761 (Dec. 2006). Epub Sep. 12, 2006.

Anonymous "Iron and Thalassemia," Accessed on the Internet Apr. 3, 2014 at <sickle.bwh.harvard.edu/thaliron.html>. Published Aug. 25, 1997.

Bhatia et al., Protein Glycosylation: Implications for In Vivo Functions and Therapeutic Applications. Advances in Biochemical Engineering/Biotechnology, vol. 64: 155-201 (1998).

Bork, "Powers and Pitfalls in Sequence Analysis: The 70% Hurdle," Genome Research, 10:398-400 (2000).

Chang, Sam S., "Exploring the Effects of Luteinizing Hormone-Releasing Hormone Agonist Therapy on Bone Health: Implications in the Management of Prostate Cancer," Urology, vol. 52: 29-35 (2003).

Database Geneseq [Online], "Variable heavy chain of anti-human Fas ligand antibody NOK-4," retrieved from EBI accession No. GSP:AAW00829; Database accession No. AAW00829; abstract, sequence (1997).

Database Geneseq [Online]; "Monoclonal antibody 10D4 HMGB1 Vkappa domain," retrieved from EBI accession No. GSP:ADY85028, Database accession No. GSP:ADY85028; abstract, sequence (2005).

Fournier et al., "Blockade of the activin receptor IIb activates functional brown adipogenesis and thermogenesis by inducing mitochondrial oxidative metabolism," Mol. Cell. Biol. vol. 32(14): 2871-2879 (2012).

Ma, "Animal Models of Disease," Modern Drug Discovery, 30-36 (2004).

Nemeth, E., "Hepcidin in β-thalassemia," Annals of the New York Academy of Sciences, vol. 1202: 31-35. Published Aug. 2, 2010.

Shao, L., et al., "Efficient synthesis of globoside and isogloboside tetrasaccharides by using beta (1-->3) N-acetylgalactosaminyltransferase/UDP-N-acetyglucosamine C4 epimerase fusion protein," Chem Commun.: 1422-1423 (2003).

Shapiro et al., "Side Effects of Adjuvant Treatment of Breast Cancer," New England Journal of Medicine, vol. 344: 1997-2008 (2001).

Tseng, Yu-Hua et al., "New role of bone morphogenetic protein 7 in brown adipogenesis and energy expenditure," Nature: International Weekly Journal of Science (and Supplementary Information), vol. 454(7207): 1000-1004 (2008).

\* cited by examiner

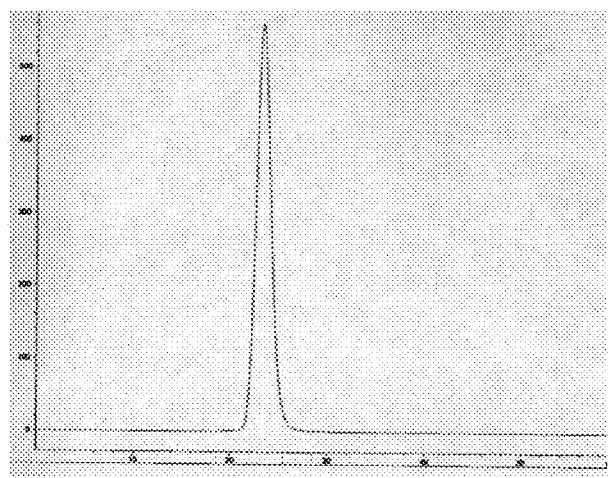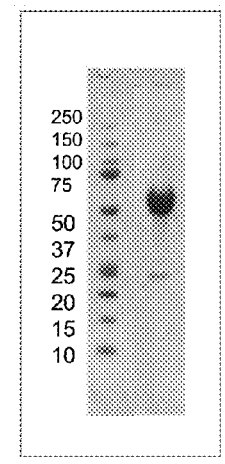
Figure 1A                    Figure 1B

```
ActRIIa     ILGRSETQEC LFFNANWEKD RTNQTGVEPC YGDKDKRRHC FATWKNISGS
ActRIIb     GRGEAETREC IYYNANWELE RTNQSGLERC EGEQDKRLHC YASWRNSSGT

IEIVKQGCWL DDINCYDRTD CVEKKDSPEV YFCCCEGNMC NEKFSYFPEM
            IELVKKGCWL DDFNCYDRQE CVATEENPQV YFCCCEGNFC NERFTHLPEA

EVTQPTSNPV TPKPPT
            GGPEVTYEPP PTAPT
```

FIGURE 14

FIGURE 15. Effect of ActRIIA-mFc on chemotherapy-induced anemia in mice
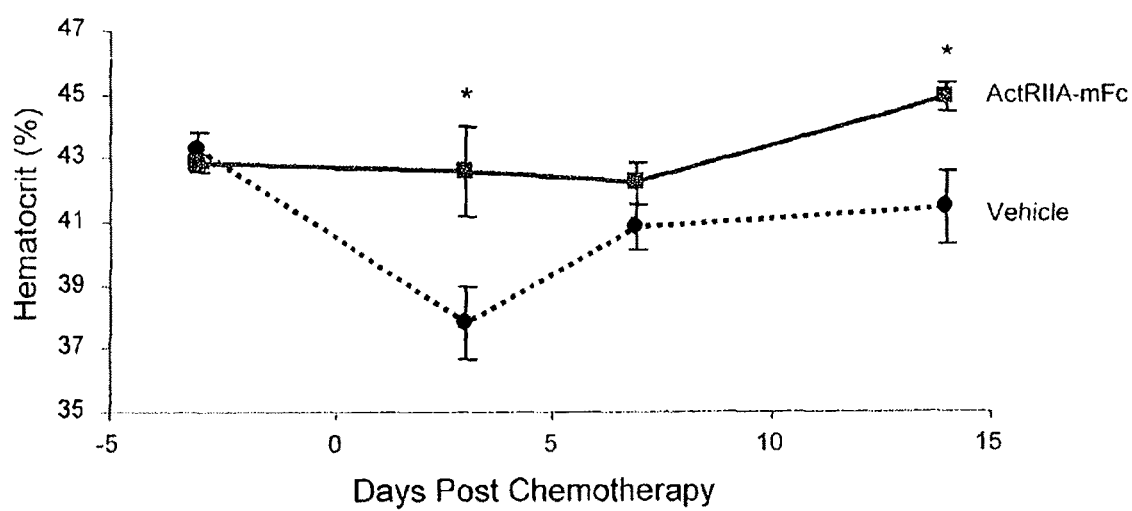

FIGURE 16. Dose-dependent effect of ActRIIA-mFc on chemotherapy-induced anemia in mice
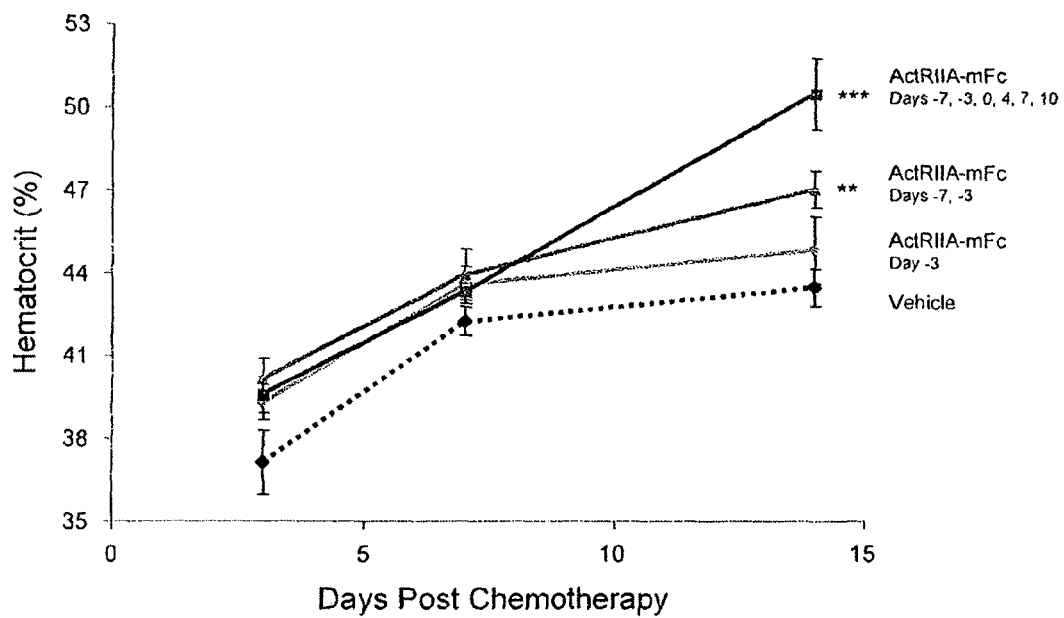

FIGURE 17. Effect of ActRIIA-mFc on anemia in mouse model of chronic kidney disease
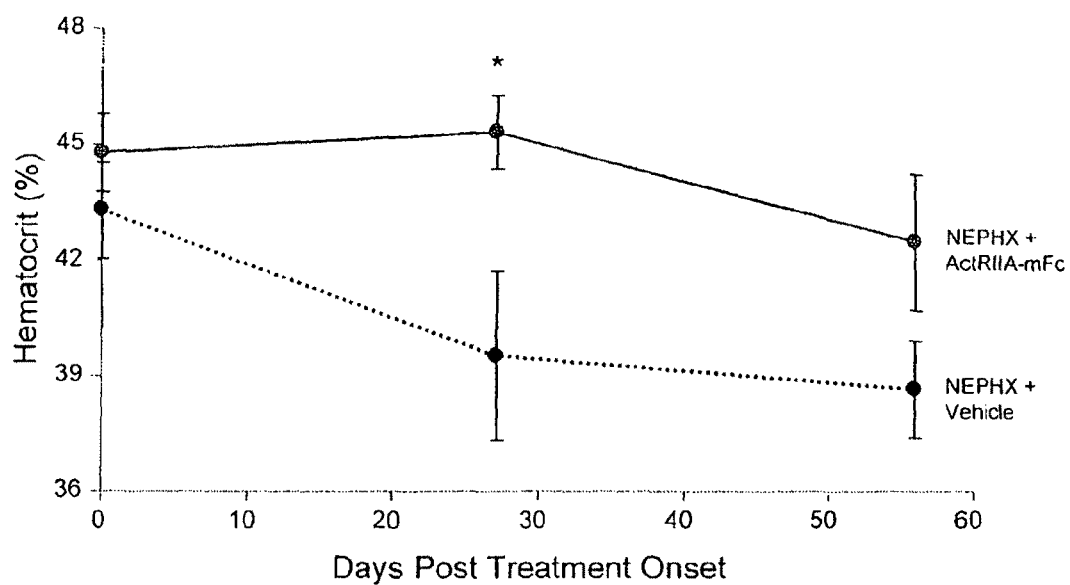

US 8,895,016 B2

ANTAGONISTS OF ACTIVIN-ACTRIIA AND USES FOR INCREASING RED BLOOD CELL LEVELS

RELATED APPLICATIONS

This application is a continuation in part of U.S. Ser. No. 12/002,872 (now U.S. Pat. No. 7,988,973), filed on Dec. 18, 2007, which claims the benefit of U.S. Provisional Application No. 60/875,682, filed on Dec. 18, 2006, the specifications of which are incorporated by reference in their entireties. This application also claims the benefit of U.S. Provisional Application No. 61/133,368, filed on Jun. 26, 2008, the specification of which is incorporated by reference herein in its entirety.

SEQUENCE LISTING

The instant application contains a Sequence Listing which has been submitted via EFS-Web and is hereby incorporated by reference in its entirety. Said ASCII copy, created on Aug. 30, 2011, is named PHPH_038_101_SS.txt, and is 35,646 bytes in size.

BACKGROUND OF THE INVENTION

The mature red blood cell, or erythrocyte, is responsible for oxygen transport in the circulatory systems of vertebrates. Red blood cells carry high concentrations of hemoglobin, a protein that binds oxygen in the lungs at relatively high partial pressure of oxygen ($pO_2$) and delivers oxygen to areas of the body with a relatively low $pO_2$.

Mature red blood cells are produced from pluripotent hematopoietic stem cells in a process termed erythropoiesis. In post-natal individuals, erythropoiesis occurs primarily in the bone marrow and in the red pulp of the spleen. The coordinated action of various signaling pathways control the balance of cell proliferation, differentiation, survival and death. Under normal conditions, red blood cells are produced at a rate that maintains a constant red cell mass in the body, and production may increase or decrease in response to various stimuli, including increased or decreased oxygen tension or tissue demand. The process of erythropoiesis begins with the formation of lineage committed precursor cells and proceeds through a series of distinct precursor cell types. The final stages of erythropoiesis occur as reticulocytes are released into the bloodstream and lose their mitochondria and ribosomes while assuming the morphology of mature red blood cell. An elevated level of reticulocytes, or an elevated reticulocyte:erythrocyte ratio, in the blood is indicative of increased red blood cell production rates.

Erythropoietin (Epo) is widely recognized as the most significant positive regulator of erythropoiesis in post-natal vertebrates. Epo regulates the compensatory erythropoietic response to reduced tissue oxygen tension (hypoxia) and low red blood cell levels or low hemoglobin levels. In humans, elevated Epo levels promote red blood cell formation by stimulating the generation of erythroid progenitors in the bone marrow and spleen. In the mouse, Epo enhances erythropoiesis primarily in the spleen.

Various forms of recombinant Epo are used by physicians to increase red blood cell levels in a variety of clinical settings, and particularly for the treatment of anemia. Anemia is a broadly-defined condition characterized by lower than normal levels of hemoglobin or red blood cells in the blood. In some instances, anemia is caused by a primary disorder in the production or survival of red blood cells. More commonly, anemia is secondary to diseases of other systems (Weatherall & Provan (2000) Lancet 355, 1169-1175). Anemia may result from a reduced rate of production or increased rate of destruction of red blood cells or by loss of red blood cells due to bleeding. Anemia may result from a variety of disorders that include, for example, chronic renal failure, myelodysplastic syndrome, rheumatoid arthritis, and bone marrow transplantation.

Treatment with Epo typically causes a rise in hemoglobins by about 1-3 g/dL in healthy humans over a period of weeks. When administered to anemic individuals, this treatment regimen often provides substantial increases in hemoglobin and red blood cell levels and leads to improvements in quality of life and prolonged survival. Epo is not uniformly effective, and many individuals are refractory to even high doses (Horl et al. (2000) Nephrol Dial Transplant 15, 43-50). Over 50% of patients with cancer have an inadequate response to Epo, approximately 10% with end-stage renal disease are hyporesponsive (Glaspy et al. (1997) J Clin Oncol 15, 1218-1234; Demetri et al. (1998) J Clin Oncol 16, 3412-3425), and less than 10% with myelodysplastic syndrome respond favorably (Estey (2003) Curr Opin Hematol 10, 60-67). Several factors, including inflammation, iron and vitamin deficiency, inadequate dialysis, aluminum toxicity, and hyperparathyroidism may predict a poor therapeutic response, the molecular mechanisms of resistance to Epo are as yet unclear.

Thus, it is an object of the present disclosure to provide alternative compositions and methods for increasing red blood cell levels in patients.

SUMMARY OF THE INVENTION

In part, the disclosure demonstrates that activin antagonists, as well as ActRIIa antagonists (collectively, "activin-ActRIIa antagonists"), can be used to increase red blood cell and hemoglobin levels. In part, the disclosure demonstrates that activin-ActRIIa antagonists can increase red blood cell and hemoglobin levels and also increase bone density. This dual effect has particular advantages in patients that have both anemia and bone loss, such as many cancer patients (where anemia and bone loss can be a consequence of the tumor or a consequence of irradiation or chemotherapy), patients with osteoporosis and patients with renal failure. In particular, the disclosure demonstrates that a soluble form of ActRIIa acts as an inhibitor of activin and, when administered in vivo, increases red blood cell levels. While soluble ActRIIa may affect red blood cell levels through a mechanism other than activin antagonism, the disclosure nonetheless demonstrates that desirable therapeutic agents may be selected on the basis of activin antagonism or ActRIIa antagonism or both. Such agents are referred to collectively as activin-ActRIIa antagonists. Therefore, in certain embodiments, the disclosure provides methods for using activin-ActRIIa antagonists, including, for example, activin-binding ActRIIa polypeptides, anti-activin antibodies, anti-ActRIIa antibodies, activin- or ActRIIa-targeted small molecules and aptamers, and nucleic acids that decrease expression of activin or ActRIIa, to increase red blood cell and hemoglobin levels in patients and to treat disorders associated with low red blood cell or hemoglobin levels in patients in need thereof, or to have combined effects on bone and red blood cells. As described in U.S. patent application Ser. No. 11/603,485, and in published patent applications WO 2008/100384 and WO/2007/062188, incorporated by reference herein, activin-ActRIIa antagonists can be used to promote bone growth and increase bone density. As described herein, the effects of activin-ActRIIa antagonists on red blood cell levels are more rapid and occur at lower doses than the effects of such antagonists on bone. Thus, in certain embodiments, the disclosure provides methods for using an activin-ActRIIa antagonist to increase red blood cell or hemoglobin levels without causing a significant increase in bone density. For example, a method may cause less than 3%, 5%, 10% or 15% increase in bone density. This selective effect may be achieved by using, for example, lower doses of activin-ActRIIa antagonist, less frequent doses, or by using an activin-ActRIIa antagonist with a shorter serum half-life at doses and frequencies calculated to provide a lower serum concentration. Additionally, given that activin-ActRIIa antagonists promote both bone growth and increases in red blood cell levels, the disclosure provides methods for promoting bone growth and increasing red blood cell levels, particularly in patients with disorders that are characterized by anemia and loss of bone, such as inflammatory bowel diseases, rheumatoid arthritis, multiple myeloma, cancer- and cancer treatment-related bone loss and many forms of renal failure, including end stage renal disease.

In certain aspects, the disclosure provides polypeptides comprising a soluble, activin-binding ActRIIa polypeptide that binds to activin. ActRIIa polypeptides may be formulated as a pharmaceutical preparation comprising the activin-binding ActRIIa polypeptide and a pharmaceutically acceptable carrier. The activin-binding ActRIIa polypeptide may bind to activin with a $K_D$ less than 1 micromolar or less than 100, 10 or 1 nanomolar. Optionally, the activin-binding ActRIIa polypeptide selectively binds activin versus GDF11 and/or GDF8, and optionally with a $K_D$ that is at least 10-fold, 20-fold or 50-fold lower with respect to activin than with respect to GDF11 and/or GDF8. While not wishing to be bound to a particular mechanism of action, it is expected that this degree of selectivity for activin inhibition over GDF11/GDF8 inhibition in ActRIIa-Fc accounts for effects on bone or erythropoiesis without a consistently measurable effect on muscle. In many embodiments, an ActRIIa polypeptide will be selected for causing less than 15%, less than 10% or less than 5% increase in muscle at doses that achieve desirable effects on red blood cell levels. In other embodiments, the effect on muscle is acceptable and need not be selected against. The composition may be at least 95% pure, with respect to other polypeptide components, as assessed by size exclusion chromatography, and optionally, the composition is at least 98% pure. An activin-binding ActRIIa polypeptide for use in such a preparation may be any of those disclosed herein, such as a polypeptide having (i.e. comprising) an amino acid sequence selected from SEQ ID NOs: 2, 3, 7, 12 or 13, or having (i.e. comprising) an amino acid sequence that is at least 80%, 85%, 90%, 95%, 97% or 99% identical to an amino acid sequence selected from SEQ ID NOs: 2, 3, 7, 12 or 13. An activin-binding ActRIIa polypeptide may include a functional fragment of a natural ActRIIa polypeptide, such as one comprising at least 10, 20 or 30 amino acids of a sequence selected from SEQ ID NOs: 1-3 or a sequence of SEQ ID NO: 2, lacking the C-terminal 10 to 15 amino acids (the "tail").

A soluble, activin-binding ActRIIa polypeptide may include one or more alterations in the amino acid sequence (e.g., in the ligand-binding domain) relative to a naturally occurring ActRIIa polypeptide. Examples of altered ActRIIa polypeptides are provided in WO 2006/012627, pp. 59-60 and pp. 55-58, respectively, which is incorporated by reference herein, and throughout U.S. patent application Ser. No. 12/012,652, incorporated by reference herein. The alteration in the amino acid sequence may, for example, alter glycosylation of the polypeptide when produced in a mammalian, insect or other eukaryotic cell or alter proteolytic cleavage of the polypeptide relative to the naturally occurring ActRIIa polypeptide.

An activin-binding ActRIIa polypeptide may be a fusion protein that has, as one domain, an ActRIIa polypeptide, (e.g., a ligand-binding portion of an ActRIIa) and one or more additional domains that provide a desirable property, such as improved pharmacokinetics, easier purification, targeting to particular tissues, etc. For example, a domain of a fusion protein may enhance one or more of in vivo stability, in vivo half life, uptake/administration, tissue localization or distribution, formation of protein complexes, multimerization of the fusion protein, and/or purification. An activin-binding ActRIIa fusion protein may include an immunoglobulin Fc domain (wild-type or mutant) or a serum albumin or other polypeptide portion that provides desirable properties such as improved pharmacokinetics, improved solubility or improved stability. In a preferred embodiment, an ActRIIa-Fc fusion comprises a relatively unstructured linker positioned between the Fc domain and the extracellular ActRIIa domain. This unstructured linker may be an artificial sequence of 1, 2, 3, 4 or 5 amino acids or a length of between 5 and 15, 20, 30, 50 or more amino acids that are relatively free of secondary structure, or a mixture of both. A linker may be rich in glycine and proline residues and may, for example, contain a single sequence of threonine/serine and glycines or repeating sequences of threonine/serine and glycines (e.g., $TG_4$ (SEQ ID NO: 15) or $SG_4$ (SEQ ID NO: 16) singlets or repeats). A fusion protein may include a purification subsequence, such as an epitope tag, a FLAG tag, a polyhistidine sequence, and a GST fusion. Optionally, a soluble ActRIIa polypeptide includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent. A pharmaceutical preparation may also include one or more additional compounds such as a compound that is used to treat a bone disorder or a compound that is used to treat anemia. Preferably, a pharmaceutical preparation is substantially pyrogen free. In general, it is preferable that an ActRIIa protein be expressed in a mammalian cell line that mediates suitably natural glycosylation of the ActRIIa protein so as to diminish the likelihood of an unfavorable immune response in a patient. Human and CHO cell lines have been used successfully, and it is expected that other common mammalian expression systems will be useful.

As described herein, ActRIIa proteins designated ActRIIa-Fc have desirable properties, including selective binding to activin versus GDF8 and/or GDF11, high affinity ligand binding and serum half life greater than two weeks in animal models and in human patients. In certain embodiments the invention provides ActRIIa-Fc polypeptides and pharmaceutical preparations comprising such polypeptides and a pharmaceutically acceptable excipient.

In certain aspects, the disclosure provides nucleic acids encoding a soluble activin-binding ActRIIa polypeptide. An isolated polynucleotide may comprise a coding sequence for a soluble, activin-binding ActRIIa polypeptide, such as described above. For example, an isolated nucleic acid may include a sequence coding for an extracellular domain (e.g., ligand-binding domain) of an ActRIIa and a sequence that would code for part or all of the transmembrane domain and/or the cytoplasmic domain of an ActRIIa, but for a stop codon positioned within the transmembrane domain or the cytoplasmic domain, or positioned between the extracellular domain and the transmembrane domain or cytoplasmic domain. For example, an isolated polynucleotide may comprise a full-length ActRIIa polynucleotide sequence such as SEQ ID NO: 4 or a partially truncated version of ActRIIa, such as a nucleic acid comprising the nucleic acid sequence of SEQ ID NO:5, which corresponds to the extracellular domain of ActRIIa. An isolated polynucleotide may further comprise a transcription termination codon at least six hundred nucleotides before the 3'-terminus or otherwise positioned such that translation of the polynucleotide gives rise to an extracellular domain optionally fused to a truncated portion of a full-length ActRIIa. A preferred nucleic acid sequence for ActRIIa is SEQ ID NO:14. Nucleic acids disclosed herein may be operably linked to a promoter for expression, and the disclosure provides cells transformed with such recombinant polynucleotides. Preferably the cell is a mammalian cell such as a CHO cell.

In certain aspects, the disclosure provides methods for making a soluble, activin-binding ActRIIa polypeptide. Such a method may include expressing any of the nucleic acids (e.g., SEQ ID NO: 4, 5 or 14) disclosed herein in a suitable cell, such as a Chinese hamster ovary (CHO) cell or human cell. Such a method may comprise: a) culturing a cell under conditions suitable for expression of the soluble ActRIIa polypeptide, wherein said cell is transformed with a soluble ActRIIa expression construct; and b) recovering the soluble ActRIIa polypeptide so expressed. Soluble ActRIIa polypeptides may be recovered as crude, partially purified or highly purified fractions. Purification may be achieved by a series of purification steps, including, for example, one, two or three or more of the following, in any order: protein A chromatography, anion exchange chromatography (e.g., Q sepharose), hydrophobic interaction chromatography (e.g., phenylsepharose), size exclusion chromatography, and cation exchange chromatography. Soluble ActRIIa polypeptides may be formulated in liquid or solid (e.g., lyophilized) forms.

In certain aspects, an activin-ActRIIa antagonist disclosed herein may be used in a method for promoting red blood cell production or increasing red blood cell levels in a subject. In certain embodiments, the disclosure provides methods for treating a disorder associated with low red blood cell counts or low hemoglobin levels (e.g., an anemia), or to promote red blood cell production, in patients in need thereof. A method may comprise administering to a subject in need thereof an effective amount of activin-ActRIIa antagonist. In certain embodiments, the disclosure provides methods for increasing red blood cell levels and bone formation in a patient in need thereof. A method may comprise administering to a subject in need thereof an effective amount of activin-ActRIIa antagonist. In certain embodiments the disclosure demonstrates that, in rodents, activin-ActRIIa antagonists increase erythroid precursor cell levels primarily through effects on the spleen. Accordingly, the disclosure provides methods for increasing the release of red blood cells from the spleen, the method comprising administering to the patient an effective amount of an activin-ActRIIa antagonist. In certain aspects, the disclosure provides uses of activin-ActRIIa antagonists for making a medicament for the treatment of a disorder or condition as described herein.

In certain aspects, the disclosure provides a method for identifying an agent that stimulates production of red blood cells. The method comprises: a) identifying a test agent that binds to activin or a ligand-binding domain of an ActRIIa polypeptide; and b) evaluating the effect of the agent on the levels of red blood cells, hemoglobin, and/or red blood cell precursor levels (e.g., reticulocyte levels).

BRIEF DESCRIPTION OF THE DRAWINGS

FIG. 1 shows the purification of ActRIIa-hFc expressed in CHO cells. The protein purifies as a single, well-defined peak as visualized by sizing column (FIG. 1A) and Coomassie stained SDS-PAGE (FIG. 1B) (left lane: molecular weight standards; right lane: ActRIIa-hFc).

FIG. 3 shows the effects of ActRIIa-hFc on red blood cell counts in female non-human primates. Female cynomolgus monkeys (four groups of five monkeys each) were treated with placebo or 1 mg/kg, 10 mg/kg or 30 mg/kg of ActRIIa-hFc on day 0, day 7, day 14 and day 21.

FIG. 4 shows the effects of ActRIIa-hFc on red blood cell counts in male non-human primates. Male cynomolgus monkeys (four groups of five monkeys each) were treated with placebo or 1 mg/kg, 10 mg/kg or 30 mg/kg of ActRIIa-hFc on day 0, day 7, day 14 and day 21.

FIG. 5 shows the effects of ActRIIa-hFc on reticulocyte counts in female non-human primates. Cynomolgus monkeys (four groups of five monkeys each) were treated with placebo or 1 mg/kg, 10 mg/kg or 30 mg/kg of ActRIIa-hFc on day 0, day 7, day 14 and day 21.

FIG. 6 shows the effects of ActRIIa-hFc on reticulocyte counts in female non-human primates. Cynomolgus monkeys (four groups of five monkeys each) were treated with placebo or 1 mg/kg, 10 mg/kg or 30 mg/kg of ActRIIa-hFc on day 0, day 7, day 14 and day 21.

FIG. 14 shows an alignment of human ActRIIA (SEQ ID NO: 23) and ActRIIB (SEQ ID NO: 24) with the residues that are deduced herein, based on composite analysis of multiple ActRIIB and ActRIIA crystal structures to directly contact ligand (the ligand binding pocket) indicated with boxes.

FIG. 15 shows the effect of ActRIIA-mFc on hematocrit in a mouse model of chemotherapy-induced anemia. Data are means±SEM. *, P<0.05 vs. vehicle at same time point. A single dose of ActRIIA-mFc before chemotherapy prevented the decline in hematocrit level otherwise observed after administration of the chemotherapeutic paclitaxel.

FIG. 16 shows the dose-dependent effect of ActRIIA-mFc on hematocrit in a mouse model of chemotherapy-induced anemia. Data are means±SEM. , P<0.01; *, P<0.001 vs. vehicle at same time point. Two weeks after paclitaxel administration, ActRIIA-mFc treatment increased hematocrit level as a function of dose number.

FIG. 17 shows the effect of ActRIIA-mFc on hematocrit in a partially nephrectomized (NEPHX) mouse model of chronic kidney disease. Data are means±SEM. *, P<0.05 vs. vehicle at same time point. ActRIIA-mFc treatment prevented the decline in hematocrit level otherwise observed at 4 weeks and produced a beneficial trend in hematocrit at 8 weeks.

DETAILED DESCRIPTION OF THE INVENTION

1. Overview

Figure 2A:
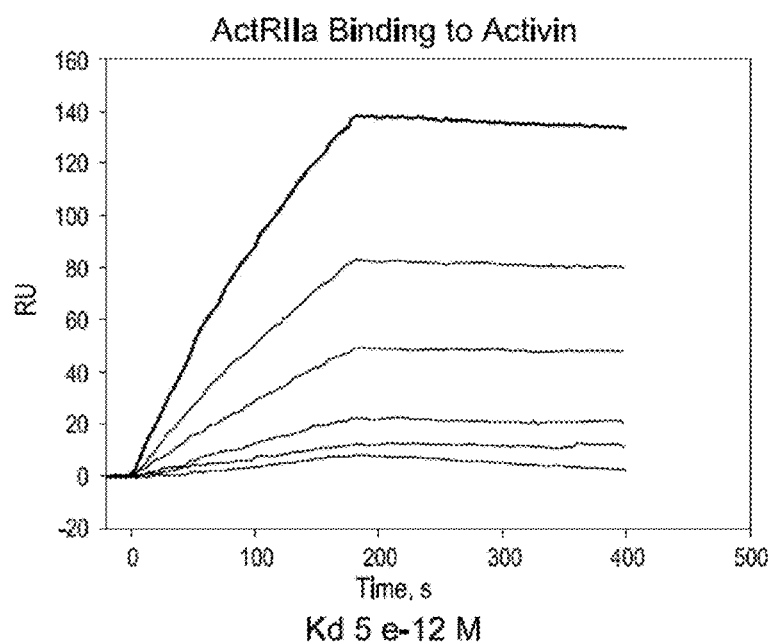
FIG. 2 shows the binding of ActRIIa-hFc to activin (FIG. 2A) and GDF-11 (FIG. 2B), as measured by BiaCore™ assay.

The transforming growth factor-beta (TGF-beta) superfamily contains a variety of growth factors that share common sequence elements and structural motifs. These proteins are known to exert biological effects on a large variety of cell types in both vertebrates and invertebrates. Members of the superfamily perform important functions during embryonic development in pattern formation and tissue specification and can influence a variety of differentiation processes, including adipogenesis, myogenesis, chondrogenesis, cardiogenesis, hematopoiesis, neurogenesis, and epithelial cell differentiation. The family is divided into two general branches: the BMP/GDF and the TGF-beta/Activin/BMP10 branches, whose members have diverse, often complementary effects. By manipulating the activity of a member of the TGF-beta family, it is often possible to cause significant physiological changes in an organism. For example, the Piedmontese and Belgian Blue cattle breeds carry a loss-of-function mutation in the GDF8 (also called myostatin) gene that causes a marked increase in muscle mass. Grobet et al., Nat Genet. 1997, 17(1):71-4. Furthermore, in humans, inactive alleles of GDF8 are associated with increased muscle mass and, reportedly, exceptional strength. Schuelke et al., N Engl J Med 2004, 350:2682-8.

Activins are dimeric polypeptide growth factors that belong to the TGF-beta superfamily. There are three principal activin forms (A, B, and AB) that are homo/heterodimers of two closely related β subunits ($\beta_A\beta_A$, $\beta_B\beta_B$, and $\beta_A\beta_B$, respectively). The human genome also encodes an activin C and an activin E, which are primarily expressed in the liver, and heterodimeric forms containing $\beta_C$ or $\beta_E$ are also known. In the TGF-beta superfamily, activins are unique and multifunctional factors that can stimulate hormone production in ovarian and placental cells, support neuronal cell survival, influence cell-cycle progress positively or negatively depending on cell type, and induce mesodermal differentiation at least in amphibian embryos (DePaolo et al., 1991, Proc Soc Ep Biol Med. 198:500-512; Dyson et al., 1997, Curr Biol. 7:81-84; Woodruff, 1998, Biochem Pharmacol. 55:953-963). Moreover, erythroid differentiation factor (EDF) isolated from the stimulated human monocytic leukemic cells was found to be identical to activin A (Murata et al., 1988, PNAS, 85:2434). It has been suggested that activin A promotes erythropoiesis in the bone marrow. In several tissues, activin signaling is antagonized by its related heterodimer, inhibin. For example, during the release of follicle-stimulating hormone (FSH) from the pituitary, activin promotes FSH secretion and synthesis, while inhibin prevents FSH secretion and synthesis. Other proteins that may regulate activin bioactivity and/or bind to activin include follistatin (FS), follistatin-related protein (FSRP) and $\alpha_2$-macroglobulin.

TGF-β signals are mediated by heteromeric complexes of type I and type II serine/threonine kinase receptors, which phosphorylate and activate downstream Smad proteins upon ligand stimulation (Massagué, 2000, Nat. Rev. Mol. Cell Biol. 1:169-178). These type I and type II receptors are transmembrane proteins, composed of a ligand-binding extracellular domain with cysteine-rich region, a transmembrane domain, and a cytoplasmic domain with predicted serine/threonine specificity. Type I receptors are essential for signaling; and type II receptors are required for binding ligands and for expression of type I receptors. Type I and II activin receptors form a stable complex after ligand binding, resulting in phosphorylation of type I receptors by type II receptors.

Two related type II receptors (ActRII), ActRIIa and ActRIIb, have been identified as the type II receptors for activins (Mathews and Vale, 1991, Cell 65:973-982; Attisano et al., 1992, Cell 68: 97-108). Besides activins, ActRIIa and ActRIIb can biochemically interact with several other TGF-β family proteins, including BMP7, Nodal, GDF8, and GDF11 (Yamashita et al., 1995, J. Cell Biol. 130:217-226; Lee and McPherron, 2001, Proc. Natl. Acad. Sci. 98:9306-9311; Yeo and Whitman, 2001, Mol. Cell 7: 949-957; Oh et al., 2002, Genes Dev. 16:2749-54). ALK4 is the primary type I receptor for activins, particularly for activin A, and ALK-7 may serve as a receptor for activins as well, particularly for activin B.

As demonstrated herein, a soluble ActRIIa polypeptide (sActRIIa), which shows substantial preference in binding to activin A as opposed to other TGF-beta family members, such as GDF8 or GDF11, is effective to increase red blood cell levels in vivo. While not wishing to be bound to any particular mechanism, it is expected that the effect of sActRIIa is caused primarily by an activin antagonist effect, given the very strong activin binding (picomolar dissociation constant) exhibited by the particular sActRIIa construct used in these studies. Regardless of mechanism, it is apparent from this disclosure that ActRIIa-activin antagonists increase red blood cell levels in rodents, monkeys and humans. It should be noted that hematopoiesis is a complex process, regulated by a variety of factors, including erythropoietin, G-CSF and iron homeostasis. The terms "increase red blood cell levels" and "promote red blood cell formation" refer to clinically observable metrics, such as hematocrit, red blood cell counts and hemoglobin measurements, and are intended to be neutral as to the mechanism by which such changes occur.

The data reported herein with respect to non-human primates are reproducible in mice, rats and humans as well, and therefore, this disclosure provides methods for using ActRIIa polypeptides and other activin-ActRIIa antagonists to promote red blood cell production and increase red blood cell levels in mammals ranging from rodents to humans. Activin-ActRIIa antagonists include, for example, activin-binding soluble ActRIIa polypeptides, antibodies that bind to activin (particularly the activin A or B subunits, also referred to as βA or βB) and disrupt ActRIIa binding, antibodies that bind to ActRIIa and disrupt activin binding, non-antibody proteins selected for activin or ActRIIa binding (see e.g., WO/2002/088171, WO/2006/055689, and WO/2002/032925 for examples of such proteins and methods for design and selection of same), randomized peptides selected for activin or ActRIIa binding, often affixed to an Fc domain. Two different proteins (or other moieties) with activin or ActRIIa binding activity, especially activin binders that block the type I (e.g., a soluble type I activin receptor) and type II (e.g., a soluble type II activin receptor) binding sites, respectively, may be linked together to create a bifunctional binding molecule. Nucleic acid aptamers, small molecules and other agents that inhibit the activin-ActRIIa signaling axis are included as activin-ActRIIa antagonists. Various proteins have activin-ActRIIa antagonist activity, including inhibin (i.e., inhibin alpha subunit), although inhibin does not universally antagonize activin in all tissues, follistatin (e.g., follistatin-288 and follistatin-315), FSRP, FLRG, activin C, alpha(2)-macroglobulin, and an M108A (methionine to alanine change at position 108) mutant activin A. Generally, alternative forms of activin, particularly those with alterations in the type I receptor binding domain can bind to type II receptors and fail to form an active ternary complex, thus acting as antagonists. Additionally, nucleic acids, such as antisense molecules, siRNAs or ribozymes that inhibit activin A, B, C or E, or, particularly, ActRIIa expression, can be used as activin-ActRIIa antagonists. The activin-ActRIIa antagonist to be used may exhibit selectivity for inhibiting activin-mediated signaling versus other members of the TGF-beta family, and particularly with respect to GDF8 and GDF11.

The terms used in this specification generally have their ordinary meanings in the art, within the context of this invention and in the specific context where each term is used. Certain terms are discussed below or elsewhere in the specification, to provide additional guidance to the practitioner in describing the compositions and methods of the invention and how to make and use them. The scope or meaning of any use of a term will be apparent from the specific context in which the term is used.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values.

Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

The methods of the invention may include steps of comparing sequences to each other, including wild-type sequence to one or more mutants (sequence variants). Such comparisons typically comprise alignments of polymer sequences, e.g., using sequence alignment programs and/or algorithms that are well known in the art (for example, BLAST, FASTA and MEGALIGN, to name a few). The skilled artisan can readily appreciate that, in such alignments, where a mutation contains a residue insertion or deletion, the sequence alignment will introduce a "gap" (typically represented by a dash, or "A") in the polymer sequence not containing the inserted or deleted residue.

"Homologous," in all its grammatical forms and spelling variations, refers to the relationship between two proteins that possess a "common evolutionary origin," including proteins from superfamilies in the same species of organism, as well as homologous proteins from different species of organism. Such proteins (and their encoding nucleic acids) have sequence homology, as reflected by their sequence similarity, whether in terms of percent identity or by the presence of specific residues or motifs and conserved positions.

The term "sequence similarity," in all its grammatical forms, refers to the degree of identity or correspondence between nucleic acid or amino acid sequences that may or may not share a common evolutionary origin.

However, in common usage and in the instant application, the term "homologous," when modified with an adverb such as "highly," may refer to sequence similarity and may or may not relate to a common evolutionary origin.

2. ActRIIa Polypeptides

In certain aspects, the present invention relates to ActRIIa polypeptides. As used herein, the term "ActRIIa" refers to a family of activin receptor type IIa (ActRIIa) proteins from any species and variants derived from such ActRIIa proteins by mutagenesis or other modification. Reference to ActRIIa herein is understood to be a reference to any one of the currently identified forms. Members of the ActRIIa family are generally transmembrane proteins, composed of a ligand-binding extracellular domain with a cysteine-rich region, a transmembrane domain, and a cytoplasmic domain with predicted serine/threonine kinase activity.

The term "ActRIIa polypeptide" includes polypeptides comprising any naturally occurring polypeptide of an ActRIIa family member as well as any variants thereof (including mutants, fragments, fusions, and peptidomimetic forms) that retain a useful activity. See, for example, WO/2006/012627. For example, ActRIIa polypeptides include polypeptides derived from the sequence of any known ActRIIa having a sequence at least about 80% identical to the sequence of an ActRIIa polypeptide, and optionally at least 85%, 90%, 95%, 97%, 99% or greater identity. For example, an ActRIIa_polypeptide of the invention may bind to and inhibit the function of an ActRIIa protein and/or activin. An ActRIIa polypeptide may be selected for activity in promoting red blood cell formation in vivo. Examples of ActRIIa polypeptides include human ActRIIa precursor polypeptide (SEQ ID NO: 1) and soluble human ActRIIa polypeptides (e.g., SEQ ID NOs: 2, 3, 7 and 12).

The human ActRIIa precursor protein sequence is as follows:

```
                                            (SEQ ID NO: 1)
MGAAAKLAFAVFLISCSSGAILGRSETQECLFFNANWEKDRTNQTGVEPC

YGDKDKRRHCFATWKNISGSIEIVKQGCWLDDINCYDRTDCVEKKDSPEV

YFCCCEGNMCNEKFSYFPEMEVTQPTSNPVTPKPPYYNILLYSLVPLMLI

AGIVICAFWVYRHHKMAYPPVLVPTQDPGPPPPSPLLGLKPLQLLEVKAR

GRFGCVWKAQLLNEYVAVKIFPIQDKQSWQNEYEVYSLPGMKHENILQFI

GAEKRGTSVDVDLWLITAFHEKGSLSDFLKANVVSWNELCHIAETMARGL

AYLHEDIPGLKDGHKPAISHRDIKSKNVLLKNNLTACIADFGLALKFEAG

KSAGDTHGQVGTRRYMAPEVLEGAINFQRDAFLRIDMYANGLVLWELASR

CTAADGPVDEYMLPFEEEIGQHPSLEDMQEVVVHKKKRPVLRDYWQKHAG

MAMLCETIEECWDHDAEARLSAGCVGERITQMQRLTNIITTEDIVTVVTM

VTNVDFPPKESSL
```

The signal peptide is single underlined; the extracellular domain is in bold and the potential N-linked glycosylation sites are double underlined.

The human ActRIIa soluble (extracellular), processed polypeptide sequence is as follows:

(SEQ ID NO: 2)
ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

EVTQPTSNPVTPKPP

The C-terminal "tail" of the extracellular domain is underlined. The sequence with the "tail" deleted (a Δ15 sequence) is as follows:

(SEQ ID NO: 3)
ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

The nucleic acid sequence encoding human ActRIIa precursor protein is as follows (nucleotides 164-1705 of Genbank entry NM_001616):

(SEQ ID NO: 4)
ATGGGAGCTGCTGCAAAGTTGGCGTTTGCCGTCTTTCTTATCTCCTGTTC

TTCAGGTGCTATACTTGGTAGATCAGAAACTCAGGAGTGTCTTTTCTTTA

ATGCTAATTGGGAAAAAGACAGAACCAATCAAACTGGTGTTGAACCGTGT

TATGGTGACAAAGATAAACGGCGGCATTGTTTTGCTACCTGGAAGAATAT

TTCTGGTTCCATTGAAATAGTGAAACAAGGTTGTTGGCTGGATGATATCA

ACTGCTATGACAGGACTGATTGTGTAGAAAAAAAAGACAGCCCTGAAGTA

TATTTTTGTTGCTGTGAGGGCAATATGTGTAATGAAAAGTTTTCTTATTT

TCCAGAGATGGAAGTCACACAGCCCACTTCAAATCCAGTTACACCTAAGC

CACCCTATTACAACATCCTGCTCTATTCCTTGGTGCCACTTATGTTAATT

GCGGGGATTGTCATTTGTGCATTTTGGGTGTACAGGCATCACAAGATGGC

CTACCCTCCTGTACTTGTTCCAACTCAAGACCCAGGACCACCCCCACCTT

CTCCATTACTAGGGTTGAAACCACTGCAGTTATTAGAAGTGAAAGCAAGG

GGAAGATTTGGTTGTGTCTGGAAAGCCCAGTTGCTTAACGAATATGTGGC

TGTCAAAATATTTCCAATACAGGACAAACAGTCATGGCAAAATGAATACG

AAGTCTACAGTTTGCCTGGAATGAAGCATGAGAACATATTACAGTTCATT

GGTGCAGAAAAACGAGGCACCAGTGTTGATGTGGATCTTTGGCTGATCAC

AGCATTTCATGAAAAGGGTTCACTATCAGACTTTCTTAAGGCTAATGTGG

TCTCTTGGAATGAACTGTGTCATATTGCAGAAACCATGGCTAGAGGATTG

GCATATTTACATGAGGATATACCTGGCCTAAAAGATGGCCACAAACCTGC

CATATCTCACAGGGACATCAAAAGTAAAAATGTGCTGTTGAAAAACAACC

TGACAGCTTGCATTGCTGACTTTGGGTTGGCCTTAAAATTTGAGGCTGGC

AAGTCTGCAGGCGATACCCATGGACAGGTTGGTACCCGGAGGTACATGGC

TCCAGAGGTATTAGAGGGTGCTATAAACTTCCAAAGGGATGCATTTTTGA

GGATAGATATGTATGCCATGGGATTAGTCCTATGGGAACTGGCTTCTCGC

TGTACTGCTGCAGATGGACCTGTAGATGAATACATGTTGCCATTTGAGGA

GGAAATTGGCCAGCATCCATCTCTTGAAGACATGCAGGAAGTTGTTGTGC

-continued
ATAAAAAAAGAGGCCTGTTTTAAGAGATTATTGGCAGAAACATGCTGGA

ATGGCAATGCTCTGTGAAACCATTGAAGAATGTTGGGATCACGACGCAGA

AGCCAGGTTATCAGCTGGATGTGTAGGTGAAAGAATTACCCAGATGCAGA

GACTAACAAATATTATTACCACAGAGGACATTGTAACAGTGGTCACAATG

GTGACAAATGTTGACTTTCCTCCCAAAGAATCTAGTCTATGA

The nucleic acid sequence encoding a human ActRIIa soluble (extracellular) polypeptide is as follows:

(SEQ ID NO: 5)
ATACTTGGTAGATCAGAAACTCAGGAGTGTCTTTTCTTTAATGCTAATTG

GGAAAAAGACAGAACCAATCAAACTGGTGTTGAACCGTGTTATGGTGACA

AAGATAAACGGCGGCATTGTTTTGCTACCTGGAAGAATATTTCTGGTTCC

ATTGAAATAGTGAAACAAGGTTGTTGGCTGGATGATATCAACTGCTATGA

CAGGACTGATTGTGTAGAAAAAAAAGACAGCCCTGAAGTATATTTTTGTT

GCTGTGAGGGCAATATGTGTAATGAAAAGTTTTCTTATTTTCCAGAGATG

GAAGTCACACAGCCCACTTCAAATCCAGTTACACCTAAGCCACCC

In a specific embodiment, the invention relates to soluble ActRIIa polypeptides. As described herein, the term "soluble ActRIIa polypeptide" generally refers to polypeptides comprising an extracellular domain of an ActRIIa protein. The term "soluble ActRIIa polypeptide," as used herein, includes any naturally occurring extracellular domain of an ActRIIa protein as well as any variants thereof (including mutants, fragments and peptidomimetic forms). An activin-binding ActRIIa polypeptide is one that retains the ability to bind to activin, including, for example, activin AA, AB, BB, or forms that include a C or E subunit. Optionally, an activin-binding ActRIIa polypeptide will bind to activin AA with a dissociation constant of 1 nM or less. The extracellular domain of an ActRIIa protein binds to activin and is generally soluble in physiological conditions, and thus can be termed a soluble, activin-binding ActRIIa polypeptide. Examples of soluble, activin-binding ActRIIa polypeptides include the soluble polypeptides illustrated in SEQ ID NOs: 2, 3, 7, 12 and 13. SEQ ID NO:7 is referred to as ActRIIa-hFc, and is described further in the Examples. Other examples of soluble, activin-binding ActRIIa polypeptides comprise a signal sequence in addition to the extracellular domain of an ActRIIa protein, for example, the honey bee mellitin leader sequence (SEQ ID NO: 8), the tissue plaminogen activator (TPA) leader (SEQ ID NO: 9) or the native ActRIIa leader (SEQ ID NO: 10). The ActRIIa-hFc polypeptide illustrated in SEQ ID NO: 13 uses a TPA leader.

A general formula for an active ActRIIa variant protein is one that comprises amino acids 12-82 of SEQ ID No. 2, respectively, but optionally beginning at a position ranging from 1-5 or 3-5 and ending at a position ranging from 110-116 or 110-115, respectively, and comprising no more than 1, 2, 5, 10 or 15 conservative amino acid changes in the ligand binding pocket, and zero, one or more non-conservative alterations at positions 40, 53, 55, 74, 79 and/or 82 in the ligand binding pocket. Such a protein may comprise an amino acid sequence that retains greater than 80%, 90%, 95% or 99% sequence identity to the sequence of amino acids 29-109 of SEQ ID NO: 2.

Functionally active fragments of ActRIIa polypeptides can be obtained by screening polypeptides recombinantly produced from the corresponding fragment of the nucleic acid encoding an ActRIIa polypeptide. In addition, fragments can be chemically synthesized using techniques known in the art such as conventional Merrifield solid phase f-Moc or t-Boc chemistry. The fragments can be produced (recombinantly or by chemical synthesis) and tested to identify those peptidyl fragments that can function as antagonists (inhibitors) of ActRIIa protein or signaling mediated by activin.

Functionally active variants of ActRIIa polypeptides can be obtained by screening libraries of modified polypeptides recombinantly produced from the corresponding mutagenized nucleic acids encoding an ActRIIa polypeptide. The variants can be produced and tested to identify those that can function as antagonists (inhibitors) of ActRIIa protein or signaling mediated by activin. In certain embodiments, a functional variant of the ActRIIa polypeptides comprises an amino acid sequence that is at least 75% identical to an amino acid sequence selected from SEQ ID NOs: 2 or 3. In certain cases, the functional variant has an amino acid sequence at least 80%, 85%, 90%, 95%, 97%, 98%, 99% or 100% identical to an amino acid sequence selected from SEQ ID NOs: 2 or 3.

Functional variants may be generated by modifying the structure of an ActRIIa polypeptide for such purposes as enhancing therapeutic efficacy, or stability (e.g., ex vivo shelf life and resistance to proteolytic degradation in vivo). Such modified ActRIIa polypeptides when selected to retain activin binding, are considered functional equivalents of the naturally-occurring ActRIIa polypeptides. Modified ActRIIa polypeptides can also be produced, for instance, by amino acid substitution, deletion, or addition. For instance, it is reasonable to expect that an isolated replacement of a leucine with an isoleucine or valine, an aspartate with a glutamate, a threonine with a serine, or a similar replacement of an amino acid with a structurally related amino acid (e.g., conservative mutations) will not have a major effect on the biological activity of the resulting molecule. Conservative replacements are those that take place within a family of amino acids that are related in their side chains. Whether a change in the amino acid sequence of an ActRIIa polypeptide results in a functional homolog can be readily determined by assessing the ability of the variant ActRIIa polypeptide to produce a response in cells in a fashion similar to the wild-type ActRIIa polypeptide.

In certain embodiments, the present invention contemplates specific mutations of the ActRIIa polypeptides so as to alter the glycosylation of the polypeptide. Such mutations may be selected so as to introduce or eliminate one or more glycosylation sites, such as O-linked or N-linked glycosylation sites. Asparagine-linked glycosylation recognition sites generally comprise a tripeptide sequence, asparagine-X-threonine or asparagine-X-serine (where "X" is any amino acid) which is specifically recognized by appropriate cellular glycosylation enzymes. The alteration may also be made by the addition of, or substitution by, one or more serine or threonine residues to the sequence of the wild-type ActRIIa polypeptide (for O-linked glycosylation sites). A variety of amino acid substitutions or deletions at one or both of the first or third amino acid positions of a glycosylation recognition site (and/or amino acid deletion at the second position) results in non-glycosylation at the modified tripeptide sequence. Another means of increasing the number of carbohydrate moieties on an ActRIIa polypeptide is by chemical or enzymatic coupling of glycosides to the ActRIIa polypeptide. Depending on the coupling mode used, the sugar(s) may be attached to (a) arginine and histidine; (b) free carboxyl groups; (c) free sulfhydryl groups such as those of cysteine; (d) free hydroxyl groups such as those of serine, threonine, or hydroxyproline; (e) aromatic residues such as those of phenylalanine, tyrosine, or tryptophan; or (f) the amide group of glutamine. Removal of one or more carbohydrate moieties present on an ActRIIa polypeptide may be accomplished chemically and/or enzymatically. Chemical deglycosylation may involve, for example, exposure of the ActRIIa polypeptide to the compound trifluoromethanesulfonic acid, or an equivalent compound. This treatment results in the cleavage of most or all sugars except the linking sugar (N-acetylglucosamine or N-acetylgalactosamine), while leaving the amino acid sequence intact. Enzymatic cleavage of carbohydrate moieties on ActRIIa polypeptides can be achieved by the use of a variety of endo- and exo-glycosidases as described by Thotakura et al. (1987) Meth. Enzymol. 138: 350. The sequence of an ActRIIa polypeptide may be adjusted, as appropriate, depending on the type of expression system used, as mammalian, yeast, insect and plant cells may all introduce differing glycosylation patterns that can be affected by the amino acid sequence of the peptide. In general, ActRIIa proteins for use in humans may be expressed in a mammalian cell line that provides proper glycosylation, such as HEK293 or CHO cell lines, although other mammalian expression cell lines are expected to be useful as well. Other non-mammalian cell lines may be used (e.g., yeast, *E. coli*, insect cells), and in some cases, such cell lines may be engineered to include enzymes that confer mammalian-type glycosylation patterns on the expressed proteins.

This disclosure further contemplates a method of generating mutants, particularly sets of combinatorial mutants of an ActRIIa polypeptide, as well as truncation mutants; pools of combinatorial mutants are especially useful for identifying functional variant sequences. The purpose of screening such combinatorial libraries may be to generate, for example, ActRIIa polypeptide variants which bind to activin or other ligands. A variety of screening assays are provided below, and such assays may be used to evaluate variants. For example, an ActRIIa polypeptide variant may be screened for ability to bind to an ActRIIa ligand, to prevent binding of an ActRIIa ligand to an ActRIIa polypeptide or to interfere with signaling caused by an ActRIIa ligand.

The activity of an ActRIIa polypeptide or its variants may also be tested in a cell-based or in vivo assay. For example, the effect of an ActRIIa polypeptide variant on the expression of genes involved in hematopoiesis may be assessed. This may, as needed, be performed in the presence of one or more recombinant ActRIIa ligand proteins (e.g., activin), and cells may be transfected so as to produce an ActRIIa polypeptide and/or variants thereof, and optionally, an ActRIIa ligand. Likewise, an ActRIIa polypeptide may be administered to a mouse or other animal, and one or more blood measurements, such as an RBC count, hemoglobin, or reticulocyte count may be assessed.

Combinatorially-derived variants can be generated which have a selective or generally increased potency relative to a naturally occurring ActRIIa polypeptide. Likewise, mutagenesis can give rise to variants which have intracellular half-lives dramatically different than the corresponding a wild-type ActRIIa polypeptide. For example, the altered protein can be rendered either more stable or less stable to proteolytic degradation or other cellular processes which result in destruction of, or otherwise inactivation of a native ActRIIa polypeptide. Such variants, and the genes which encode them, can be utilized to alter ActRIIa polypeptide levels by modulating the half-life of the ActRIIa polypeptides. For instance, a short half-life can give rise to more transient biological effects and, when part of an inducible expression system, can allow tighter control of recombinant ActRIIa polypeptide levels within the cell. In an Fc fusion protein, mutations may be made in the linker (if any) and/or the Fc portion to alter the half-life of the protein.

A combinatorial library may be produced by way of a degenerate library of genes encoding a library of polypeptides which each include at least a portion of potential ActRIIa polypeptide sequences. For instance, a mixture of synthetic oligonucleotides can be enzymatically ligated into gene sequences such that the degenerate set of potential ActRIIa polypeptide nucleotide sequences are expressible as individual polypeptides, or alternatively, as a set of larger fusion proteins (e.g., for phage display).

There are many ways by which the library of potential homologs can be generated from a degenerate oligonucleotide sequence. Chemical synthesis of a degenerate gene sequence can be carried out in an automatic DNA synthesizer, and the synthetic genes can then be ligated into an appropriate vector for expression. The synthesis of degenerate oligonucleotides is well known in the art (see for example, Narang, S A (1983) Tetrahedron 39:3; Itakura et al., (1981) Recombinant DNA, Proc. 3rd Cleveland Sympos. Macromolecules, ed. A G Walton, Amsterdam: Elsevier pp273-289; Itakura et al., (1984) Annu. Rev. Biochem. 53:323; Itakura et al., (1984) Science 198:1056; Ike et al., (1983) Nucleic Acid Res. 11:477). Such techniques have been employed in the directed evolution of other proteins (see, for example, Scott et al., (1990) Science 249:386-390; Roberts et al., (1992) PNAS USA 89:2429-2433; Devlin et al., (1990) Science 249: 404-406; Cwirla et al., (1990) PNAS USA 87: 6378-6382; as well as U.S. Pat. Nos. 5,223,409, 5,198,346, and 5,096,815).

Alternatively, other forms of mutagenesis can be utilized to generate a combinatorial library. For example, ActRIIa polypeptide variants can be generated and isolated from a library by screening using, for example, alanine scanning mutagenesis and the like (Ruf et al., (1994) Biochemistry 33:1565-1572; Wang et al., (1994) J. Biol. Chem. 269:3095-3099; Balint et al., (1993) Gene 137:109-118; Grodberg et al., (1993) Eur. J. Biochem. 218:597-601; Nagashima et al., (1993) J. Biol. Chem. 268:2888-2892; Lowman et al., (1991) Biochemistry 30:10832-10838; and Cunningham et al., (1989) Science 244:1081-1085), by linker scanning mutagenesis (Gustin et al., (1993) Virology 193:653-660; Brown et al., (1992) Mol. Cell Biol. 12:2644-2652; McKnight et al., (1982) Science 232:316); by saturation mutagenesis (Meyers et al., (1986) Science 232:613); by PCR mutagenesis (Leung et al., (1989) Method Cell Mol Biol 1:11-19); or by random mutagenesis, including chemical mutagenesis, etc. (Miller et al., (1992) A Short Course in Bacterial Genetics, CSHL Press, Cold Spring Harbor, N.Y.; and Greener et al., (1994) Strategies in Mol Biol 7:32-34). Linker scanning mutagenesis, particularly in a combinatorial setting, is an attractive method for identifying truncated (bioactive) forms of ActRIIa polypeptides.

A wide range of techniques are known in the art for screening gene products of combinatorial libraries made by point mutations and truncations, and, for that matter, for screening cDNA libraries for gene products having a certain property. Such techniques will be generally adaptable for rapid screening of the gene libraries generated by the combinatorial mutagenesis of ActRIIa polypeptides. The most widely used techniques for screening large gene libraries typically comprises cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Preferred assays include activin binding assays and activin-mediated cell signaling assays.

In certain embodiments, the ActRIIa polypeptides of the invention may further comprise post-translational modifications in addition to any that are naturally present in the ActRIIa polypeptides. Such modifications include, but are not limited to, acetylation, carboxylation, glycosylation, phosphorylation, lipidation, and acylation. As a result, the modified ActRIIa polypeptides may contain non-amino acid elements, such as polyethylene glycols, lipids, poly- or monosaccharide, and phosphates. Effects of such non-amino acid elements on the functionality of an ActRIIa polypeptide may be tested as described herein for other ActRIIa polypeptide variants. When an ActRIIa polypeptide is produced in cells by cleaving a nascent form of the ActRIIa polypeptide, post-translational processing may also be important for correct folding and/or function of the protein. Different cells (such as CHO, HeLa, MDCK, 293, WI38, NIH-3T3 or HEK293) have specific cellular machinery and characteristic mechanisms for such post-translational activities and may be chosen to ensure the correct modification and processing of the ActRIIa polypeptides.

In certain aspects, functional variants or modified forms of the ActRIIa polypeptides include fusion proteins having at least a portion of the ActRIIa polypeptides and one or more fusion domains. Well known examples of such fusion domains include, but are not limited to, polyhistidine, Glu-Glu, glutathione S transferase (GST), thioredoxin, protein A, protein G, an immunoglobulin heavy chain constant region (Fc), maltose binding protein (MBP), or human serum albumin. A fusion domain may be selected so as to confer a desired property. For example, some fusion domains are particularly useful for isolation of the fusion proteins by affinity chromatography. For the purpose of affinity purification, relevant matrices for affinity chromatography, such as glutathione-, amylase-, and nickel- or cobalt-conjugated resins are used. Many of such matrices are available in "kit" form, such as the Pharmacia GST purification system and the QIAexpress™ system (Qiagen) useful with (HIS$_6$) (SEQ ID NO: 25) fusion partners. As another example, a fusion domain may be selected so as to facilitate detection of the ActRIIa polypeptides. Examples of such detection domains include the various fluorescent proteins (e.g., GFP) as well as "epitope tags," which are usually short peptide sequences for which a specific antibody is available. Well known epitope tags for which specific monoclonal antibodies are readily available include FLAG, influenza virus haemagglutinin (HA), and c-myc tags. In some cases, the fusion domains have a protease cleavage site, such as for Factor Xa or Thrombin, which allows the relevant protease to partially digest the fusion proteins and thereby liberate the recombinant proteins therefrom. The liberated proteins can then be isolated from the fusion domain by subsequent chromatographic separation. In certain preferred embodiments, an ActRIIa polypeptide is fused with a domain that stabilizes the ActRIIa polypeptide in vivo (a "stabilizer" domain). By "stabilizing" is meant anything that increases serum half life, regardless of whether this is because of decreased destruction, decreased clearance by the kidney, or other pharmacokinetic effect. Fusions with the Fc portion of an immunoglobulin are known to confer desirable pharmacokinetic properties on a wide range of proteins. Constant domains from an immunoglobulin, particularly an IgG heavy chain, may also be used as stabilizing domains. Likewise, fusions to human serum albumin can confer desirable properties. Other types of fusion domains that may be selected include multimerizing (e.g., dimerizing, tetramerizing) domains and functional domains (that confer an additional biological function, such as further stimulation of muscle growth).

As a specific example, the present invention provides a fusion protein comprising a soluble extracellular domain of ActRIIa fused to an Fc domain. An example of an IgG1 Fc domain is shown below (SEQ ID NO: 6).

```
THTCPPCPAPELLGGPSVFLFPPKPKDTLMISRTPEVTCVVVD (A) VS
HEDPEVKFNWYVDGVEVHNAKTKPREEQYNSTYRVVSVLTVLHQDWLNGK
EYKCK (A) VSNKALPVPIEKTISKAKGQPREPQVYTLPPSREEMTKNQ
VSLTCLVKGFYPSDIAVEWESNGQPENNYKTTPPVLDSDGPFFLYSKLTV
DKSRWQQGNVFSCSVMHEALHN (A) HYTQKSLSLSPGK*
```

Optionally, the Fc domain has one or more mutations at residues such as Asp-265, lysine 322, and Asn-434. In certain cases, the mutant Fc domain having one or more of these mutations (e.g., Asp-265 mutation) has reduced ability of binding to the Fcγ receptor relative to a wildtype Fc domain. In other cases, the mutant Fc domain having one or more of these mutations (e.g., Asn-434 mutation) has increased ability of binding to the MHC class I-related Fc-receptor (FcRN) relative to a wildtype Fc domain. Fc domains from IgG2, IgG3 and IgG4 may also be used.

It is understood that different elements of the fusion proteins may be arranged in any manner that is consistent with the desired functionality. For example, an ActRIIa polypeptide may be placed C-terminal to a heterologous domain, or, alternatively, a heterologous domain may be placed C-terminal to an ActRIIa polypeptide. The ActRIIa polypeptide domain and the heterologous domain need not be adjacent in a fusion protein, and additional domains or amino acid sequences may be included C- or N-terminal to either domain or between the domains.

In certain embodiments, the ActRIIaa polypeptides of the present invention contain one or more modifications that are capable of stabilizing the ActRIIa polypeptides. For example, such modifications enhance the in vitro half life of the ActRIIa polypeptides, enhance circulatory half life of the ActRIIa polypeptides or reducing proteolytic degradation of the ActRIIa polypeptides. Such stabilizing modifications include, but are not limited to, fusion proteins (including, for example, fusion proteins comprising an ActRIIa polypeptide and a stabilizer domain), modifications of a glycosylation site (including, for example, addition of a glycosylation site to an ActRIIa polypeptide), and modifications of carbohydrate moiety (including, for example, removal of carbohydrate moieties from an ActRIIa polypeptide). As used herein, the term "stabilizer domain" not only refers to a fusion domain (e.g., Fc) as in the case of fusion proteins, but also includes nonproteinaceous modifications such as a carbohydrate moiety, or nonproteinaceous moiety, such as polyethylene glycol.

In certain embodiments, the present invention makes available isolated and/or purified forms of the ActRIIa polypeptides, which are isolated from, or otherwise substantially free of, other proteins. ActRIIa polypeptides will generally be produced by expression from recombinant nucleic acids.

3. Nucleic Acids Encoding ActRIIa Polypeptides

In certain aspects, the invention provides isolated and/or recombinant nucleic acids encoding any of the ActRIIa polypeptides (e.g., soluble ActRIIa polypeptides), including fragments, functional variants and fusion proteins disclosed herein. For example, SEQ ID NO: 4 encodes the naturally occurring human ActRIIa precursor polypeptide, while SEQ ID NO: 5 encodes the processed extracellular domain of ActRIIa. The subject nucleic acids may be single-stranded or double stranded. Such nucleic acids may be DNA or RNA molecules. These nucleic acids may be used, for example, in methods for making ActRIIa polypeptides or as direct therapeutic agents (e.g., in a gene therapy approach).

In certain aspects, the subject nucleic acids encoding ActRIIa polypeptides are further understood to include nucleic acids that are variants of SEQ ID NO: 4 or 5.

In certain embodiments, the invention provides isolated or recombinant nucleic acid sequences that are at least 80%, 85%, 90%, 95%, 97%, 98%, 99% or 100% identical to SEQ ID NOs: 4 or 5. One of ordinary skill in the art will appreciate that nucleic acid sequences complementary to SEQ ID NOs: 4 or 5, and variants of SEQ ID NOs: 4 or 5 are also within the scope of this invention. In further embodiments, the nucleic acid sequences of the invention can be isolated, recombinant, and/or fused with a heterologous nucleotide sequence, or in a DNA library.

In other embodiments, nucleic acids of the invention also include nucleotide sequences, and the ActRIIa polypeptides encoded by such nucleic acids, that hybridize under highly stringent conditions to the nucleotide sequence designated in SEQ ID NOs: 4 or 5, complement sequence of SEQ ID NOs: 4 or 5 or fragments thereof. As discussed above, one of ordinary skill in the art will understand readily that appropriate stringency conditions which promote DNA hybridization can be varied. One of ordinary skill in the art will understand readily that appropriate stringency conditions which promote DNA hybridization can be varied. For example, one could perform the hybridization at 6.0× sodium chloride/sodium citrate (SSC) at about 45° C., followed by a wash of 2.0×SSC at 50° C. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or temperature or salt concentration may be held constant while the other variable is changed. In one embodiment, the invention provides nucleic acids which hybridize under low stringency conditions of 6×SSC at room temperature followed by a wash at 2×SSC at room temperature.

Isolated nucleic acids which differ from the nucleic acids as set forth in SEQ ID NOs: 4 or 5 due to degeneracy in the genetic code are also within the scope of the invention. For example, a number of amino acids are designated by more than one triplet. Codons that specify the same amino acid, or synonyms (for example, CAU and CAC are synonyms for histidine) may result in "silent" mutations which do not affect the amino acid sequence of the protein. However, it is expected that DNA sequence polymorphisms that do lead to changes in the amino acid sequences of the subject proteins will exist among mammalian cells. One skilled in the art will appreciate that these variations in one or more nucleotides (up to about 3-5% of the nucleotides) of the nucleic acids encoding a particular protein may exist among individuals of a given species due to natural allelic variation. Any and all such nucleotide variations and resulting amino acid polymorphisms are within the scope of this invention.

In certain embodiments, the recombinant nucleic acids of the invention may be operably linked to one or more regulatory nucleotide sequences in an expression construct. Regulatory nucleotide sequences will generally be appropriate to the host cell used for expression. Numerous types of appropriate expression vectors and suitable regulatory sequences are known in the art for a variety of host cells. Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the invention. The promoters may be either naturally occurring promoters, or hybrid promoters that combine elements of more than one promoter. An expression construct may be present in a cell on an episome, such as a plasmid, or the expression construct may be inserted in a chromosome. In a preferred embodiment, the expression vector contains a selectable marker gene to allow the selection of transformed host cells. Selectable marker genes are well known in the art and will vary with the host cell used.

In certain aspects of the invention, the subject nucleic acid is provided in an expression vector comprising a nucleotide sequence encoding an ActRIIa polypeptide and operably linked to at least one regulatory sequence. Regulatory sequences are art-recognized and are selected to direct expression of the ActRIIa polypeptide. Accordingly, the term regulatory sequence includes promoters, enhancers, and other expression control elements. Exemplary regulatory sequences are described in Goeddel; *Gene Expression Technology: Methods in Enzymology*, Academic Press, San Diego, Calif. (1990). For instance, any of a wide variety of expression control sequences that control the expression of a DNA sequence when operatively linked to it may be used in these vectors to express DNA sequences encoding an ActRIIa polypeptide. Such useful expression control sequences, include, for example, the early and late promoters of SV40, tet promoter, adenovirus or cytomegalovirus immediate early promoter, RSV promoters, the lac system, the trp system, the TAC or TRC system, T7 promoter whose expression is directed by T7 RNA polymerase, the major operator and promoter regions of phage lambda, the control regions for fd coat protein, the promoter for 3-phosphoglycerate kinase or other glycolytic enzymes, the promoters of acid phosphatase, e.g., Pho5, the promoters of the yeast α-mating factors, the polyhedron promoter of the baculovirus system and other sequences known to control the expression of genes of prokaryotic or eukaryotic cells or their viruses, and various combinations thereof. It should be understood that the design of the expression vector may depend on such factors as the choice of the host cell to be transformed and/or the type of protein desired to be expressed. Moreover, the vector's copy number, the ability to control that copy number and the expression of any other protein encoded by the vector, such as antibiotic markers, should also be considered.

A recombinant nucleic acid of the invention can be produced by ligating the cloned gene, or a portion thereof, into a vector suitable for expression in either prokaryotic cells, eukaryotic cells (yeast, avian, insect or mammalian), or both. Expression vehicles for production of a recombinant ActRIIa polypeptide include plasmids and other vectors. For instance, suitable vectors include plasmids of the types: pBR322-derived plasmids, pEMBL-derived plasmids, pEX-derived plasmids, pBTac-derived plasmids and pUC-derived plasmids for expression in prokaryotic cells, such as *E. coli*.

Some mammalian expression vectors contain both prokaryotic sequences to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papilloma virus (BPV-1), or Epstein-Barr virus (pHEBo, pREP-derived and p205) can be used for transient expression of proteins in eukaryotic cells. Examples of other viral (including retroviral) expression systems can be found below in the description of gene therapy delivery systems. The various methods employed in the preparation of the plasmids and in transformation of host organisms are well known in the art. For other suitable expression systems for both prokaryotic and eukaryotic cells, as well as general recombinant procedures, see *Molecular Cloning A Laboratory Manual*, 3rd Ed., ed. by Sambrook, Fritsch and Maniatis (Cold Spring Harbor Laboratory Press, 2001). In some instances, it may be desirable to express the recombinant polypeptides by the use of a baculovirus expression system. Examples of such baculovirus expression systems include pVL-derived vectors (such as pVL1392, pVL1393 and pVL941), pAcUW-derived vectors (such as pAcUW1), and pBlueBac-derived vectors (such as the β-gal containing pBlueBac III).

In a preferred embodiment, a vector will be designed for production of the subject ActRIIa polypeptides in CHO cells, such as a Pcmv-Script vector (Stratagene, La Jolla, Calif.), pcDNA4 vectors (Invitrogen, Carlsbad, Calif.) and pCI-neo vectors (Promega, Madison, Wis.). As will be apparent, the subject gene constructs can be used to cause expression of the subject ActRIIa polypeptides in cells propagated in culture, e.g., to produce proteins, including fusion proteins or variant proteins, for purification.

This disclosure also pertains to a host cell transfected with a recombinant gene including a coding sequence (e.g., SEQ ID NO: 4 or 5) for one or more of the subject ActRIIa polypeptides. The host cell may be any prokaryotic or eukaryotic cell. For example, an ActRIIa polypeptide of the invention may be expressed in bacterial cells such as *E. coli*, insect cells (e.g., using a baculovirus expression system), yeast, or mammalian cells. Other suitable host cells are known to those skilled in the art.

Accordingly, the present invention further pertains to methods of producing the subject ActRIIa polypeptides. For example, a host cell transfected with an expression vector encoding an ActRIIa polypeptide can be cultured under appropriate conditions to allow expression of the ActRIIa polypeptide to occur. The ActRIIa polypeptide may be secreted and isolated from a mixture of cells and medium containing the ActRIIa polypeptide. Alternatively, the ActRIIa polypeptide may be retained cytoplasmically or in a membrane fraction and the cells harvested, lysed and the protein isolated. A cell culture includes host cells, media and other byproducts. Suitable media for cell culture are well known in the art. The subject ActRIIa polypeptides can be isolated from cell culture medium, host cells, or both, using techniques known in the art for purifying proteins, including ion-exchange chromatography, gel filtration chromatography, ultrafiltration, electrophoresis, immunoaffinity purification with antibodies specific for particular epitopes of the ActRIIa polypeptides and affinity purification with an agent that binds to a domain fused to the ActRIIa polypeptide (e.g., a protein A column may be used to purify an ActRIIa-Fc fusion). In a preferred embodiment, the ActRIIa polypeptide is a fusion protein containing a domain which facilitates its purification. In a preferred embodiment, purification is achieved by a series of column chromatography steps, including, for example, three or more of the following, in any order:

protein A chromatography, Q sepharose chromatography, phenylsepharose chromatography, size exclusion chromatography, and cation exchange chromatography. The purification could be completed with viral filtration and buffer exchange. As demonstrated herein, ActRIIa-hFc protein was purified to a purity of >98% as determined by size exclusion chromatography and >95% as determined by SDS PAGE. This level of purity was sufficient to achieve desirable results in mice, rats, non-human primates and humans.

In another embodiment, a fusion gene coding for a purification leader sequence, such as a poly-(His)/enterokinase cleavage site sequence at the N-terminus of the desired portion of the recombinant ActRIIa polypeptide, can allow purification of the expressed fusion protein by affinity chromatography using a $Ni^{2+}$ metal resin. The purification leader sequence can then be subsequently removed by treatment with enterokinase to provide the purified ActRIIa polypeptide (e.g., see Hochuli et al., (1987) *J. Chromatography* 411:177; and Janknecht et al., *PNAS USA* 88:8972).

Techniques for making fusion genes are well known. Essentially, the joining of various DNA fragments coding for different polypeptide sequences is performed in accordance with conventional techniques, employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, eds. Ausubel et al., John Wiley & Sons: 1992).

4. Alternative Activin and ActRIIa Antagonists

The data presented herein demonstrates that antagonists of activin-ActRIIa signaling can be used to increase red blood cell or hemoglobin levels. Although soluble ActRIIa polypeptides, and particularly ActRIIa-Fc, are preferred antagonists, and although such antagonists may affect red blood cell levels through a mechanism other than activin antagonism (e.g., activin inhibition may be an indicator of the tendency of an agent to inhibit the activities of a spectrum of molecules, including, perhaps, other members of the TGF-beta superfamily, and such collective inhibition may lead to the desired effect on hematopoiesis), other types of activin-ActRIIa antagonists are expected to be useful, including anti-activin (e.g., activin $\beta_A$, $\beta_B$, $\beta_C$ and $\beta_E$) antibodies, anti-ActRIIa antibodies, antisense, RNAi or ribozyme nucleic acids that inhibit the production of ActRIIa, and other inhibitors of activin or ActRIIa, particularly those that disrupt activin-ActRIIa binding.

An antibody that is specifically reactive with an ActRIIa polypeptide (e.g., a soluble ActRIIa polypeptide) and which either binds competitively to ligand with the ActRIIa polypeptide or otherwise inhibits ActRIIa-mediated signaling may be used as an antagonist of ActRIIa polypeptide activities. Likewise, an antibody that is specifically reactive with an activin $\beta_A$, $\beta_B$, $\beta_C$ or $\beta_E$ polypeptide, or any heterodimer thereof, and which disrupts ActRIIa binding may be used as an antagonist.

By using immunogens derived from an ActRIIa polypeptide or an activin polypeptide, anti-protein/anti-peptide antisera or monoclonal antibodies can be made by standard protocols (see, for example, Antibodies: A Laboratory Manual ed. by Harlow and Lane (Cold Spring Harbor Press: 1988)). A mammal, such as a mouse, a hamster or rabbit can be immunized with an immunogenic form of the activin or ActRIIa polypeptide, an antigenic fragment which is capable of eliciting an antibody response, or a fusion protein. Techniques for conferring immunogenicity on a protein or peptide include conjugation to carriers or other techniques well known in the art. An immunogenic portion of an ActRIIa or activin polypeptide can be administered in the presence of adjuvant. The progress of immunization can be monitored by detection of antibody titers in plasma or serum. Standard ELISA or other immunoassays can be used with the immunogen as antigen to assess the levels of antibodies.

Following immunization of an animal with an antigenic preparation of an activin or ActRIIa polypeptide, antisera can be obtained and, if desired, polyclonal antibodies can be isolated from the serum. To produce monoclonal antibodies, antibody-producing cells (lymphocytes) can be harvested from an immunized animal and fused by standard somatic cell fusion procedures with immortalizing cells such as myeloma cells to yield hybridoma cells. Such techniques are well known in the art, and include, for example, the hybridoma technique (originally developed by Kohler and Milstein, (1975) Nature, 256: 495-497), the human B cell hybridoma technique (Kozbar et al., (1983) Immunology Today, 4: 72), and the EBV-hybridoma technique to produce human monoclonal antibodies (Cole et al., (1985) Monoclonal Antibodies and Cancer Therapy, Alan R. Liss, Inc. pp. 77-96). Hybridoma cells can be screened immunochemically for production of antibodies specifically reactive with an activin or ActRIIa polypeptide and monoclonal antibodies isolated from a culture comprising such hybridoma cells.

The term "antibody" as used herein is intended to include whole antibodies, e.g., of any isotype (IgG, IgA, IgM, IgE, etc), and includes fragments or domains of immunoglobulins which are reactive with a selected antigen. Antibodies can be fragmented using conventional techniques and the fragments screened for utility and/or interaction with a specific epitope of interest. Thus, the term includes segments of proteolytically-cleaved or recombinantly-prepared portions of an antibody molecule that are capable of selectively reacting with a certain protein. Non-limiting examples of such proteolytic and/or recombinant fragments include Fab, F(ab')2, Fab', Fv, and single chain antibodies (scFv) containing a V[L] and/or V[H] domain joined by a peptide linker. The scFv's may be covalently or non-covalently linked to form antibodies having two or more binding sites. The term antibody also includes polyclonal, monoclonal, or other purified preparations of antibodies and recombinant antibodies. The term "recombinant antibody", means an antibody, or antigen binding domain of an immunoglobulin, expressed from a nucleic acid that has been constructed using the techniques of molecular biology, such as a humanized antibody or a fully human antibody developed from a single chain antibody. Single domain and single chain antibodies are also included within the term "recombinant antibody".

In certain embodiments, an antibody of the invention is a monoclonal antibody, and in certain embodiments, the invention makes available methods for generating novel antibodies. For example, a method for generating a monoclonal antibody that binds specifically to an ActRIIa polypeptide or activin polypeptide may comprise administering to a mouse an amount of an immunogenic composition comprising the antigen polypeptide effective to stimulate a detectable immune response, obtaining antibody-producing cells (e.g., cells from the spleen) from the mouse and fusing the antibody-producing cells with myeloma cells to obtain antibody-producing hybridomas, and testing the antibody-producing hybridomas to identify a hybridoma that produces a monoclonal antibody that binds specifically to the antigen. Once obtained, a hybridoma can be propagated in a cell culture, optionally in culture conditions where the hybridoma-derived cells produce the monoclonal antibody that binds specifically to the antigen. The monoclonal antibody may be purified from the cell culture.

The adjective "specifically reactive with" as used in reference to an antibody is intended to mean, as is generally understood in the art, that the antibody is sufficiently selective between the antigen of interest (e.g., an activin or ActRIIa polypeptide) and other antigens that are not of interest that the antibody is useful for, at minimum, detecting the presence of the antigen of interest in a particular type of biological sample. In certain methods employing the antibody, such as therapeutic applications, a higher degree of specificity in binding may be desirable. Monoclonal antibodies generally have a greater tendency (as compared to polyclonal antibodies) to discriminate effectively between the desired antigens and cross-reacting polypeptides. One characteristic that influences the specificity of an antibody:antigen interaction is the affinity of the antibody for the antigen. Although the desired specificity may be reached with a range of different affinities, generally preferred antibodies will have an affinity (a dissociation constant) of about $10^{-6}$, $10^{-7}$, $10^{-8}$, $10^{-9}$ M or less.

In addition, the techniques used to screen antibodies in order to identify a desirable antibody may influence the properties of the antibody obtained. For example, if an antibody is to be used for binding an antigen in solution, it may be desirable to test solution binding. A variety of different techniques are available for testing interaction between antibodies and antigens to identify particularly desirable antibodies. Such techniques include ELISAs, surface plasmon resonance binding assays (e.g., the Biacore™ binding assay, Biacore AB, Uppsala, Sweden), sandwich assays (e.g., the paramagnetic bead system of IGEN International, Inc., Gaithersburg, Md.), western blots, immunoprecipitation assays, and immunohistochemistry.

Examples of categories of nucleic acid compounds that are activin or ActRIIa antagonists include antisense nucleic acids, RNAi constructs and catalytic nucleic acid constructs. A nucleic acid compound may be single or double stranded. A double stranded compound may also include regions of overhang or non-complementarity, where one or the other of the strands is single stranded. A single stranded compound may include regions of self-complementarity, meaning that the compound forms a so-called "hairpin" or "stem-loop" structure, with a region of double helical structure. A nucleic acid compound may comprise a nucleotide sequence that is complementary to a region consisting of no more than 1000, no more than 500, no more than 250, no more than 100, or no more than 50, 35, 25, 22, 20, 18 or 15 nucleotides of the full-length ActRIIa nucleic acid sequence or activin $\beta_A$, $\beta_B$, $\beta_C$, or $\beta_E$ nucleic acid sequence. The region of complementarity will preferably be at least 8 nucleotides, and optionally about 18 to 35 nucleotides. A region of complementarity may fall within an intron, a coding sequence or a noncoding sequence of the target transcript, such as the coding sequence portion. Generally, a nucleic acid compound will have a length of about 8 to about 500 nucleotides or base pairs in length, and optionally the length will be about 14 to about 50 nucleotides. A nucleic acid may be a DNA (particularly for use as an antisense), RNA or RNA:DNA hybrid. Any one strand may include a mixture of DNA and RNA, as well as modified forms that cannot readily be classified as either DNA or RNA. Likewise, a double stranded compound may be DNA:DNA, DNA:RNA or RNA:RNA, and any one strand may also include a mixture of DNA and RNA, as well as modified forms that cannot readily be classified as either DNA or RNA. A nucleic acid compound may include any of a variety of modifications, including one or modifications to the backbone (the sugar-phosphate portion in a natural nucleic acid, including internucleotide linkages) or the base portion (the purine or pyrimidine portion of a natural nucleic acid). An antisense nucleic acid compound will preferably have a length of about 15 to about 30 nucleotides and will often contain one or more modifications to improve characteristics such as stability in the serum, in a cell or in a place where the compound is likely to be delivered, such as the stomach in the case of orally delivered compounds and the lung for inhaled compounds. In the case of an RNAi construct, the strand complementary to the target transcript will generally be RNA or modifications thereof. The other strand may be RNA, DNA or any other variation. The duplex portion of double stranded or single stranded "hairpin" RNAi construct will generally have a length of 18 to 40 nucleotides in length and optionally about 21 to 23 nucleotides in length, so long as it serves as a Dicer substrate. Catalytic or enzymatic nucleic acids may be ribozymes or DNA enzymes and may also contain modified forms. Nucleic acid compounds may inhibit expression of the target by about 50%, 75%, 90% or more when contacted with cells under physiological conditions and at a concentration where a nonsense or sense control has little or no effect. Preferred concentrations for testing the effect of nucleic acid compounds are 1, 5 and 10 micromolar. Nucleic acid compounds may also be tested for effects on, for example, red blood cell levels.

In certain embodiments, an activin-ActRIIa antagonist may be a follistatin polypeptide that antagonizes activin bioactivity and/or binds to activin. The term "follistatin polypeptide" includes polypeptides comprising any naturally occurring polypeptide of follistatin as well as any variants thereof (including mutants, fragments, fusions, and peptidomimetic forms) that retain a useful activity, and further includes any functional monomer or multimer of follistatin. Variants of follistatin polypeptides that retain activin binding properties can be identified based on previous studies involving follistatin and activin interactions. For example, WO2008/030367 discloses specific follistatin domains ("FSDs") that are shown to be important for activin binding. As shown below in SEQ ID NOs: 19-21, the N-terminus follistatin domain ("FSND" SEQ ID NO: 19), FSD2 (SEQ ID NO: 20), and to a lesser extent FSD1 (SEQ ID NO: 21) represent exemplary domains within follistatin important for activin binding. In addition, methods for making and testing libraries of polypeptides are described above in the context of ActRIIa polypeptides and such methods also pertain to making and testing variants of follistatin. Follistatin polypeptides include polypeptides derived from the sequence of any known follistatin having a sequence at least about 80% identical to the sequence of a follistatin polypeptide, and optionally at least 85%, 90%, 95%, 97%, 99% or greater identity. Examples of follistatin polypeptides include the mature follistatin polypeptide or shorter isoforms or other variants of the human follistatin precursor polypeptide (SEQ ID NO: 17) as described, for example, in WO2005/025601.

The human follistatin precursor polypeptide isoform FST344 is as follows:

```
                                                    (SEQ ID NO: 17)
MVRARHQPGGLCLLLLLLCQFMEDRSAQAGNCWLRQAKNGRCQVLYKTEL

SKEECCSTGRLSTSWTEEDVNDNTLFKWMIFNGGAPNCIPCKETCENVDC

GPGKKCRMNKKNKPRCVCAPDCSNITWKGPVCGLDGKTYRNECALLKARC

KEQPELEVQYQGRCKKTCRDVFCPGSSTCVVDQTNNAYCVTCNRICPEPA

SSEQYLCGNDGVTYSSACHLRKATCLLGRSIGLAYEGKCIKAKSCEDIQC

TGGKKCLWDFKVGRGRCSLCDELCPDSKSDEPVCASDNATYASECANKEA

ACSSGVLLEVKHGSCNSISEDTEEEEEDEDQDYSFPISSILEW
(SEQ ID NO: 17; NP_037541.1 FOLLISTATIN ISOFORM
FST344)
```

The signal peptide is single underlined; the last 27 residues in bold represent additional amino acids as compared to a shorter follistatin isoform FST317 (NP_006341) below.

The human follistatin precursor polypeptide isoform FST317 is as follows:

```
                                                    (SEQ ID NO: 18)
MVRARHQPGGLCLLLLLLCQFMEDRSAQAGNCWLRQAKNGRCQVLYKTEL

SKEECCSTGRLSTSWTEEDVNDNTLFKWMIFNGGAPNCIPCKETCENVDC

GPGKKCRMNKKNKPRCVCAPDCSNITWKGPVCGLDGKTYRNECALLKARC

KEQPELEVQYQGRCKKTCRDVFCPGSSTCVVDQTNNAYCVTCNRICPEPA

SSEQYLCGNDGVTYSSACHLRKATCLLGRSIGLAYEGKCIKAKSCEDIQC

TGGKKCLWDFKVGRGRCSLCDELCPDSKSDEPVCASDNATYASECANKEA

ACSSGVLLEVKHGSCN
```

The signal peptide is single underlined.

N-terminus follistatin domain (FSND) sequence is as follows:

```
                                                    (SEQ ID NO: 19; FSND)
GNCWLRQAKMGRCQVLYKTELSKEECCSTGRLSTSWTEEDVNDNTLFKWM

IFNGGAPNCIPCK
```

The FSD1 and FSD2 sequences are as follows:

```
ETCENVDCGPGKKCRMNKKNKPRCV         (SEQ ID NO: 20; FSD1)

KTCRDVFCPGSSTCVVDQTNNAYCVT        (SEQ ID NO: 21; FSD2)
```

In other embodiments, an activin-ActRIIa antagonist may be a follistatin-like related gene (FLRG) that antagonizes activin bioactivity and/or binds to activin. The term "FLRG polypeptide" includes polypeptides comprising any naturally occurring polypeptide of FLRG as well as any variants thereof (including mutants, fragments, fusions, and peptidomimetic forms) that retain a useful activity. Variants of FLRG polypeptides that retain activin binding properties can be identified using routine methods to assay FLRG and activin interactions. See, for example, U.S. Pat. No. 6,537,966. In addition, methods for making and testing libraries of polypeptides are described above in the context of ActRIIa polypeptides and such methods also pertain to making and testing variants of FLRG. FLRG polypeptides include polypeptides derived from the sequence of any known FLRG having a sequence at least about 80% identical to the sequence of an FLRG polypeptide, and optionally at least 85%, 90%, 95%, 97%, 99% or greater identity.

The human FLRG precursor polypeptide is as follows:

```
                                  (SEQ ID NO: 22; NP_005851)
MRPGAPGPLWPLPWGALAWAVGFVSSMGSGNPAPGGVCWLQQGGQEATCSL

VLQTDVTRAECCASGNIDTAWSNLTHPGNKINLLGFLGLVHCLPCKDSCD

GVECGPGKACRMLGGRPRCECAPDCSGLPARLQVCGSDGATYRDECELPA

ARCRGHPDLSVMYRGRCRKSCEHVVCPRPQSCVVDQTGSAHCVVCRAAPC

VPSSPGQELCGNNNVTYISSCHMRQATCFLGRSIGVRHAGSCAGTPEEPP

GGESAEEEENFV
```

The signal peptide is single underlined.

In certain embodiments, functional variants or modified forms of the follistatin polypeptides and FLRG polypeptides include fusion protein having at least a portion of the follistatin polypeptides or FLRG polypeptides and one or more fusion domains, such as, for example, domains that facilitate isolation, detection, stabilization or multimerization of the polypeptide. Suitable fusion domains are discussed in detail above with reference to the ActRIIa polypeptides. In one embodiment, an activin-ActRIIa antagonist is a fusion protein comprising an activin binding portion of a follistaton polypeptide fused to an Fc domain. In another embodiment, an activin-ActRIIa antagonist is a fusion protein comprising an activin binding portion of an FLRG polypeptide fused to an Fc domain. Follistatin and FLRG have been shown in the literature, and by the applicants with respect to FLRG, to have affinities for Activin A in the picomolar range, indicating that these agents will inhibit activin A signaling to a similar degree as ActRIIa-Fc.

5. Screening Assays

In certain aspects, the present invention relates to the use of ActRIIa polypeptides and activin polypeptides to identify compounds (agents) which are agonist or antagonists of the activin-ActRIIa signaling pathway. Compounds identified through this screening can be tested to assess their ability to modulate red blood cell, hemoglobin and/or reticulocyte levels in vivo or in vitro. These compounds can be tested, for example, in animal models.

There are numerous approaches to screening for therapeutic agents for increasing red blood cell or hemoglobin levels by targeting activin and ActRIIa signaling. In certain embodiments, high-throughput screening of compounds can be carried out to identify agents that perturb activin or ActRIIa-mediated effects on a selected cell line. In certain embodiments, the assay is carried out to screen and identify compounds that specifically inhibit or reduce binding of an ActRIIa polypeptide to activin. Alternatively, the assay can be used to identify compounds that enhance binding of an ActRIIa polypeptide to activin. In a further embodiment, the compounds can be identified by their ability to interact with an activin or ActRIIa polypeptide.

A variety of assay formats will suffice and, in light of the present disclosure, those not expressly described herein will nevertheless be comprehended by one of ordinary skill in the art. As described herein, the test compounds (agents) of the invention may be created by any combinatorial chemical method. Alternatively, the subject compounds may be naturally occurring biomolecules synthesized in vivo or in vitro. Compounds (agents) to be tested for their ability to act as modulators of tissue growth can be produced, for example, by bacteria, yeast, plants or other organisms (e.g., natural products), produced chemically (e.g., small molecules, including peptidomimetics), or produced recombinantly. Test compounds contemplated by the present invention include non-peptidyl organic molecules, peptides, polypeptides, peptidomimetics, sugars, hormones, and nucleic acid molecules. In a specific embodiment, the test agent is a small organic molecule having a molecular weight of less than about 2,000 Daltons.

The test compounds of the invention can be provided as single, discrete entities, or provided in libraries of greater complexity, such as made by combinatorial chemistry. These libraries can comprise, for example, alcohols, alkyl halides, amines, amides, esters, aldehydes, ethers and other classes of organic compounds. Presentation of test compounds to the test system can be in either an isolated form or as mixtures of compounds, especially in initial screening steps. Optionally, the compounds may be optionally derivatized with other compounds and have derivatizing groups that facilitate isolation of the compounds. Non-limiting examples of derivatizing groups include biotin, fluorescein, digoxygenin, green fluorescent protein, isotopes, polyhistidine, magnetic beads, glutathione S transferase (GST), photoactivatible crosslinkers or any combinations thereof.

In many drug screening programs which test libraries of compounds and natural extracts, high throughput assays are desirable in order to maximize the number of compounds surveyed in a given period of time. Assays which are performed in cell-free systems, such as may be derived with purified or semi-purified proteins, are often preferred as "primary" screens in that they can be generated to permit rapid development and relatively easy detection of an alteration in a molecular target which is mediated by a test compound. Moreover, the effects of cellular toxicity or bioavailability of the test compound can be generally ignored in the in vitro system, the assay instead being focused primarily on the effect of the drug on the molecular target as may be manifest in an alteration of binding affinity between an ActRIIa polypeptide and activin.

Merely to illustrate, in an exemplary screening assay of the present invention, the compound of interest is contacted with an isolated and purified ActRIIa polypeptide which is ordinarily capable of binding to activin. To the mixture of the compound and ActRIIa polypeptide is then added a composition containing an ActRIIa ligand. Detection and quantification of ActRIIa/activin complexes provides a means for determining the compound's efficacy at inhibiting (or potentiating) complex formation between the ActRIIa polypeptide and activin. The efficacy of the compound can be assessed by generating dose response curves from data obtained using various concentrations of the test compound. Moreover, a control assay can also be performed to provide a baseline for comparison. For example, in a control assay, isolated and purified activin is added to a composition containing the ActRIIa polypeptide, and the formation of ActRIIa/activin complex is quantitated in the absence of the test compound. It will be understood that, in general, the order in which the reactants may be admixed can be varied, and can be admixed simultaneously. Moreover, in place of purified proteins, cellular extracts and lysates may be used to render a suitable cell-free assay system.

Complex formation between the ActRIIa polypeptide and activin may be detected by a variety of techniques. For instance, modulation of the formation of complexes can be quantitated using, for example, detectably labeled proteins such as radiolabeled (e.g., $^{32}P$, $^{35}S$, $^{14}C$ or $^{3}H$), fluorescently labeled (e.g., FITC), or enzymatically labeled ActRIIa polypeptide or activin, by immunoassay, or by chromatographic detection.

In certain embodiments, the present invention contemplates the use of fluorescence polarization assays and fluorescence resonance energy transfer (FRET) assays in measuring, either directly or indirectly, the degree of interaction between an ActRIIa polypeptide and its binding protein. Further, other modes of detection, such as those based on optical waveguides (PCT Publication WO 96/26432 and U.S. Pat. No. 5,677,196), surface plasmon resonance (SPR), surface charge sensors, and surface force sensors, are compatible with many embodiments of the invention.

Moreover, the present invention contemplates the use of an interaction trap assay, also known as the "two hybrid assay," for identifying agents that disrupt or potentiate interaction between an ActRIIa polypeptide and its binding protein. See for example, U.S. Pat. No. 5,283,317; Zervos et al. (1993) Cell 72:223-232; Madura et al. (1993) J Biol Chem 268: 12046-12054; Bartel et al. (1993) Biotechniques 14:920-924; and Iwabuchi et al. (1993) Oncogene 8:1693-1696). In a specific embodiment, the present invention contemplates the use of reverse two hybrid systems to identify compounds (e.g., small molecules or peptides) that dissociate interactions between an ActRIIa polypeptide and its binding protein. See for example, Vidal and Legrain, (1999) Nucleic Acids Res 27:919-29; Vidal and Legrain, (1999) Trends Biotechnol 17:374-81; and U.S. Pat. Nos. 5,525,490; 5,955,280; and 5,965,368.

In certain embodiments, the subject compounds are identified by their ability to interact with an ActRIIa or activin polypeptide of the invention. The interaction between the compound and the ActRIIa or activin polypeptide may be covalent or non-covalent. For example, such interaction can be identified at the protein level using in vitro biochemical methods, including photo-crosslinking, radiolabeled ligand binding, and affinity chromatography (Jakoby W B et al., 1974, Methods in Enzymology 46: 1). In certain cases, the compounds may be screened in a mechanism based assay, such as an assay to detect compounds which bind to an activin or ActRIIa polypeptide. This may include a solid phase or fluid phase binding event. Alternatively, the gene encoding an activin or ActRIIa polypeptide can be transfected with a reporter system (e.g., β-galactosidase, luciferase, or green fluorescent protein) into a cell and screened against the library optionally by a high throughput screening or with individual members of the library. Other mechanism based binding assays may be used, for example, binding assays which detect changes in free energy. Binding assays can be performed with the target fixed to a well, bead or chip or captured by an immobilized antibody or resolved by capillary electrophoresis. The bound compounds may be detected usually using colorimetric or fluorescence or surface plasmon resonance.

6. Exemplary Therapeutic Uses

In certain embodiments, activin-ActRIIa antagonists (e.g., ActRIIa polypeptides) of the present invention can be used to increase red blood cell levels in mammals such as rodents and primates, and particularly human patients. In certain embodiments, the present invention provides methods of treating or preventing anemia in an individual in need thereof by administering to the individual a therapeutically effective amount of an activin-ActRIIa antagonist, such as an ActRIIa polypeptide. In certain embodiments, the present invention provides methods of promoting red blood cell formation in an individual by administering to the individual a therapeutically effective amount of an activin-ActRIIa antagonist, particularly an ActRIIa polypeptide. These methods may be used for therapeutic and prophylactic treatments of mammals, and particularly humans.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "treating" as used herein includes prophylaxis of the named condition or amelioration or elimination of the condition once it has been established. In either case, prevention or treatment may be discerned in the diagnosis provided by a physician or other health care provider and the intended result of administration of the therapeutic agent.

As shown herein, activin-ActRIIa antagonists may be used to increase red blood cell, hemoglobin or reticulocyte levels in healthy individuals, and such antagonists may be used in selected patient populations. Examples of appropriate patient populations include those with undesirably low red blood cell or hemoglobin levels, such as patients having an anemia, and those that are at risk for developing undesirably low red blood cell or hemoglobin levels, such as those patients that are about to undergo major surgery or other procedures that may result in substantial blood loss. In one embodiment, a patient with adequate red blood cell levels is treated with an activin-ActRIIa antagonist to increase red blood cell levels, and then blood is drawn and stored for later use in transfusions.

As described in the examples, activin-ActRIIa antagonists may stimulate red blood cell production by activation of splenic erythropoiesis. This novel mechanism indicates that these antagonists are likely to work synergistically with other anemia treatments, such as erythropoietin agonists (e.g., Epogen, Procrit, Aranesp, Epo mimics, Epo receptor agonists, etc.).

Activin-ActRIIa antagonists disclosed herein, and particularly ActRIIa-Fc proteins, may be used to increase red blood cell levels in patients having an anemia. When observing hemoglobin levels in humans, a level of less than normal for the appropriate age and gender category may be indicative of anemia, although individual variations are taken into account. For example, a hemoglobin level of 12 g/dl is generally considered the lower limit of normal in the general adult population. Potential causes include blood-loss, nutritional deficits, medication reaction, various problems with the bone marrow and many diseases. More particularly, anemia has been associated with a variety of disorders that include, for example, chronic renal failure, myelodysplastic syndrome (including Deletion 5 q MDS), myelofibrosis, rheumatoid arthritis, bone marrow transplantation. Anemia may also be associated with the following conditions: solid tumors (e.g. breast cancer, lung cancer, colon cancer); tumors of the lymphatic system (e.g. chronic lymphocyte leukemia, non-Hodgkins and Hodgkins lymphomas); tumors of the hematopoietic system (eg. leukemia, myelodysplastic syndrome, multiple myeloma); radiation therapy; chemotherapy (e.g. platinum containing regimens); inflammatory and autoimmune diseases, including, but not limited to, rheumatoid arthritis, other inflammatory arthritides, systemic lupus erythematosis (SLE), acute or chronic skin diseases (e.g. psoriasis), inflammatory bowel disease (e.g. Crohn's disease and ulcerative colitis); acute or chronic renal disease or failure including idiopathic or congenital conditions; acute or chronic liver disease; acute or chronic bleeding; situations where transfusion of red blood cells is not possible due to patient allo- or auto-antibodies and/or for religious reasons (e.g. some Jehovah's Witnesses); infections (e.g. malaria, osteomyelitis); hemoglobinopathies, including, for example, sickle cell disease, thalassemias; drug use or abuse, e.g. alcohol misuse; pediatric patients with anemia from any cause to avoid transfusion; and elderly patients or patients with underlying cardiopulmonary disease with anemia who cannot receive transfusions due to concerns about circulatory overload.

Activin-ActRIIa antagonists (e.g., ActRIIa polypeptides) would be appropriate for treating anemias of hypoproliferative bone marrow, which are typically associated with little change in RBC morphology. Hypoproliferative anemias include: 1) anemia of chronic disease, 2) anemia of kidney disease, and 3) anemia associated with hypometabolic states. In each of these types, endogenous erythropoietin levels are inappropriately low for the degree of anemia observed. Other hypoproliferative anemias include: 4) early-stage iron-deficient anemia, and 5) anemia caused by damage to the bone marrow. In these types, endogenous erythropoietin levels are appropriately elevated for the degree of anemia observed.

The most common type is anemia of chronic disease, which encompasses inflammation, infection, tissue injury, and conditions such as cancer, and is distinguished by both low erythropoietin levels and an inadequate response to erythropoietin in the bone marrow (Adamson, 2008, Harrison's Principles of Internal Medicine, 17th ed.; McGraw Hill, New York, pp 628-634). Many factors can contribute to cancer-related anemia. Some are associated with the disease process itself and the generation of inflammatory cytokines such as interleukin-1, interferon-gamma, and tumor necrosis factor (Born et al., 2001, Semen Oncol 28(Supply 8):1-6). Among its effects, inflammation induces the key iron-regulatory peptide deciding, thereby inhibiting iron export from macrophages and generally limiting iron availability for erythropoiesis (Gins, 2007, J Am Soc Nephrol 18:394-400). Blood loss through various routes can also contribute to cancer-related anemia. The prevalence of anemia due to cancer progression varies with cancer type, ranging from 5% in prostate cancer up to 90% in multiple myeloma. Cancer-related anemia has profound consequences for patients, including fatigue and reduced quality of life, reduced treatment efficacy, and increased mortality.

Chronic kidney disease is associated with hypoproliferative anemia that varies in severity with the degree of renal impairment. Such anemia is primarily due to inadequate production of erythropoietin and reduced survival of red blood cells. Chronic kidney disease usually proceeds gradually over a period of years or decades to end-stage (Stage-5) disease, at which point dialysis or kidney transplantation is required for patient survival. Anemia often develops early in this process and worsens as disease progresses. The clinical consequences of anemia of kidney disease are well-documented and include development of left ventricular hypertrophy, impaired cognitive function, reduced quality of life, and altered immune function (Levin et al., 1999, Am J Kidney Dis 27:347-354; Nissenson, 1992, Am J Kidney Dis 20(Suppl 1):21-24; Revicki et al., 1995, Am J Kidney Dis 25:548-554; Gafter et al., 1994, Kidney Int 45:224-231). As demonstrated by the Applicants in a mouse model of chronic kidney disease (see Example below), an ActRIIa polypeptide, or other activin-ActRIIa antagonist, can be used to treat anemia of kidney disease.

Many conditions resulting in a hypometabolic rate can produce a mild-to-moderate hypoproliferative anemia. Among such conditions are endocrine deficiency states. For example, anemia can occur in Addison's disease, hypothyroidism, hyperparathyroidism, or males who are castrated or treated with estrogen. Mild-to-moderate anemia can also occur with reduced dietary intake of protein, a condition particularly prevalent in the elderly. Finally, anemia can develop in patients with chronic liver disease arising from nearly any cause (Adamson, 2008, Harrison's Principles of Internal Medicine, 17th ed.; McGraw Hill, New York, pp 628-634).

Iron-deficiency anemia is the final stage in a graded progression of increasing iron deficiency which includes negative iron balance and iron-deficient erythropoiesis as intermediate stages. Iron deficiency can result from increased iron demand, decreased iron intake, or increased iron loss, as exemplified in conditions such as pregnancy, inadequate diet, intestinal malabsorption, acute or chronic inflammation, and acute or chronic blood loss. With mild-to-moderate anemia of this type, the bone marrow remains hypoproliferative, and RBC morphology is largely normal; however, even mild anemia can result in some microcytic hypochromic RBCs, and the transition to severe iron-deficient anemia is accompanied by hyperproliferation of the bone marrow and increasingly prevalent microcytic and hypochromic RBCs (Adamson, 2008, Harrison's Principles of Internal Medicine, 17th ed.; McGraw Hill, New York, pp 628-634). Appropriate therapy for iron-deficiency anemia depends on its cause and severity, with oral iron preparations, parenteral iron formulations, and RBC transfusion as major conventional options. An ActRIIa polypeptide, or other activin-ActRIaI antagonist, could be used to treat chronic iron-deficiency anemias alone (see Example below in a clinical trial patient) or in combination with conventional therapeutic approaches, particularly to treat anemias of multifactorial origin.

Hypoproliferative anemias can result from primary dysfunction or failure of the bone marrow, instead of dysfunction secondary to inflammation, infection, or cancer progression. Prominent examples would be myelosuppression caused by cancer chemotherapeutic drugs or cancer radiation therapy. A broad review of clinical trials found that mild anemia can occur in 100% of patients after chemotherapy, while more severe anemia can occur in up to 80% of such patients (Groopman et al., 1999, J Natl Cancer Inst 91:1616-1634). Myelosuppressive drugs include: 1) alkylating agents such as nitrogen mustards (e.g., melphalan) and nitrosoureas (e.g., streptozocin); 2) antimetabolites such as folic acid antagonists (e.g., methotrexate), purine analogs (e.g., thioguanine), and pyrimidine analogs (e.g., gemcitabine); 3) cytotoxic antibotics such as anthracyclines (e.g., doxorubicin); 4) kinase inhibitors (e.g., gefitinib); 5) mitotic inhibitors such as taxanes (e.g., paclitaxel) and vinca alkaloids (e.g., vinorelbine); 6) monoclonal antibodies (e.g., rituximab); and 7) topoisomerase inhibitors (e.g., topotecan and etoposide). As demonstrated in a mouse model of chemotherapy-induced anemia (see Example below), an ActRIIa polypeptide, or other activin-ActRIIa antagonist, can be used to treat anemia caused by chemotherapeutic agents and/or radiation therapy.

Activin-ActRIIa antagonists (e.g., ActRIIa polypeptides) would also be appropriate for treating anemias of disordered RBC maturation, which are characterized in part by undersized (microcytic), oversized (macrocytic), misshapen, or abnormally colored (hypochromic) RBCs.

Patients may be treated with a dosing regimen intended to restore the patient to a target hemoglobin level, usually between about 10 g/dl and about 12.5 g/dl, and typically about 11.0 g/dl (see also Jacobs et al. (2000) Nephrol Dial Transplant 15, 15-19), although lower target levels may cause fewer cardiovascular or other side effects. Alternatively, hematocrit levels (percentage of the volume of a blood sample occupied by the cells) can be used as a measure for the condition of red blood cells. Hematocrit levels for healthy individuals range from 41 to 51% for adult males and from 35 to 45% for adult females. Target hematocrit levels are usually around 30-33%. Moreover, hemoglobin/hematocrit levels vary from person to person. Thus, optimally, the target hemoglobin/hematocrit level can be individualized for each patient.

The rapid effect on red blood cell levels of the activin-ActRIIa antagonists disclosed herein indicate that these agents act by a different mechanism than Epo. Accordingly, these antagonists may be useful for increasing red blood cell and hemoglobin levels in patients that do not respond well to Epo. For example, an activin-ActRIIa antagonist may be beneficial for a patient in which administering of a normal to increased (>300 IU/kg/week) dose of Epo does not result in the increase of hemoglobin level up to the target level. Patients with an inadequate Epo response are found for all types of anemia, but higher numbers of non-responders have been observed particularly frequently in patients with cancers and patients with end-stage renal disease. An inadequate response to Epo can be either constitutive (i.e. observed upon the first treatment with Epo) or acquired (e.g. observed upon repeated treatment with Epo).

The activin-ActRIIa antagonists may also be used to treat patients that are susceptible to adverse effects of Epo. The primary adverse effects of Epo are an excessive increase in the hematocrit or hemoglobin levels and polycythemia. Elevated hematocrit levels can lead to hypertension (more particularly aggravation of hypertension) and vascular thrombosis. Other adverse effects of Epo which have been reported, some of which related to hypertension, are headaches, influenza-like syndrome, obstruction of shunts, myocardial infarctions and cerebral convulsions due to thrombosis, hypertensive encephalopathy, and red cell blood cell applasia (Singibarti, (1994) J. Clin Investig 72(suppl 6), S36-S43; Horl et al. (2000) Nephrol Dial Transplant 15(suppl 4), 51-56; Delanty et al. (1997) Neurology 49, 686-689; Bunn (2002) N Engl J Med 346(7), 522-523).

As described in U.S. patent application Ser. No. 11/603,485, and in published patent applications WO 2008/100384 and WO/2007/062188, incorporated by reference herein, activin-ActRIIa antagonists can be used to promote bone growth and increase bone density. Thus, activin-ActRIIa antagonists may be particularly helpful to patients with a disorder that is associated with bone loss and anemia. Examples include renal diseases (especially chronic kidney disease and end-stage kidney disease), osteoporosis, cancer- and cancer treatments (especially the myelosuppressive therapies mentioned above, and the anti-estrogens discussed in WO 2008/100384 and WO/2007/062188), and inflammatory disorders, such as inflammatory bowel disease and rheumatoid arthritis.

7. Pharmaceutical Compositions

In certain embodiments, activin-ActRIIa antagonists (e.g., ActRIIa polypeptides) of the present invention are formulated with a pharmaceutically acceptable carrier. For example, an ActRIIa polypeptide can be administered alone or as a component of a pharmaceutical formulation (therapeutic composition). The subject compounds may be formulated for administration in any convenient way for use in human or veterinary medicine.

In certain embodiments, the therapeutic method of the invention includes administering the composition systemically, or locally as an implant or device. When administered, the therapeutic composition for use in this invention is, of course, in a pyrogen-free, physiologically acceptable form. Therapeutically useful agents other than the activin-ActRIIa antagonists which may also optionally be included in the composition as described above, may be administered simultaneously or sequentially with the subject compounds (e.g., ActRIIa polypeptides) in the methods of the invention.

Typically, activin-ActRIaI antagonists will be administered parenterally. Pharmaceutical compositions suitable for parenteral administration may comprise one or more ActRIIa polypeptides in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents. Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Further, the composition may be encapsulated or injected in a form for delivery to a target tissue site (e.g., bone marrow). In certain embodiments, compositions of the present invention may include a matrix capable of delivering one or more therapeutic compounds (e.g., ActRIIa polypeptides) to a target tissue site (e.g., bone marrow), providing a structure for the developing tissue and optimally capable of being resorbed into the body. For example, the matrix may provide slow release of the ActRIIa polypeptides. Such matrices may be formed of materials presently in use for other implanted medical applications.

The choice of matrix material is based on biocompatibility, biodegradability, mechanical properties, cosmetic appearance and interface properties. The particular application of the subject compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are non-biodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

In certain embodiments, methods of the invention can be administered for orally, e.g., in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of an agent as an active ingredient. An agent may also be administered as a bolus, electuary or paste.

In solid dosage forms for oral administration (capsules, tablets, pills, dragees, powders, granules, and the like), one or more therapeutic compounds of the present invention may be mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose, and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration include pharmaceutically acceptable emulsions, microemulsions, solutions, suspensions, syrups, and elixirs. In addition to the active ingredient, the liquid dosage forms may contain inert diluents commonly used in the art, such as water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor, and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming, and preservative agents.

Suspensions, in addition to the active compounds, may contain suspending agents such as ethoxylated isostearyl alcohols, polyoxyethylene sorbitol, and sorbitan esters, microcrystalline cellulose, aluminum metahydroxide, bentonite, agar-agar and tragacanth, and mixtures thereof.

The compositions of the invention may also contain adjuvants, such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption, such as aluminum monostearate and gelatin.

It is understood that the dosage regimen will be determined by the attending physician considering various factors which modify the action of the subject compounds of the invention (e.g., ActRIIa polypeptides). The various factors include, but are not limited to, the patient's red blood cell count, hemoglobin level or other diagnostic assessments, the desired target red blood cell count, the patient's age, sex, and diet, the severity of any disease that may be contributing to a depressed red blood cell level, time of administration, and other clinical factors. The addition of other known growth factors to the final composition may also affect the dosage. Progress can be monitored by periodic assessment of red blood cell and hemoglobin levels, as well as assessments of reticulocyte levels and other indicators of the hematopoietic process.

Experiments with primates and humans have demonstrated that effects of ActRIIa-Fc on red blood cell levels are detectable when the compound is dosed at intervals and amounts sufficient to achieve serum concentrations of about 100 ng/ml or greater, for a period of at least about 20 to 30 days. Dosing to obtain serum levels of 200 ng/ml, 500 ng/ml, 1000 ng/ml or greater for a period of at least 20 to 30 days may also be used. Bone effects can be observed at serum levels of about 200 ng/ml, with substantial effects beginning at about 1000 ng/ml or higher, over a period of at least about 20 to 30 days. Thus, if it is desirable to achieve effects on red blood cells while having little effect on bone, a dosing scheme may be designed to deliver a serum concentration of between about 100 and 1000 ng/ml over a period of about 20 to 30 days. In humans, serum levels of 200 ng/ml may be achieved with a single dose of 0.1 mg/kg or greater and serum levels of 1000 ng/ml may be achieved with a single dose of 0.3 mg/kg or greater. The observed serum half-life of the molecule is between about 20 and 30 days, substantially longer than most Fc fusion proteins, and thus a sustained effective serum level may be achieved, for example, by dosing with about 0.05 to 0.5 mg/kg on a weekly or biweekly basis, or higher doses may be used with longer intervals between dosings. For example, doses of 0.1 to 1 mg/kg might be used on a monthly or bimonthly basis.

In certain embodiments, the present invention also provides gene therapy for the in vivo production of ActRIIa polypeptides. Such therapy would achieve its therapeutic effect by introduction of the ActRIIa polynucleotide sequences into cells or tissues having the disorders as listed above. Delivery of ActRIIa polynucleotide sequences can be achieved using a recombinant expression vector such as a chimeric virus or a colloidal dispersion system. Preferred for therapeutic delivery of ActRIIa polynucleotide sequences is the use of targeted liposomes.

Various viral vectors which can be utilized for gene therapy as taught herein include adenovirus, herpes virus, vaccinia, or an RNA virus such as a retrovirus. The retroviral vector may be a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). A number of additional retroviral vectors can incorporate multiple genes. All of these vectors can transfer or incorporate a gene for a selectable marker so that transduced cells can be identified and generated. Retroviral vectors can be made target-specific by attaching, for example, a sugar, a glycolipid, or a protein. Preferred targeting is accomplished by using an antibody. Those of skill in the art will recognize that specific polynucleotide sequences can be inserted into the retroviral genome or attached to a viral envelope to allow target specific delivery of the retroviral vector containing the ActRIIa polynucleotide.

Alternatively, tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for ActRIIa polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. RNA, DNA and intact virions can be encapsulated within the aqueous interior and be delivered to cells in a biologically active form (see e.g., Fraley, et al., Trends Biochem. Sci., 6:77, 1981). Methods for efficient gene transfer using a liposome vehicle, are known in the art, see e.g., Mannino, et al., Biotechniques, 6:682, 1988. The composition of the liposome is usually a combination of phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Illustrative phospholipids include egg phosphatidylcholine, dipalmitoylphosphatidylcholine, and distearoylphosphatidylcholine. The targeting of liposomes is also possible based on, for example, organ-specificity, cell-specificity, and organelle-specificity and is known in the art.

EXEMPLIFICATION

The invention now being generally described, it will be more readily understood by reference to the following examples, which are included merely for purposes of illustration of certain embodiments and embodiments of the present invention, and are not intended to limit the invention.

EXAMPLE 1

ActRIIa-Fc Fusion Proteins

Applicants constructed a soluble ActRIIa fusion protein that has the extracellular domain of human ActRIIa fused to a human or mouse Fc domain with a minimal linker in between. The constructs are referred to as ActRIIa-hFc and ActRIIa-mFc, respectively.

ActRIIa-hFc is shown below as purified from CHO cell lines (SEQ ID NO: 7):

ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

EVTQPTSNIWTPKPP<u>TGGGTHTCPPCPAPELLGGPSVFLFPPKPKDTLMI</u>

<u>SRTPEVTCVVVDVSHEDPEVKFNWYVDGVEVHNAKTKPREEQYNSTYRVV</u>

<u>SVLTVLHQDWLNGKEYKCKVSNKALPVPIEKTISKAKGQPREPQVYTLPP</u>

<u>SREEMTKNQVSLTCLVKGFYPSDIAVEWESNGQPENNYKTTPPVLDSDGS</u>

<u>FFLYSKLTVDKSRWQQGNVFSCSVMHEALHNHYTQKSLSLSPGK</u>

The ActRIIa-hFc and ActRIIa-mFc proteins were expressed in CHO cell lines. Three different leader sequences were considered:
(i) Honey bee mellitin (HBML): MKFLVNVALVFMVVYI-SYIYA (SEQ ID NO: 8)
(ii) Tissue Plasminogen Activator (TPA): MDAMKRGLCCVLLLCGAVFVSP (SEQ ID NO: 9)
(iii) Native: MGAAAKLAFAVFLISCSSGA (SEQ ID NO: 10).

The selected form employs the TPA leader and has the following unprocessed amino acid sequence:

```
                                         (SEQ ID NO: 13)
MDAMKRGLCCVLLLCGAVFVSPGAAILGRSETQECLFFNANWEKDRTNQT

GVEPCYGDKDKRRHCFATWKNISGSIEIVKQGCWLDDINCYDRTDCVEKK

DSPEVYFCCCEGNMCNEKFSYFPEMEVTQPTSNPVTPKPPTGGGTHTCPP

CPAPELLGGPSVFLFPPKPKDTLMISRTPEVTCVVVDVSHEDPEVKFNWY

VDGVEVHNAKTKPREEQYNSTYRVVSVLTVLHQDWLNGKEYKCKVSNKAL

PVPIEKTISKAKGQPREPQVYTLPPSREEMTKNQVSLTCLVKGFYPSDIA

VEWESNGQPENNYKTTPPVLDSDGSFFLYSKLTVDKSRWQQGNVFSCSVM

HEALHNHYTQKSLSLSPGK
```

This polypeptide is encoded by the following nucleic acid sequence:

```
                                         (SEQ ID NO: 14)
ATGGATGCAATGAAGAGAGGGCTCTGCTGTGTGCTGCTGCTGTGTGGAGC

AGTCTTCGTTTCGCCCGGCGCCGCTATACTTGGTAGATCAGAAACTCAGG

AGTGTCTTTTTTTAATGCTAATTGGGAAAAAGACAGAACCAATCAAACTG

GTGTTGAACCGTGTTATGGTGACAAAGATAAACGGCGGCATTGTTTTGCT

ACCTGGAAGAATATTTCTGGTTCCATTGAATAGTGAAACAAGGTTGTTGG

CTGGATGATATCAACTGCTATGACAGGACTGATTGTGTAGAAAAAAAAGA

CAGCCCTGAAGTATATTTCTGTTGCTGTGAGGGCAATATGTGTAATGAAA

AGTTTTCTTATTTTCCGGAGATGGAAGTCACACAGCCCACTTCAAATCCA

GTTACACCTAAGCCACCCACCGGTGGTGGAACTCACACATGCCCACCGTG

CCCAGCACCTGAACTCCTGGGGGGACCGTCAGTCTTCCTCTTCCCCCCAA

AACCCAAGGACACCCTCATGATCTCCCGGACCCCTGAGGTCACATGCGTG

GTGGTGGACGTGAGCCACGAAGACCCTGAGGTCAAGTTCAACTGGTACGT

GGACGGCGTGGAGGTGCATAATGCCAAGACAAAGCCGCGGGAGGAGCAGT

ACAACAGCACGTACCGTGTGGTCAGCGTCCTCACCGTCCTGCACCAGGAC

TGGCTGAATGGCAAGGAGTACAAGTGCAAGGTCTCCAACAAAGCCCTCCC

AGTCCCCATCGAGAAAACCATCTCCAAAGCCAAAGGGCAGCCCCGAGAAC

CACAGGTGTACACCCTGCCCCCATCCCGGGAGGAGATGACCAAGAACCAG

GTCAGCCTGACCTGCCTGGTCAAAGGCTTCTATCCCAGCGACATCGCCGT

GGAGTGGGAGAGCAATGGGCAGCCGGAGAACAACTACAAGACCACGCCTC

CCGTGCTGGACTCCGACGGCTCCTTCTTCCTCTATAGCAAGCTCACCGTG

GACAAGAGCAGGTGGCAGCAGGGGAACGTCTTCTCATGCTCCGTGATGCA

TGAGGCTCTGCACAACCACTACACGCAGAAGAGCCTCTCCCTGTCTCCGG

GTAAATGAGAATTC
```

Both ActRIIa-hFc and ActRIIa-mFc were remarkably amenable to recombinant expression. As shown in FIG. 1, the protein was purified as a single, well-defined peak of protein. N-terminal sequencing revealed a single sequence of -ILGRS ETQE (SEQ ID NO: 11). Purification could be achieved by a series of column chromatography steps, including, for example, three or more of the following, in any order: protein A chromatography, Q sepharose chromatography, phe- nylsepharose chromatography, size exclusion chromatography, and cation exchange chromatography. The purification could be completed with viral filtration and buffer exchange. The ActRIIa-hFc protein was purified to a purity of >98% as determined by size exclusion chromatography and >95% as determined by SDS PAGE.

Figure 2B:
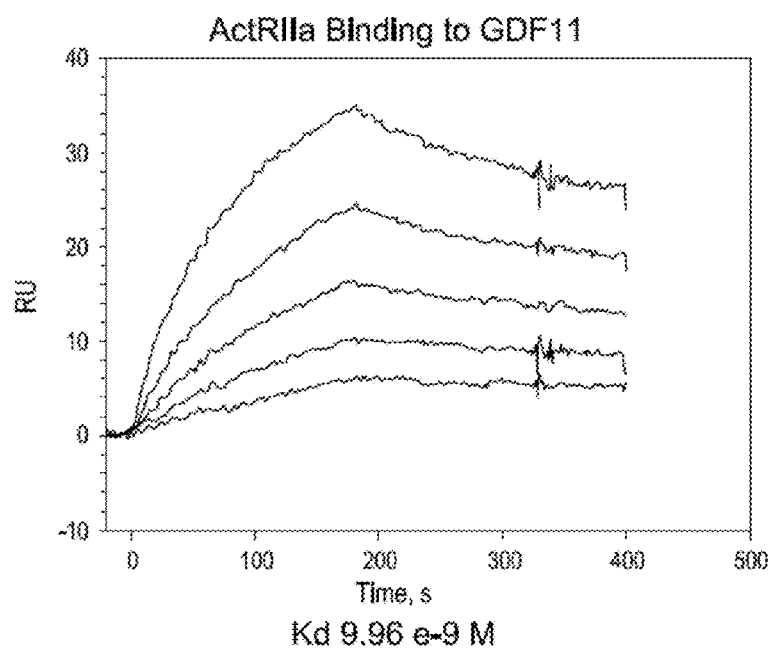
Figure 3A:
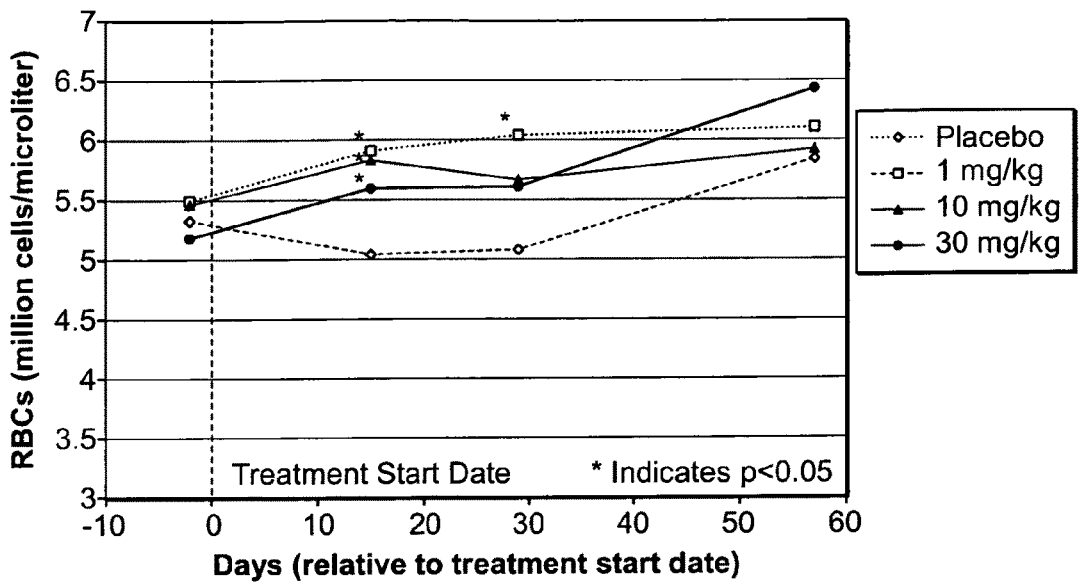
FIG. 3A shows red blood cell (RBC) counts.
Figure 3B:
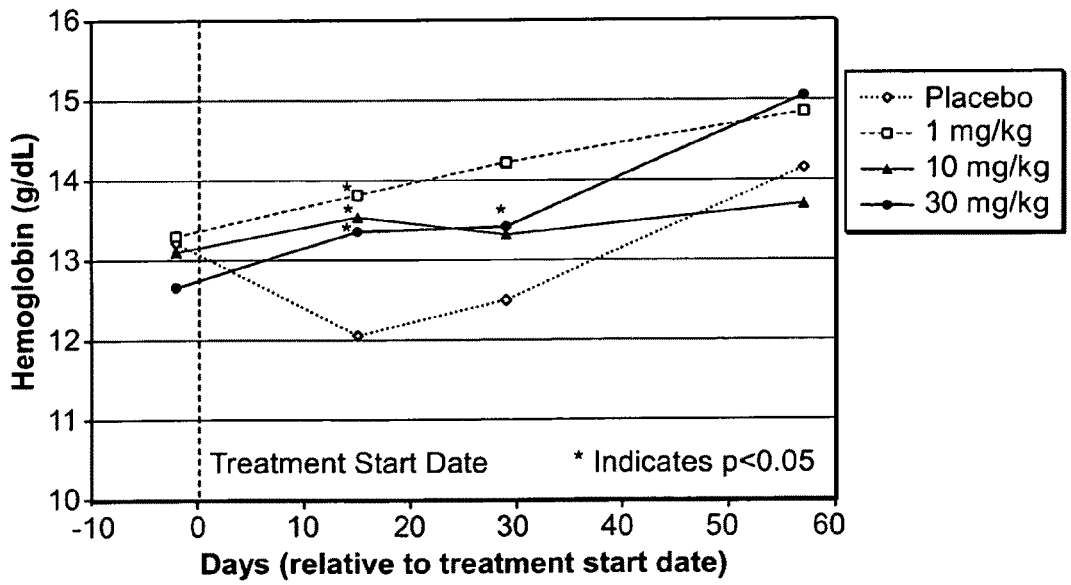
FIG. 3B shows hemoglobin levels. Statistical significance is relative to baseline for each treatment group. At day 57, two monkeys remained in each group.
Figure 4A:
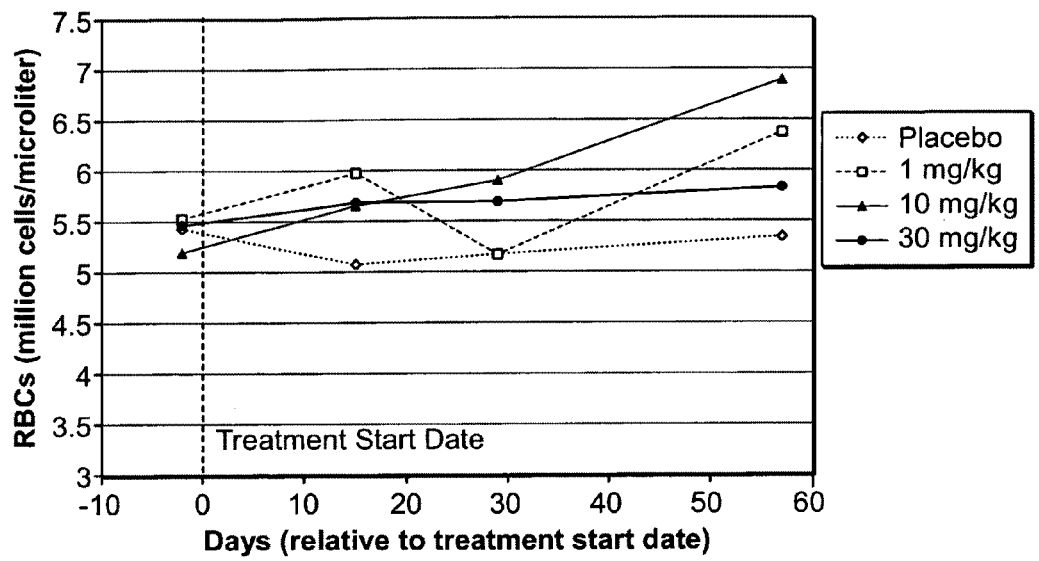
FIG. 4A shows red blood cell (RBC) counts.
Figure 4B:
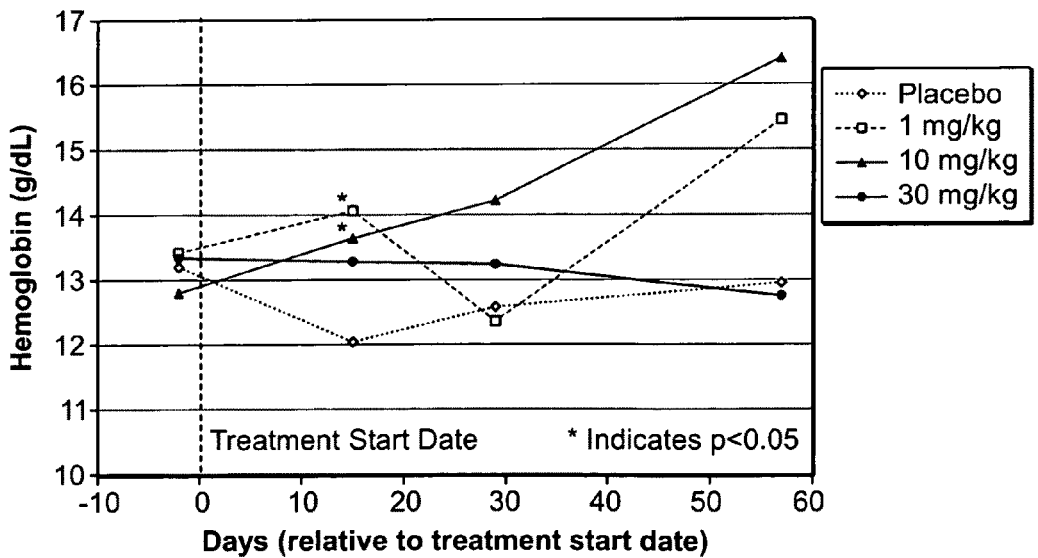
FIG. 4B shows hemoglobin levels. Statistical significance is relative to baseline for each treatment group. At day 57, two monkeys remained in each group.
Figure 5A:
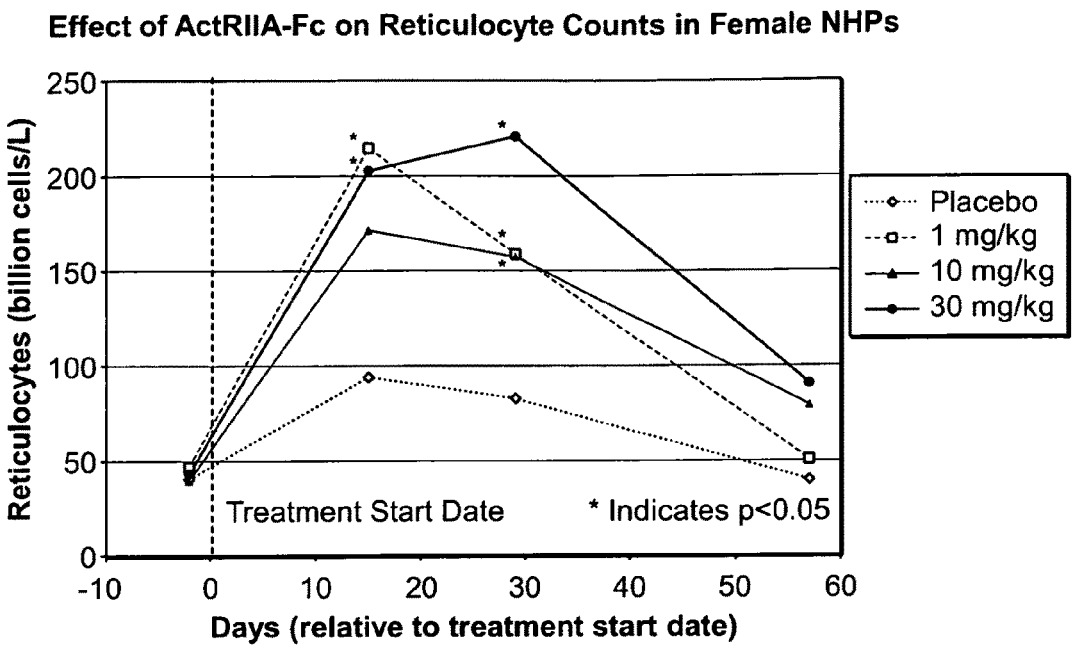
FIG. 5A shows absolute reticulocyte counts.
Figure 5B:
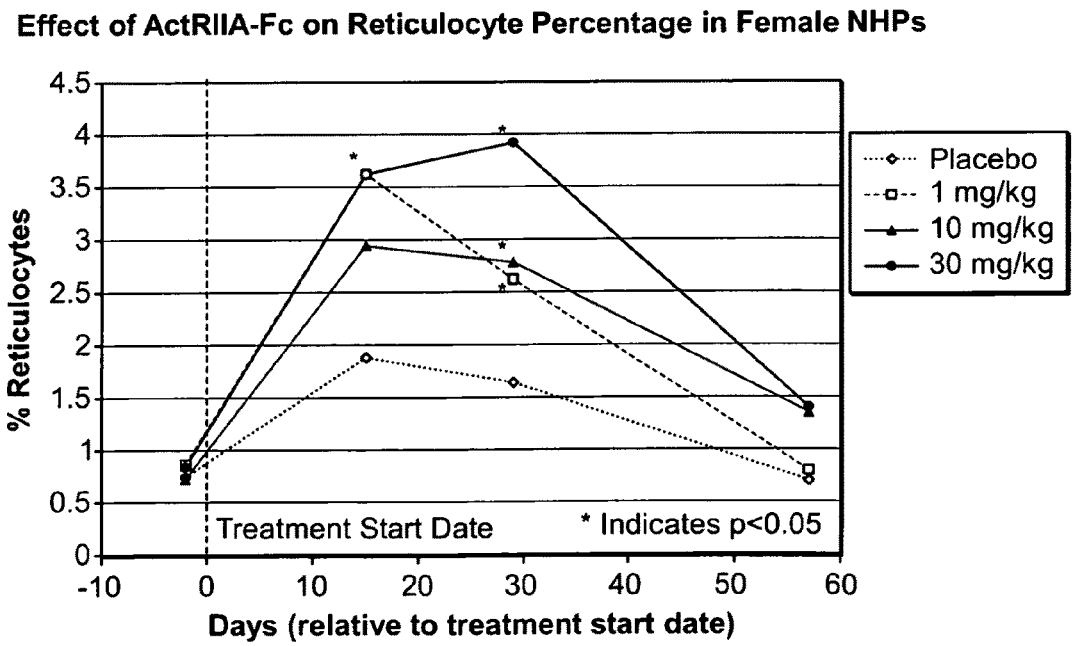
FIG. 5B shows the percentage of reticulocytes relative to RBCs. Statistical significance is relative to baseline for each group. At day 57, two monkeys remained in each group.
Figure 6A:
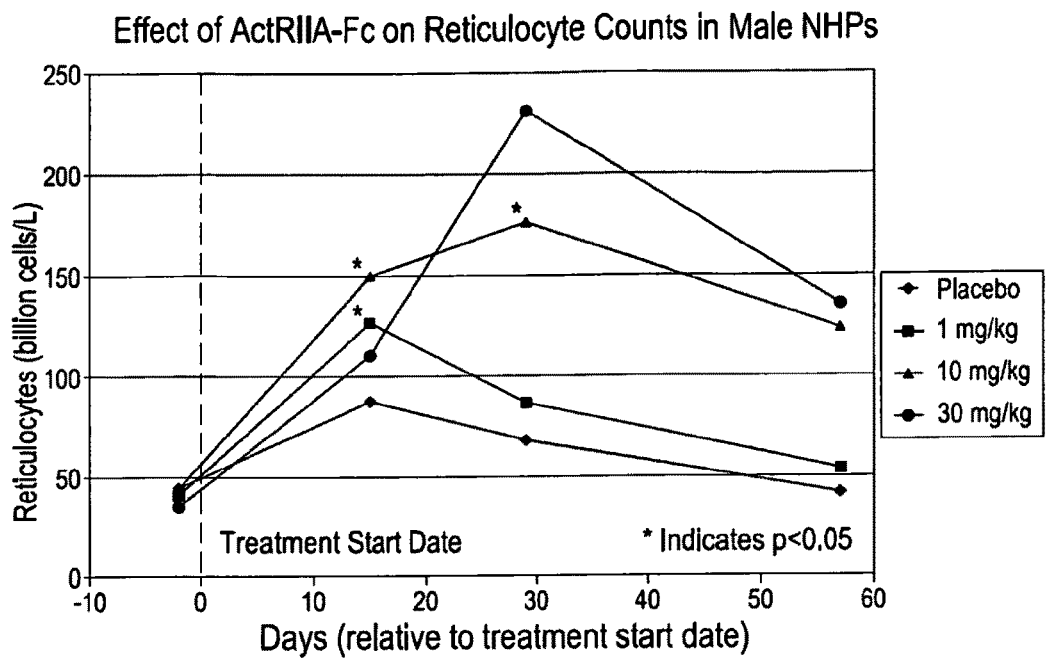
FIG. 6A shows absolute reticulocyte counts.
Figure 6B:
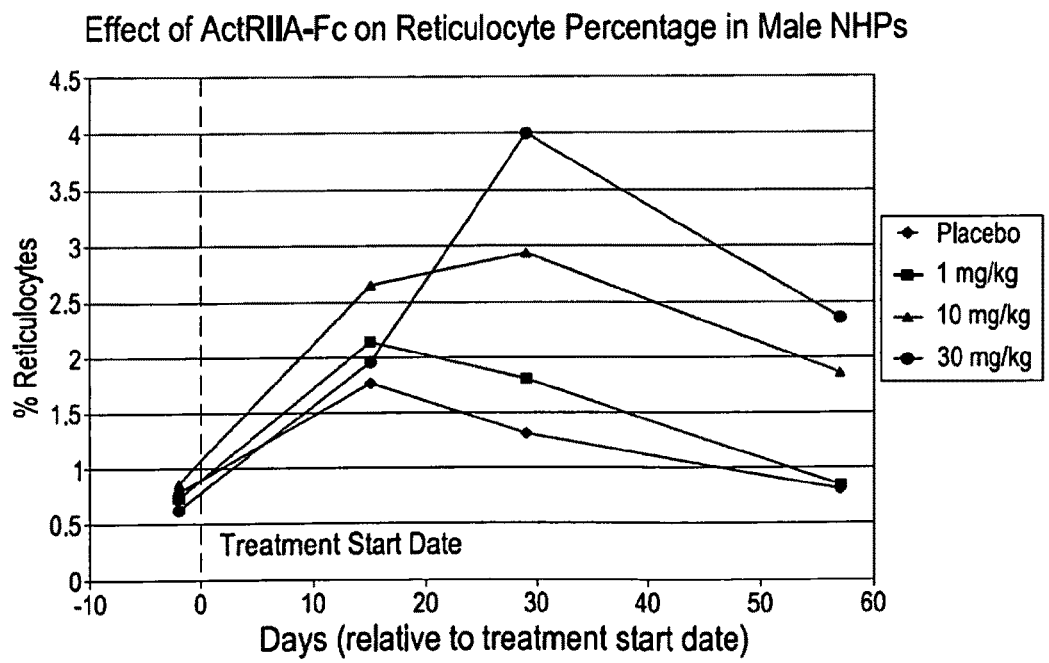
FIG. 6B shows the percentage of reticulocytes relative to RBCs. Statistical significance is relative to baseline for each group. At day 57, two monkeys remained in each group.

ActRIIa-hFc and ActRIIa-mFc showed a high affinity for ligands, particularly activin A. GDF-11 or Activin A ("ActA") were immobilized on a Biacore CM5 chip using standard amine coupling procedure. ActRIIa-hFc and ActRIIa-mFc proteins were loaded onto the system, and binding was measured. ActRIIa-hFc bound to activin with a dissociation constant ($K_D$) of $5 \times 10^{-12}$, and the protein bound to GDF11 with a $K_D$ of $9.96 \times 10^{-9}$. See FIG. 2. ActRIIa-mFc behaved similarly.

The ActRIIa-hFc was very stable in pharmacokinetic studies. Rats were dosed with 1 mg/kg, 3 mg/kg or 10 mg/kg of ActRIIa-hFc protein and plasma levels of the protein were measured at 24, 48, 72, 144 and 168 hours. In a separate study, rats were dosed at 1 mg/kg, 10 mg/kg or 30 mg/kg. In rats, ActRIIa-hFc had an 11-14 day serum half life and circulating levels of the drug were quite high after two weeks (11 μg/ml, 110 μg/ml or 304 μg/ml for initial administrations of 1 mg/kg, 10 mg/kg or 30 mg/kg, respectively.) In cynomolgus monkeys, the plasma half life was substantially greater than 14 days and circulating levels of the drug were 25 μg/ml, 304 μg/ml or 1440 μg/ml for initial administrations of 1 mg/kg, 10 mg/kg or 30 mg/kg, respectively. Preliminary results in humans suggests that the serum half life is between about 20 and 30 days.

EXAMPLE 2

Characterization of an ActRIIa-hFc Protein

ActRIIa-hFc fusion protein was expressed in stably transfected CHO-DUKX B11 cells from a pAID4 vector (SV40 ori/enhancer, CMV promoter), using a tissue plasminogen leader sequence of SEQ ID NO:9. The protein, purified as described above in Example 1, had a sequence of SEQ ID NO:7. The Fc portion is a human IgG1 Fc sequence, as shown in SEQ ID NO:7. Sialic acid analysis showed that the protein contained, on average, between about 1.5 and 2.5 moles of sialic acid per molecule of ActRIIa-hFc fusion protein.

This purified protein showed a remarkably long serum half-life in all animals tested, including a half-life of 25-32 days in human patients (see Example 6, below). Additionally, the CHO cell expressed material has a higher affinity for activin B ligand than that reported for an ActRIIa-hFc fusion protein expressed in human 293 cells (del Re et al., J Biol Chem. 2004 Dec. 17; 279(51):53126-35.) Additionally, the use of the tPa leader sequence provided greater production than other leader sequences and, unlike ActRIIa-Fc expressed with a native leader, provided a highly pure N-terminal sequence. Use of the native leader sequence resulted in two major species of ActRIIa-Fc, each having a different N-terminal sequence.

EXAMPLE 3

ActRIIa-hFc Increases Red Blood Cell Levels in Non-Human Primates

The study employed four groups of five male and five female cynomolgus monkeys each, with three per sex per group scheduled for termination on Day 29, and two per sex per group scheduled for termination on Day 57. Each animal was administered the vehicle (Group I) or ActRIIa-Fc at doses of 1, 10, or 30 mg/kg (Groups 2, 3 and 4, respectively) via intravenous (IV) injection on Days 1, 8, 15 and 22. The dose volume was maintained at 3 mL/kg. Various measures of red blood cell levels were assessed two days prior to the first administration and at days 15, 29 and 57 (for the remaining two animals) after the first administration.

The ActRIIa-hFc caused statistically significant increases in mean red blood cell parameters (red blood cell count [RBC], hemoglobin [HGB], and hematocrit [HCT]) for males and females, at all dose levels and time points throughout the study, with accompanying elevations in absolute and relative reticulocyte counts (ARTC; RTC). See FIGS. 3-6.

Statistical significance was calculated for each treatment group relative to the mean for the treatment group at baseline.

Notably, the increases in red blood cell counts and hemoglobin levels are roughly equivalent in magnitude to effects reported with erythropoietin. The onset of these effects is more rapid with ActRIIa-Fc than with erythropoietin.

Similar results were observed with rats and mice.

EXAMPLE 4

ActRIIa-hFc Increases Red Blood Cell Levels and Markers of Bone Formation in Human Patients The ActRIIa-hFc fusion protein described in Example 1 was administered to human patients in a randomized, double-blind, placebo-controlled study that was conducted to evaluate, primarily, the safety of the protein in healthy, postmenopausal women. Forty-eight subjects were randomized in cohorts of 6 to receive either a single dose of ActRIIa-hFc or placebo (5 active: 1 placebo). Dose levels ranged from 0.01 to 3.0 mg/kg intravenously (IV) and 0.03 to 0.1 mg/kg subcutaneously (SC). All subjects were followed for 120 days. In addition to pharmacokinetic (PK) analyses, the biologic activity of ActRIIa-hFc was also assessed by measurement of biochemical markers of bone formation and resorption, and FSH levels.

To look for potential changes, hemoglobin and RBC numbers were examined in detail for all subjects over the course of the study and compared to the baseline levels. Platelet counts were compared over the same time as the control. There were no clinically significant changes from the baseline values over time for the platelet counts.

Figure 7:
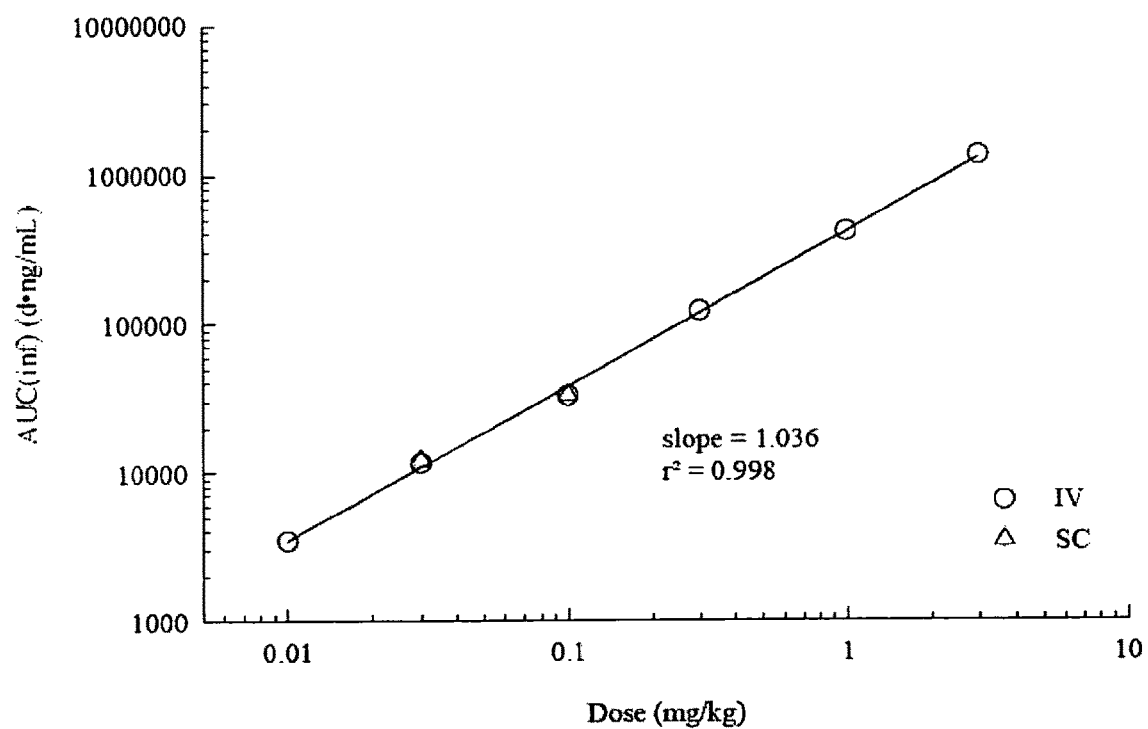
FIG. 7 shows results from the human clinical trial described in Example 5, where the area-under-curve (AUC) and administered dose of ActRIIa-hFc have a linear correlation, regardless of whether ActRIIa-hFc was administered intravenously (IV) or subcutaneously (SC).
Figure 8:
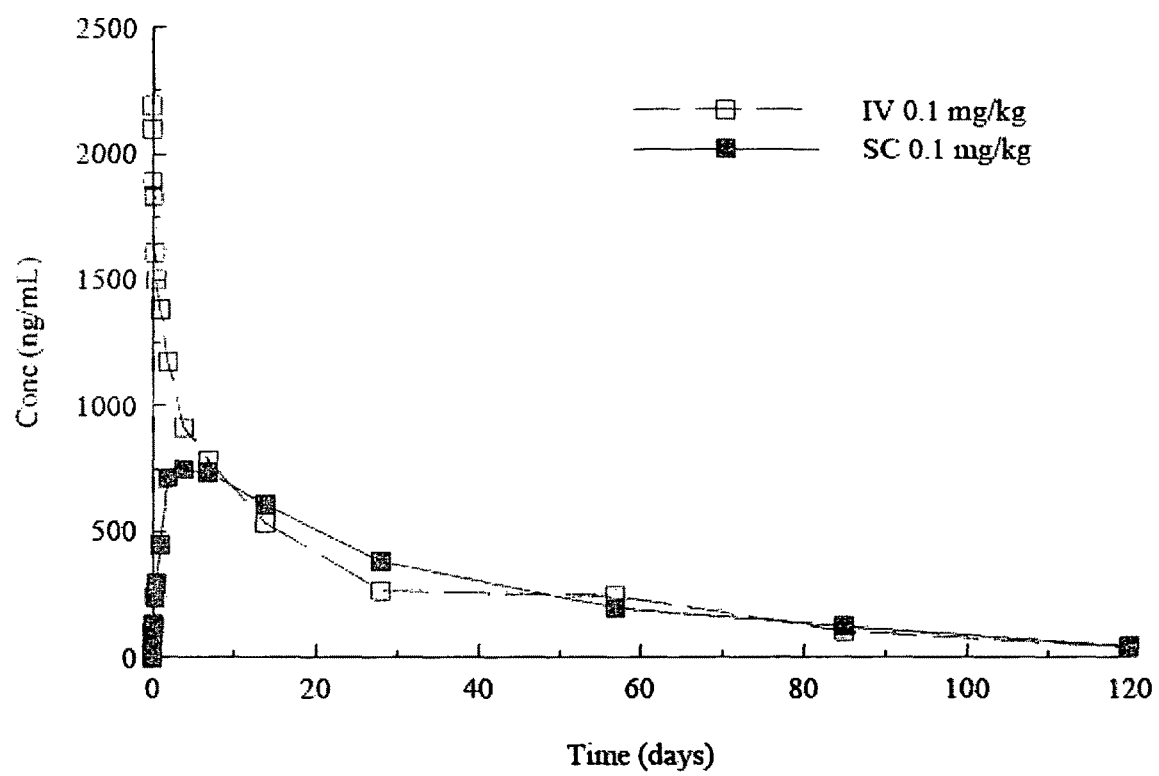
FIG. 8 shows a comparison of serum levels of ActRIIa-hFc in patients administered IV or SC.
Figure 9:
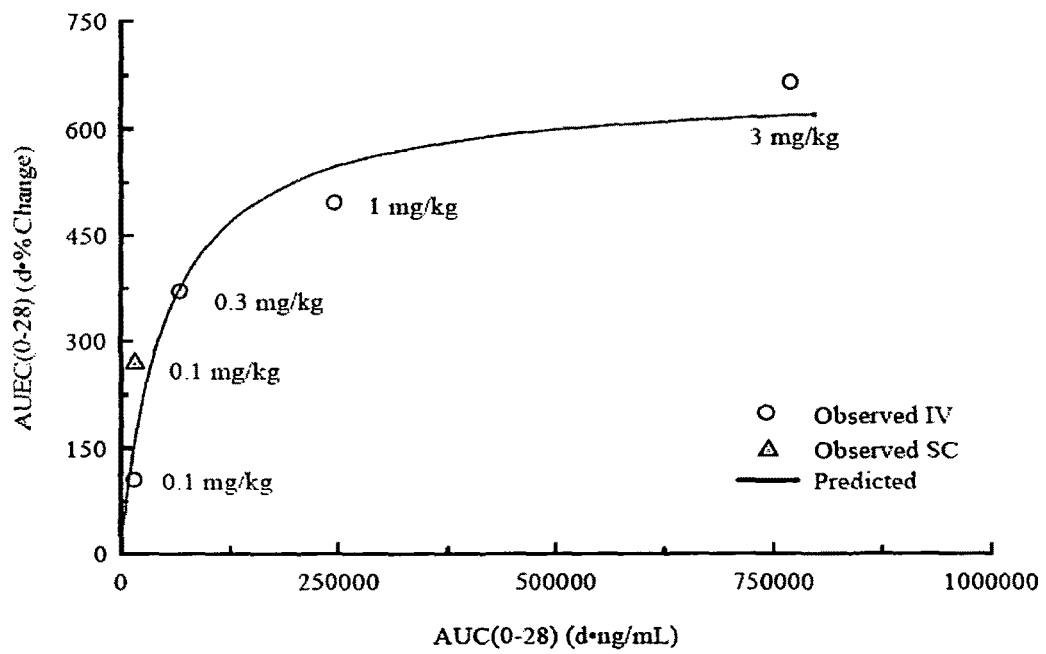
FIG. 9 shows bone alkaline phosphatase (BAP) levels in response to different dose levels of ActRIIa-hFc. BAP is a marker for anabolic bone growth.
Figure 10:
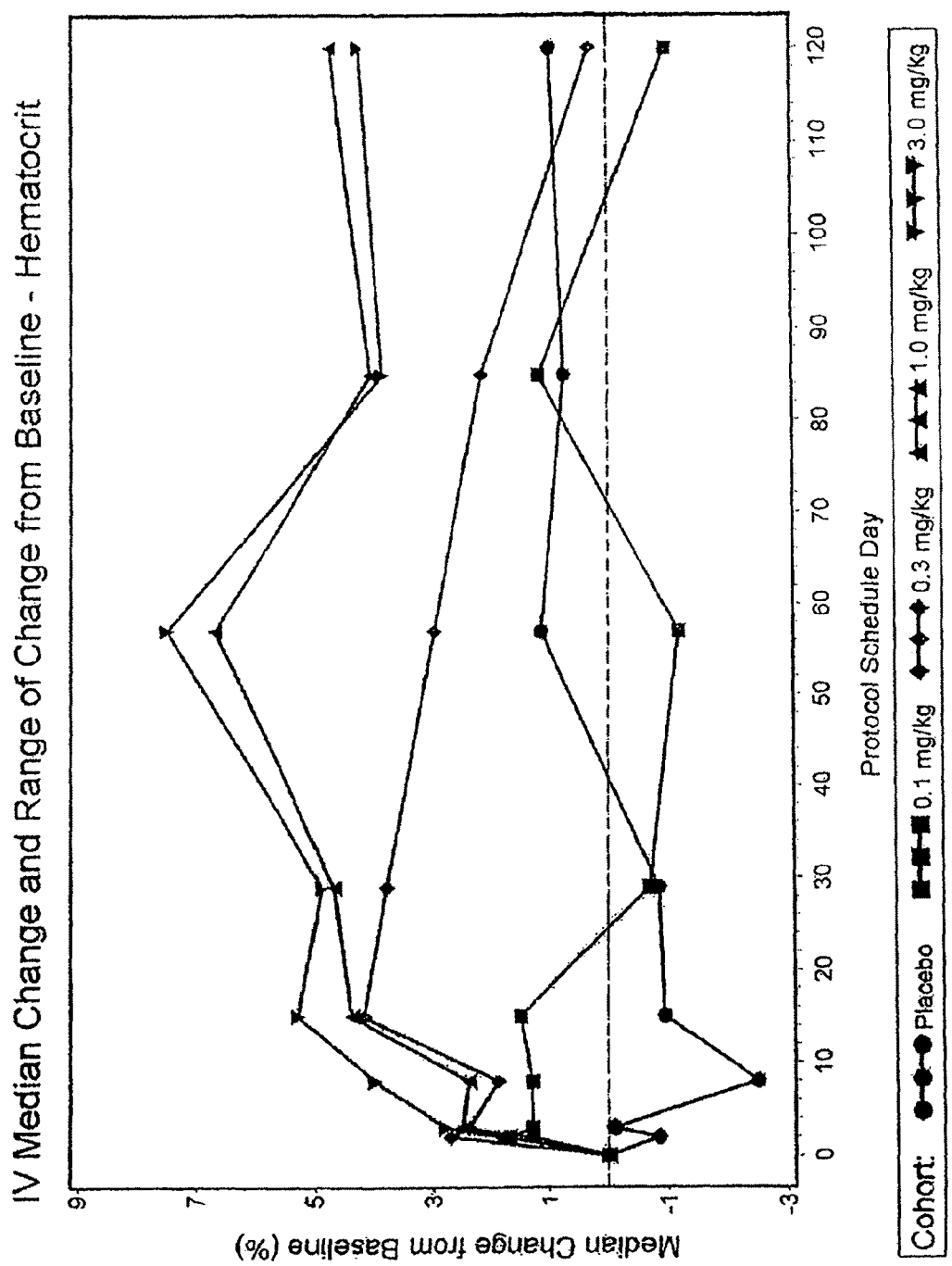
FIG. 10 depicts the median change from baseline of hematocrit levels from the human clinical trial described in Example 5. ActRIIa-hFc was administered intravenously (IV) at the indicated dosage.
Figure 11:
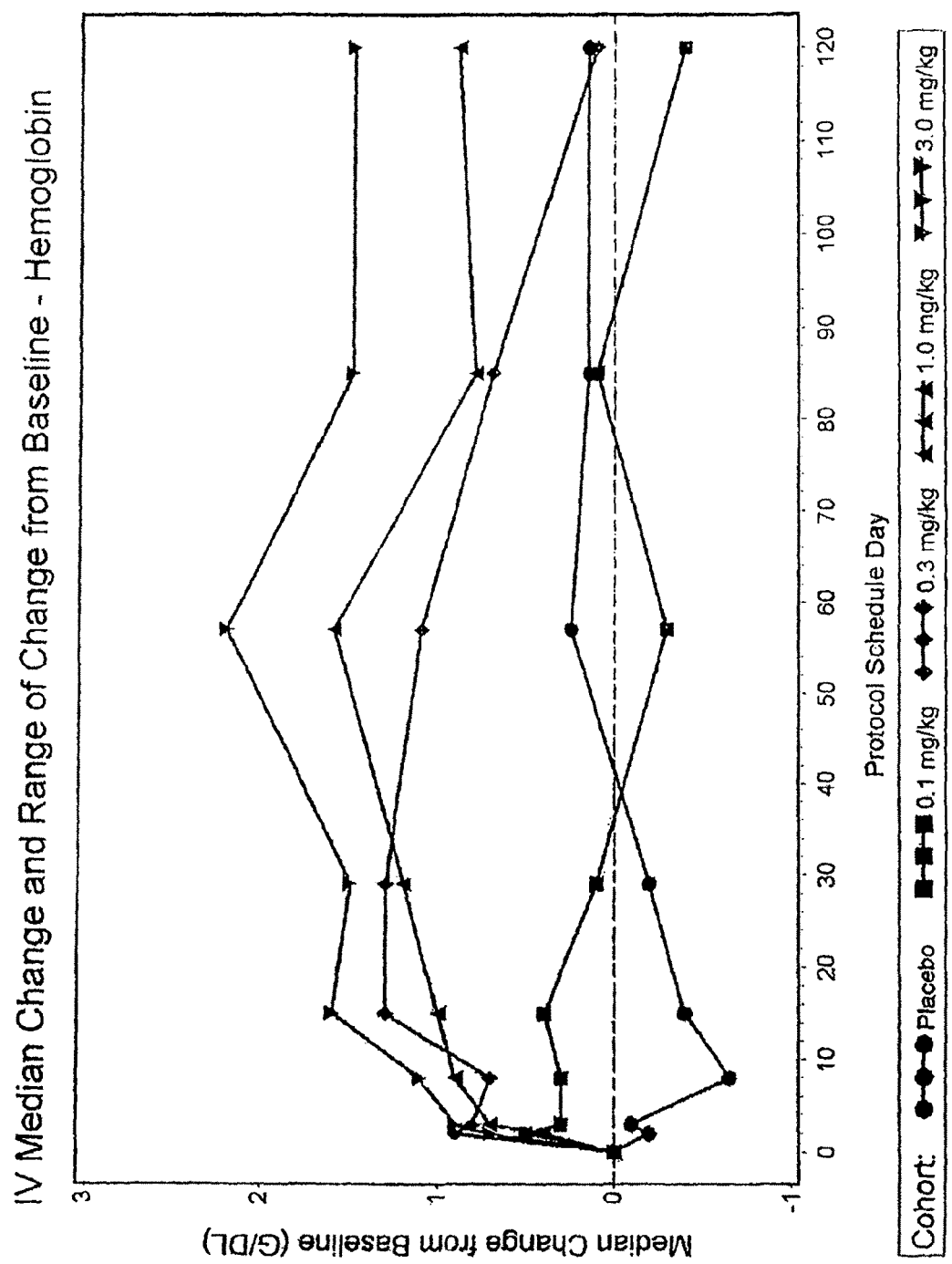
FIG. 11 depicts the median change from baseline of hemoglobin levels from the human clinical trial described in Example 5. ActRIIa-hFc was administered intravenously (IV) at the indicated dosage.
Figure 12:
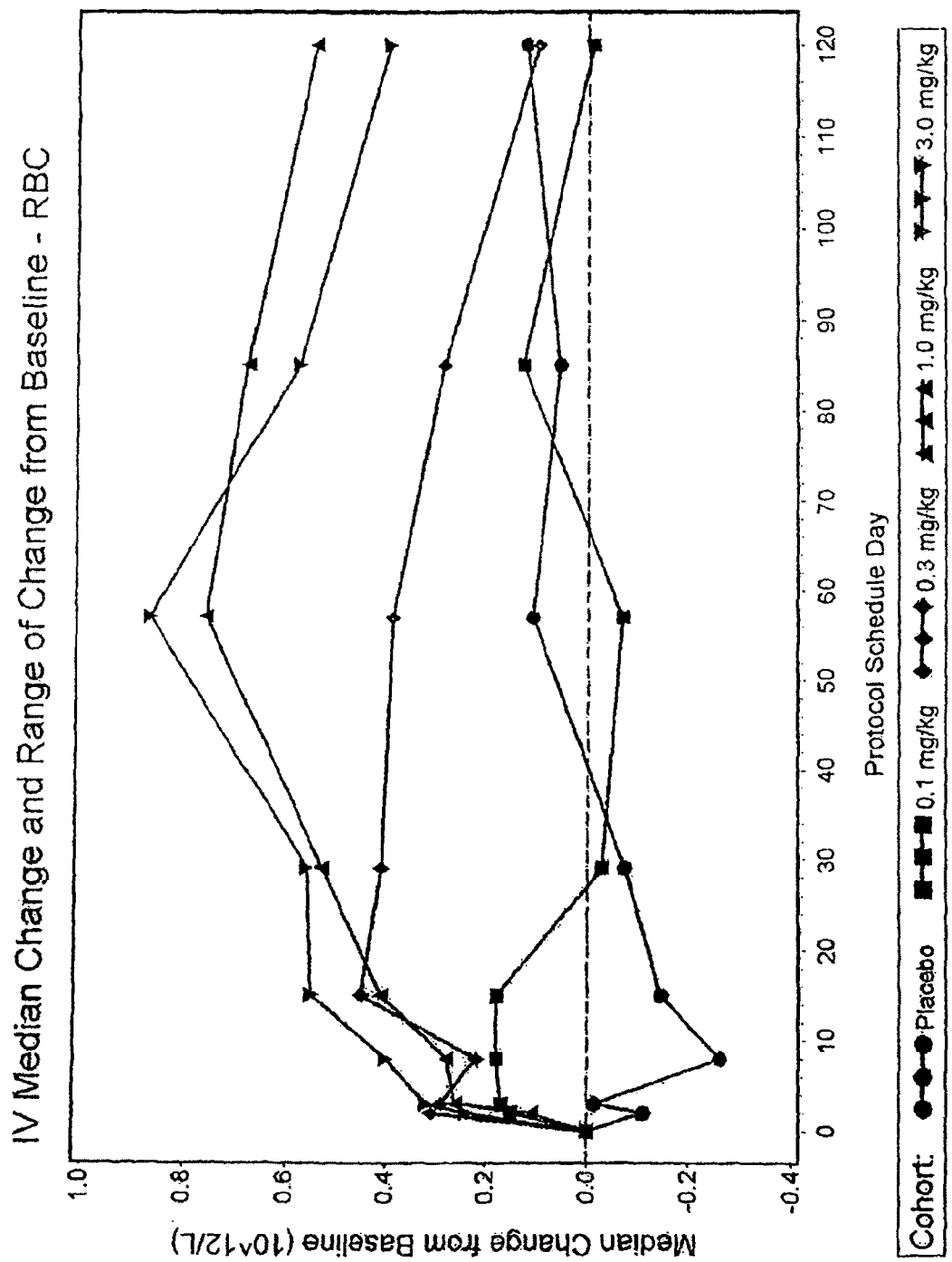
FIG. 12 depicts the median change from baseline of RBC (red blood cell) count from the human clinical trial described in Example 5. ActRIIa-hFc was administered intravenously (IV) at the indicated dosage.
Figure 13:
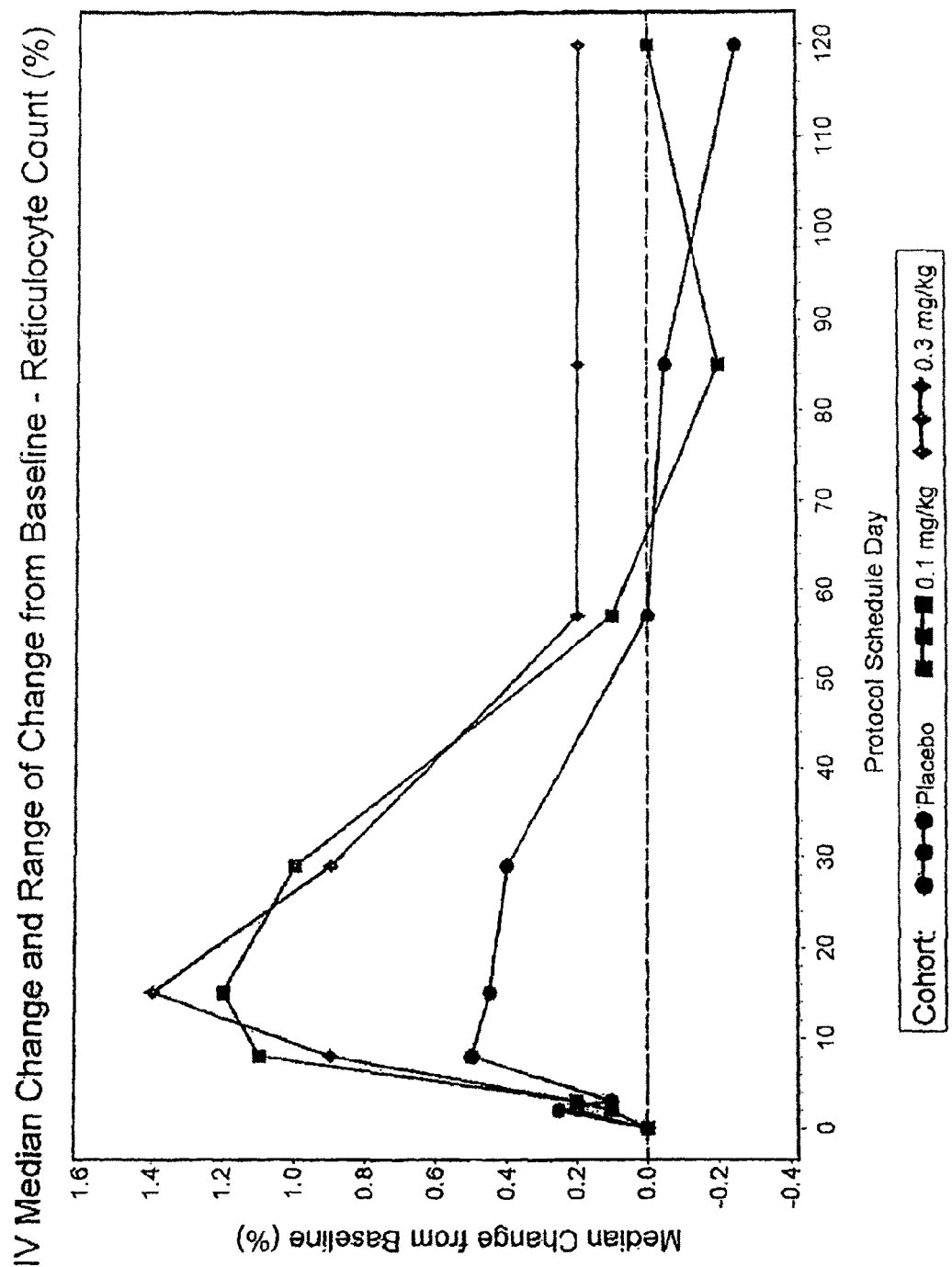
FIG. 13 depicts the median change from baseline of reticulocyte count from the human clinical trial described in Example 5. ActRIIa-hFc was administered intravenously (IV) at the indicated dosage.

PK analysis of ActRIIa-hFc displayed a linear profile with dose, and a mean half-life of approximately 25-32 days. The area-under-curve (AUC) for ActRIIa-hFc was linearly related to dose, and the absorption after SC dosing was essentially complete (see FIGS. 7 and 8). These data indicate that SC is a desirable approach to dosing because it provides equivalent bioavailability and serum-half life for the drug while avoiding the spike in serum concentrations of drug associated with the first few days of IV dosing (see FIG. 8). ActRIIa-hFc caused a rapid, sustained dose-dependent increase in serum levels of bone-specific alkaline phosphatase (BAP), which is a marker for anabolic bone growth, and a dose-dependent decrease in C-terminal type 1 collagen telopeptide and tartrate-resistant acid phosphatase 5b levels, which are markers for bone resorption. Other markers, such as P1NP showed inconclusive results. BAP levels showed near saturating effects at the highest dosage of drug, indicating that half-maximal effects on this anabolic bone biomarker could be achieved at a dosage of 0.3 mg/kg, with increases ranging up to 3 mg/kg. Calculated as a relationship of pharmacodynamic effect to AUC for drug, the EC50 is 51,465 (day*ng/ml). See FIG. 9. These bone biomarker changes were sustained for approximately 120 days at the highest dose levels tested. There was also a dose-dependent decrease in serum FSH levels consistent with inhibition of activin.

Overall, there was a very small non-drug related reduction in hemoglobin over the first week of the study probably related to study phlebotomy in the 0.01 and 0.03 mg/kg groups whether given IV or SC. The 0.1 mg/kg SC and IV hemoglobin results were stable or showed modest increases by Day 8-15. At the 0.3 mg/kg IV dose level there was a clear increase in HGB levels seen as early as Day 2 and often peaking at Day 15-29 that was not seen in the placebo subjects. At the 1.0 mg/kg IV dose and the 3.0 mg/kg IV dose, mean increases in hemoglobin of greater than 1 g/dl were observed in response to the single dose, with corresponding increases in RBC counts and hematocrit. These hematologic parameters peaked at about 60 days after the dose and substantial decrease by day 120. This indicates that dosing for the purpose of increasing red blood cell levels may be more effective if done at intervals less than 120 days (i.e., prior to return to baseline), with dosing intervals of 90 days or less or 60 days or less may be desirable. For a summary of hematological changes, see FIGS. 10-13.

Overall, ActRIIa-hFc showed a dose-dependent effect on red blood cell counts and reticulocyte counts, and a dose-dependent effect on markers of bone formation.

EXAMPLE 5

Treatment of an Anemic Patient with ActRIIa-hFc

A clinical study was designed to treat patients with multiple doses of ActRIIa-hFc, at 30 dose levels of 0.1 mg/kg, 0.3 mg/kg and 1.0 mg/kg, with dosing every thirty days. Normal healthy patients in the trial exhibited an increase in hemoglobin and hematocrit that is consistent with the increases seen in the Phase I clinical trial reported in Example 4, except that, in some instances, the hemoglobin and hematocrit were elevated beyond the normal range. An anemic patient with hemoglobin of approximately 7.5 also received two doses at the 1 mg/kg level, resulting in a hemoglobin level of approximately 10.5 after two months. The patient's anemia was a microcytic anemia, thought to be caused by chronic iron deficiency.

EXAMPLE 6

ActRIIa-mFc Increases Red Blood Cell Levels in Mice by Stimulation of Splenic Red Blood Cell Release In this study the effects of the in vivo administration of ActRIIa-mFc on the frequency of hematopoietic progenitors in bone marrow and spleen was analyzed. One group of mice was injected with PBS as a control and a second group of mice administered two doses of ActRIIa-mFc at 10 mg/kg and both groups sacrificed after 8 days. Peripheral blood was used to perform complete blood counts and femurs and spleens were used to perform in vitro clonogenic assays to assess the lymphoid, erythroid and myeloid progenitor cell content in each organ. In the peripheral blood a significant increase in the red blood cell and hemoglobin content was seen in compound treated mice. In the femurs there was no difference in the nucleated cell numbers or progenitor content between the control and treated groups. In the spleens, the compound treated group experienced a statistically significant increase in the nucleated cell number before red blood cell lysis and in the mature erythroid progenitor (CFU-E) colony number per dish, frequency and total progenitor number per spleen. In addition, and increase was seen in the number of myeloid (CFU-GM), immature erythroid (BFU-E) and total progenitor number per spleen.

Animals:

Sixteen BDF1 female mice 6-8 weeks of age were used in the study. Eight mice were injected subcutaneously with test compound ActRIIa-mFc at days 1 and 3 at a dose of 10 mg/kg and eight mice were injected subcutaneously with vehicle control, phosphate buffered saline (PBS), at a volume of 100 µL per mouse. All mice were sacrificed 8 days after first injection in accordance with the relevant Animal Care Guidelines. Peripheral blood (PB) samples from individual animals were collected by cardiac puncture and used for complete blood counts and differential (CBC/Diff). Femurs and spleens were harvested from each mouse.

Tests performed:

CBC/Diff Counts

PB from each mouse was collected via cardiac puncture and placed into the appropriate microtainer tubes. Samples were sent to CLV for analysis on a CellDyn 3500 counter.

Clonogenic Assays

Clonogenic progenitors of the myeloid, erythroid and lymphoid lineages were assessed using the in vitro methylcellulose-based media systems described below.

Mature Erythroid Progenitors:

Clonogenic progenitors of the mature erythroid (CFU-E) lineages were cultured in MethoCult™ 3334, a methylcellulose-based medium containing recombinant human (rh) Erythropoietin (3 U/mL).

Lymphoid Projenitors:

Clonogenic progenitors of the lymphoid (CFU-pre-B) lineage were cultured in MethoCult® 3630, a methylcellulose-based medium containing rh Interleukin 7 (10 ng/mL).

Myeloid and Immature Erythroid Progenitors:

Clonogenic progenitors of the granulocyte-monocyte (CFU-GM), erythroid (BFU-E) and multipotential (CFU-GEMM) lineages were cultured in MethoCult™ 3434, a methylcellulose-based medium containing recombinant murine (rm) Stem Cell Factor (50 ng/mL), rh Interleukin 6 (10 ng/mL), rm Interleukin 3 (10 ng/mL) and rh Erythropoietin (3 U/mL).

Methods:

Mouse femurs and spleens were processed by standard protocols. Briefly, bone marrow was obtained by flushing the femoral cavity with Iscove's Modified Dulbecco's Media containing 2% fetal bovine serum (IMDM 2% FBS) using a 21 gauge needle and 1 cc syringe. Spleen cells were obtained by crushing spleens through a 70 µM filter and rinsing the filter with IMDM 2% FBS. Nucleated cell counts in 3% glacial acetic acid were then performed on the single cells suspensions using a Neubauer counting chamber so that the total cells per organ could be calculated. To remove contaminating red blood cells, total spleen cells were then diluted with 3 times the volume of ammonium chloride lysis buffer and incubated on ice 10 minutes. The cells were then washed and resuspended in IMDM 2% FBS and a second cell count were performed to determine the cell concentration of cells after lysis.

Cell stocks were made and added to each methylcellulose-based media formulation to obtain the optimal plating concentrations for each tissue in each media formulation. Bone marrow cells were plated at $1\times10^5$ cells per dish in MethoCult™ 3334 to assess mature erythroid progenitors, $2\times10^5$ cells per dish in MethoCult™ 3630 to assess lymphoid progenitors and $3\times10^4$ cells per dish in MethoCult™ 3434 to assess immature erythroid and myeloid progenitors. Spleen cells were plated at $4\times10^5$ cells per dish in MethoCult™ 3334 to assess mature erythroid progenitors, $4\times10^5$ cells per dish in MethoCult™ 3630 to assess lymphoid progenitors and $2\times10^5$ cells per dish in MethoCult™ 3434 to assess immature erythroid and myeloid progenitors. Cultures plated in triplicate dishes were incubated at 37° C., 5% CO2 until colony enumeration and evaluation was performed by trained personnel. Mature erythroid progenitors were cultured for 2 days, lymphoid progenitors were cultured for 7 days and mature erythroid and myeloid progenitors were cultured for 12 days.

Analysis:

The mean+/−1 standard deviation was calculated for the triplicate cultures of the clonogenic assays and for the control and treatment groups for all data sets.

Frequency of colony forming cells (CFC) in each tissue was calculated as follows:

Cells plated per dish

Mean CFC scored per dish

Total CFC per femur or spleen was calculated as follows:

Total CFC scored x nucleated cell count per femur or spleen (following RBC lysis)

Number of nucleated cells cultured

Standard t-tests were performed to assess if there was a differences in the mean number of cells or hematopoietic progenitors between the PBS control mice and compound treated mice. Due to the potential subjectivity of colony enumeration, a p value of less than 0.01 is deemed significant. Mean values (+/−SD) for each group are shown in the tables below.

TABLE

| | Hematologic Parameters | | | |
|---|---|---|---|---|
| Treatment Group | White Blood Cells ($\times10^9$/L) | Red Blood Cells ($\times10^9$/L) | Hemoglobin (g/L) | Hematocrit (L/L) |
| PBS (n = 8) | 6.37 +/− 2.83 | 10.9 +/− 0.7 | 154.5 +/− 5.9 | 0.506 +/− 0.029 |
| ActRIIa-mFc (n = 8) | 8.92 +/− 3.69 | 11.8 +/− 0.3* | 168.3 +/− 4.3** | 0.532 +/− 0.014 |

*= p < 0.01
**= p < 0.0005

TABLE

| | CFC From Femur and Spleen | | | |
|---|---|---|---|---|
| Treatment Group | Total CFC per Femur | Total CFC per Spleen | Total CFU-E per Femur | Total CFU-E per Spleen |
| PBS (n = 8) | 33437 +/− 7118 | 4212 +/− 1148 | 27185 +/− 12893 | 6743 +/− 1591 |
| ActRIIa-mFc (n = 8) | 31068 +/− 8024 | 6816 +/− 1516* | 18118 +/− 6672 | 27313 +/− 11790 |

*= p < 0.005
**= p < 0.0001

Treatment of mice with ActRIIa-mFc resulted in significant increases in a number of hematopoietic parameters. In the peripheral blood a significant increase in the red blood cell and hemoglobin content was seen in compound treated mice. In the femurs there was no difference in the nucleated cell numbers or progenitor content between the control and treated groups. In the spleens, the compound treated group experienced a statistically significant increase in the nucleated cell number before red blood cell lysis and in the mature erythroid progenitor (CFU-E) colony number per dish, frequency and total progenitor number per spleen. In addition, an increase was seen in the number of myeloid (CFU-GM), immature erythroid (BFU-E) and total progenitor number per spleen.

EXAMPLE 7

Alternative ActRIIa-Fc Proteins

A variety of ActRIIa variants that may be used according to the methods described herein are described in the International Patent Application published as WO2006/012627 (see e.g., pp. 55-58), incorporated herein by reference in its entirety. An alternative construct may have a deletion of the C-terminal tail (the final 15 amino acids of the extracellular domain of ActRIIa. The sequence for such a construct is presented below (Fc portion underlined)(SEQ ID NO: 12):

ILGRSETQECLFFNANWEKDRTNQTGVEPCYGDKDKRRHCFATWKNISGS

IEIVKQGCWLDDINCYDRTDCVEKKDSPEVYFCCCEGNMCNEKFSYFPEM

<u>TGGGTHTCPPCPAPELLGGPSVFLFPPKPKDTLMISRTPEVTCVVVDVSH</u>

<u>EDPEVKFNWYVDGVEVHNAKTKPREEQYNSTYRVVSVLTVLHQDWLNGKE</u>

<u>YKCKVSNKALPVPIEKTISKAKGQPREPQVYTLPPSREEMTKNQVSLTCL</u>

<u>VKGFYPSDIAVEWESNGQPENNYKTTPPVLDSDGSFFLYSKLTVDKSRWQ</u>

<u>QGNVFSCSVMHEALHNHYTQKSLSLSPGK</u>

EXAMPLE 8

Effect of ActRIIA-mFc on Chemotherapy-Induced Anemia in Mice

Applicants investigated the effect of ActRIIA-mFc on chemotherapy-induced anemia in mice. In the first of two studies, 6-week-old female C57BL/6 mice were treated with a single dose of ActRIIA-mFc (10 mg/kg, s.c.) or vehicle (phosphate-buffered saline) 3 days before a single dose of the chemotherapeutic paclitaxel (20 mg/kg, i.p.). Blood samples were collected before chemotherapy and then 3, 7, and 14 days (n=6 per cohort per time point) after paclitaxel. ActRIIA-mFc prevented the decline in hematocrit level otherwise observed after paclitaxel (FIG. 15), and similar effects were observed for hemoglobin concentration and RBC count. In a second study, 6-week-old female C57BL/6 mice were given a varying number of ActRIIA-mFc doses (10 mg/kg, s.c.), or vehicle (PBS), beginning before paclitaxel (20 mg/kg single dose, i.p.) and continuing at intervals of 3 or 4 days. Blood samples were collected 3, 7, and 14 days (n=8 per cohort per time point) after paclitaxel. At 14 days, ActRIIA-mFc treatment increased hematocrit level progressively as a function of dose number (FIG. 16). Thus, ActRIIA-mFc can stimulate erythropoiesis sufficiently to attenuate or prevent chemotherapy-induced anemia.

EXAMPLE 9

Effect of ActRIIA-mFc on Anemia in a Mouse Model of Chronic Kidney Disease

Applicants investigated the effect of ActRIIA-mFc on nephrectomy-induced anemia in mice as a model of chronic kidney disease. In the first of two studies, female C57BL/6 mice underwent a partial surgical nephrectomy, with removal of approximately five-sixths of total kidney volume, to reduce production of erythropoietin. Mice were given a 4-week recovery period with a high-fat diet to further promote renal deficiency and were then treated twice-weekly with ActRIIA-mFc (10 mg/kg, s.c.) or vehicle (PBS) for a total of 8 weeks. Blood samples were collected before the onset of dosing, after 4 weeks of treatment, and after 8 weeks of treatment (n=8 per cohort per time point). Control mice exhibited a decline in hematocrit level over the 8-week treatment period, whereas ActRIIA-mFc treatment prevented the decline at 4 weeks and also produced a beneficial trend at 8 weeks (FIG. 17). Similar benefits of ActRIIA-mFc treatment over control were observed in a second study that differed mainly in the use of a longer recovery period (2 months) and a standard diet. Thus, ActRIIA-mFc can stimulate erythropoiesis sufficiently to prevent or attenuate anemia in a model of chronic kidney disease.

Taken together, these findings indicate that soluble ActRIIA-Fc fusion proteins can be used as antagonists of signaling by TGF-family ligands to increase circulating levels of red blood cells, and thereby, to treat hypoproliferative anemias resulting from chronic diseases such as cancer and renal disease, and potentially other inflammatory or infectious diseases as well. Note that effects of ACE-011 on anemia in human patients are typically robust compared to the more modest effects in rodents.

INCORPORATION BY REFERENCE

All publications and patents mentioned herein are hereby incorporated by reference in their entirety as if each individual publication or patent was specifically and individually indicated to be incorporated by reference.

While specific embodiments of the subject matter have been discussed, the above specification is illustrative and not restrictive. Many variations will become apparent to those skilled in the art upon review of this specification and the claims below. The full scope of the invention should be determined by reference to the claims, along with their full scope of equivalents, and the specification, along with such variations.

We claim:

1. A method for treating anemia in a patient, the method comprising administering to a patient in need thereof an effective amount of an ActRIIa polypeptide selected from the group consisting of:
   a) a polypeptide comprising an amino acid sequence at least 95% identical to SEQ ID NO: 2;
   b) a polypeptide comprising an amino acid sequence at least 95% identical to SEQ ID NO: 3;
   c) a polypeptide comprising an amino acid sequence at least 95% identical to SEQ ID NO: 7;
   d) a polypeptide comprising an amino acid sequence at least 95% identical to SEQ ID NO: 12; and
   e) a polypeptide comprising an amino acid sequence that is encoded by a nucleic acid that hybridizes to the complement of SEQ ID NO:5 in the presence of 6.0 sodium/sodium citrate (SSC) at 45° C. followed by a wash in 2.0 SSC at 45° C., and
wherein the ActRIIa polypeptide binds to activin.

2. The method of claim 1, wherein the patient has a hypoproliferative anemia.

3. The method of claim 2, wherein the patient has a kidney disease.

4. The method of claim 2, wherein the patient has a cancer.

5. The method of claim 4, wherein the cancer is selected from the group consisting of: multiple myeloma and breast cancer.

6. The method of claim 2, wherein the patient is iron deficient.

7. The method of claim 2, wherein the patient has a disorder of the bone marrow.

8. The method of claim 1, wherein the patient has a microcytic anemia.

9. The method of claim 1, wherein the patient has been treated with a myelosuppressive therapy.

10. The method of claim 9, wherein the myelosuppressive therapy is selected from the group consisting of: radiation and chemotherapy.

11. The method of claim 9, wherein the myelosuppressive therapy is selected from the group consisting of: an alkylating agent, an anti-metabolite, a cytotoxic antibiotic, a kinase inhibitor, a mitotic inhibitor, and a topoisomerase inhibitor.

12. The method of claim 9, wherein the patient has been treated with taxane.

13. The method of claim 12, wherein the patient has anemia and bone loss.

14. The method of claim 1, wherein said polypeptide is a fusion protein including, in addition to an ActRIIa polypeptide domain, one or more polypeptide portions that enhance one or more of in vivo stability, in vivo half life, uptake/administration, tissue localization or distribution, formation of protein complexes, and/or purification.

15. The method of claim 14, wherein said fusion protein includes a polypeptide portion selected from the group consisting of: an immunoglobulin Fc domain and a serum albumin.

16. The method of claim 1, wherein said polypeptide includes one or more modified amino acid residues selected from: a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent.

17. The method of claim 15, wherein the fusion protein is an ActRIIa-Fc fusion protein comprising an amino acid sequence selected from the group consisting of:
   a) the amino acid sequence of SEQ ID NO: 3,
   b) the amino acid sequence of SEQ ID NO: 2,
   c) the amino acid sequence of SEQ ID NO: 7, and
   d) the amino acid sequence of SEQ ID NO:12.

18. The method of claim 1, wherein the polypeptide comprises an amino acid sequence at least 95% identical to SEQ ID NO: 7.

19. The method of claim 1, wherein the polypeptide comprises the amino acid sequence of SEQ ID NO: 7.

20. The method of to claim 1, wherein the patient has an acute renal disease or failure.

21. The method of to claim 1, wherein the patient has a chronic renal disease or failure.

22. The method of to claim 1, wherein the patient has a thalassemia.

23. The method of to claim 1, wherein the patient has sickle cell disease.

* * * * *

UNITED STATES PATENT AND TRADEMARK OFFICE
CERTIFICATE OF CORRECTION

Page 1 of 2

PATENT NO. : 8,895,016 B2
APPLICATION NO. : 12/459188
DATED : November 25, 2014
INVENTOR(S) : Sherman et al.

It is certified that error appears in the above-identified patent and that said Letters Patent is hereby corrected as shown below:

In the Claims:

At column 72, line 34, please replace claim 20:

"The method of to claim 1, wherein the patient has an acute renal disease or failure."

with

--The method of claim 1, wherein the patient has an acute renal disease or failure.--

At column 72, line 36, please replace claim 21:

"The method of to claim 1, wherein the patient has a chronic renal disease or failure"

with

--The method of claim 1, wherein the patient has a chronic renal disease or failure.--

At column 72, line 38, please replace claim 22:

"The method of to claim 1, wherein the patient has a thalassemia."

with

--The method of claim 1, wherein the patient has a thalassemia.--

Signed and Sealed this
Twelfth Day of May, 2015

Michelle K. Lee
*Director of the United States Patent and Trademark Office*

CERTIFICATE OF CORRECTION (continued)
U.S. Pat. No. 8,895,016 B2

At column 72, line 40, please replace claim 23:

"The method of to claim 1, wherein the patient has sickle cell disease."

with

--The method of claim 1, wherein the patient has sickle cell disease.--

SEQUENCE LISTING

```
<160> NUMBER OF SEQ ID NOS: 25

<210> SEQ ID NO 1
<211> LENGTH: 513
<212> TYPE: PRT
<213> ORGANISM: Homo sapiens

<400> SEQUENCE: 1

Met Gly Ala Ala Ala Lys Leu Ala Phe Ala Val Phe Leu Ile Ser Cys
1               5                   10                  15

Ser Ser Gly Ala Ile Leu Gly Arg Ser Glu Thr Gln Glu Cys Leu Phe
            20                  25                  30

Phe Asn Ala Asn Trp Glu Lys Asp Arg Thr Asn Gln Thr Gly Val Glu
        35                  40                  45

Pro Cys Tyr Gly Asp Lys Asp Lys Arg Arg His Cys Phe Ala Thr Trp
    50                  55                  60

Lys Asn Ile Ser Gly Ser Ile Glu Ile Val Lys Gln Gly Cys Trp Leu
65                  70                  75                  80

Asp Asp Ile Asn Cys Tyr Asp Arg Thr Asp Cys Val Glu Lys Lys Asp
                85                  90                  95

Ser Pro Glu Val Tyr Phe Cys Cys Cys Glu Gly Asn Met Cys Asn Glu
            100                 105                 110

Lys Phe Ser Tyr Phe Pro Glu Met Glu Val Thr Gln Pro Thr Ser Asn
        115                 120                 125

Pro Val Thr Pro Lys Pro Pro Tyr Tyr Asn Ile Leu Leu Tyr Ser Leu
    130                 135                 140

Val Pro Leu Met Leu Ile Ala Gly Ile Val Ile Cys Ala Phe Trp Val
145                 150                 155                 160

Tyr Arg His His Lys Met Ala Tyr Pro Pro Val Leu Val Pro Thr Gln
                165                 170                 175

Asp Pro Gly Pro Pro Pro Ser Pro Leu Leu Gly Leu Lys Pro Leu
            180                 185                 190

Gln Leu Leu Glu Val Lys Ala Arg Gly Arg Phe Gly Cys Val Trp Lys
        195                 200                 205

Ala Gln Leu Leu Asn Glu Tyr Val Ala Val Lys Ile Phe Pro Ile Gln
    210                 215                 220

Asp Lys Gln Ser Trp Gln Asn Glu Tyr Glu Val Tyr Ser Leu Pro Gly
225                 230                 235                 240

Met Lys His Glu Asn Ile Leu Gln Phe Ile Gly Ala Glu Lys Arg Gly
                245                 250                 255

Thr Ser Val Asp Val Asp Leu Trp Leu Ile Thr Ala Phe His Glu Lys
            260                 265                 270

Gly Ser Leu Ser Asp Phe Leu Lys Ala Asn Val Val Ser Trp Asn Glu
        275                 280                 285

Leu Cys His Ile Ala Glu Thr Met Ala Arg Gly Leu Ala Tyr Leu His
    290                 295                 300

Glu Asp Ile Pro Gly Leu Lys Asp Gly His Lys Pro Ala Ile Ser His
305                 310                 315                 320

Arg Asp Ile Lys Ser Lys Asn Val Leu Leu Lys Asn Asn Leu Thr Ala
                325                 330                 335
```

```
Cys Ile Ala Asp Phe Gly Leu Ala Leu Lys Phe Glu Ala Gly Lys Ser
        340                 345                 350

Ala Gly Asp Thr His Gly Gln Val Gly Thr Arg Arg Tyr Met Ala Pro
        355                 360                 365

Glu Val Leu Glu Gly Ala Ile Asn Phe Gln Arg Asp Ala Phe Leu Arg
370                 375                 380

Ile Asp Met Tyr Ala Met Gly Leu Val Leu Trp Glu Leu Ala Ser Arg
385                 390                 395                 400

Cys Thr Ala Ala Asp Gly Pro Val Asp Glu Tyr Met Leu Pro Phe Glu
                405                 410                 415

Glu Glu Ile Gly Gln His Pro Ser Leu Glu Asp Met Gln Glu Val Val
                420                 425                 430

Val His Lys Lys Lys Arg Pro Val Leu Arg Asp Tyr Trp Gln Lys His
        435                 440                 445

Ala Gly Met Ala Met Leu Cys Glu Thr Ile Glu Glu Cys Trp Asp His
        450                 455                 460

Asp Ala Glu Ala Arg Leu Ser Ala Gly Cys Val Gly Glu Arg Ile Thr
465                 470                 475                 480

Gln Met Gln Arg Leu Thr Asn Ile Ile Thr Thr Glu Asp Ile Val Thr
                485                 490                 495

Val Val Thr Met Val Thr Asn Val Asp Phe Pro Pro Lys Glu Ser Ser
                500                 505                 510

Leu

<210> SEQ ID NO 2
<211> LENGTH: 115
<212> TYPE: PRT
<213> ORGANISM: Homo sapiens

<400> SEQUENCE: 2

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro
        115

<210> SEQ ID NO 3
<211> LENGTH: 100
<212> TYPE: PRT
<213> ORGANISM: Homo sapiens

<400> SEQUENCE: 3

Ile Leu Gly Arg Ser Glu Thr Gln Glu Cys Leu Phe Phe Asn Ala Asn
1               5                   10                  15
```

```
Trp Glu Lys Asp Arg Thr Asn Gln Thr Gly Val Glu Pro Cys Tyr Gly
             20                  25                  30

Asp Lys Asp Lys Arg Arg His Cys Phe Ala Thr Trp Lys Asn Ile Ser
         35                  40                  45

Gly Ser Ile Glu Ile Val Lys Gln Gly Cys Trp Leu Asp Asp Ile Asn
     50                  55                  60

Cys Tyr Asp Arg Thr Asp Cys Val Glu Lys Lys Asp Ser Pro Glu Val
 65                  70                  75                  80

Tyr Phe Cys Cys Cys Glu Gly Asn Met Cys Asn Glu Lys Phe Ser Tyr
                 85                  90                  95

Phe Pro Glu Met
            100

<210> SEQ ID NO 4
<211> LENGTH: 1542
<212> TYPE: DNA
<213> ORGANISM: Homo sapiens

<400> SEQUENCE: 4
```

| | | | | | |
|---|---|---|---|---|---|
| atgggagctg | ctgcaaagtt | ggcgtttgcc | gtctttctta | tctcctgttc | ttcaggtgct | 60 |
| atacttggta | gatcagaaac | tcaggagtgt | ctttctttta | atgctaattg | ggaaaaagac | 120 |
| agaaccaatc | aaactggtgt | tgaaccgtgt | tatggtgaca | agataaacg | gcggcattgt | 180 |
| tttgctacct | ggaagaatat | ttctggttcc | attgaaatag | tgaaacaagg | ttgttggctg | 240 |
| gatgatatca | actgctatga | caggactgat | tgtgtagaaa | aaaagacag | ccctgaagta | 300 |
| tattttgtt | gctgtgaggg | caatatgtgt | aatgaaaagt | tttcttattt | tccagagatg | 360 |
| gaagtcacac | agcccacttc | aaatccagtt | acacctaagc | caccctatta | caacatcctg | 420 |
| ctctattcct | tggtgccact | tatgttaatt | gcggggattg | tcatttgtgc | attttgggtg | 480 |
| tacaggcatc | acaagatggc | ctaccctcct | gtacttgttc | caactcaaga | cccaggacca | 540 |
| cccccaccttt | ctccattact | agggttgaaa | ccactgcagt | tattagaagt | gaaagcaagg | 600 |
| ggaagatttg | gttgtgtctg | gaaagcccag | ttgcttaacg | aatatgtggc | tgtcaaaata | 660 |
| tttccaatac | aggacaaaca | gtcatggcaa | aatgaatacg | aagtctacag | tttgcctgga | 720 |
| atgaagcatg | agaacatatt | acagttcatt | ggtgcagaaa | aacgaggcac | cagtgttgat | 780 |
| gtggatcttt | ggctgatcac | agcatttcat | gaaaagggtt | cactatcaga | ctttcttaag | 840 |
| gctaatgtgg | tctcttggaa | tgaactgtgt | catattgcag | aaaccatggc | tagaggattg | 900 |
| gcatatttac | atgaggatat | acctggccta | aaagatggcc | acaaacctgc | catatctcac | 960 |
| agggacatca | aaagtaaaaa | tgtgctgttg | aaaaacaacc | tgacagcttg | cattgctgac | 1020 |
| tttgggttgg | ccttaaaatt | tgaggctggc | aagtctgcag | gcgatacca | tggacaggtt | 1080 |
| ggtacccgga | ggtacatggc | tccagaggta | ttagagggtg | ctataaactt | ccaaagggat | 1140 |
| gcattttga | ggatagatat | gtatgccatg | ggattagtcc | tatgggaact | ggcttctcgc | 1200 |
| tgtactgctg | cagatggacc | tgtagatgaa | tacatgttgc | catttgagga | ggaaattggc | 1260 |
| cagcatccat | ctcttgaaga | catgcaggaa | gttgttgtgc | ataaaaaaaa | gaggcctgtt | 1320 |
| ttaagagatt | attggcagaa | acatgctgga | atggcaatgc | tctgtgaaac | cattgaagaa | 1380 |
| tgttgggatc | acgacgcaga | agccaggtta | tcagctggat | gtgtaggtga | agaattacc | 1440 |
| cagatgcaga | gactaacaaa | tattattacc | acagaggaca | ttgtaacagt | ggtcacaatg | 1500 |
| gtgacaaatg | ttgactttcc | tcccaaagaa | tctagtctat | ga | | 1542 |

<210> SEQ ID NO 5
<211> LENGTH: 345
<212> TYPE: DNA
<213> ORGANISM: Homo sapiens

<400> SEQUENCE: 5

```
atacttggta gatcagaaac tcaggagtgt cttttcttta atgctaattg ggaaaaagac    60
agaaccaatc aaactggtgt tgaaccgtgt tatggtgaca agataaacg gcggcattgt   120
tttgctacct ggaagaatat ttctggttcc attgaaatag tgaaacaagg ttgttggctg   180
gatgatatca actgctatga caggactgat tgtgtagaaa aaaagacag ccctgaagta   240
tattttgtt gctgtgaggg caatatgtgt aatgaaaagt tttcttattt tccagagatg   300
gaagtcacac agcccacttc aaatccagtt acacctaagc caccc                   345
```

<210> SEQ ID NO 6
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (43)..(43)
<223> OTHER INFORMATION: Asp or Ala
<220> FEATURE:
<221> NAME/KEY: MOD_RES
<222> LOCATION: (100)..(100)
<223> OTHER INFORMATION: Lys or Ala
<220> FEATURE:
<221> NAME/KEY: MOD_RES
<222> LOCATION: (212)..(212)
<223> OTHER INFORMATION: Asn or Ala

<400> SEQUENCE: 6

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Xaa Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
                85                  90                  95

Tyr Lys Cys Xaa Val Ser Asn Lys Ala Leu Pro Val Pro Ile Glu Lys
            100                 105                 110

Thr Ile Ser Lys Ala Lys Gly Gln Pro Arg Glu Pro Gln Val Tyr Thr
        115                 120                 125

Leu Pro Pro Ser Arg Glu Glu Met Thr Lys Asn Gln Val Ser Leu Thr
    130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Pro Phe Phe Leu Tyr Ser Lys Leu Thr Val Asp Lys
            180                 185                 190

Ser Arg Trp Gln Gln Gly Asn Val Phe Ser Cys Ser Val Met His Glu
```

```
               195                 200                 205
Ala Leu His Xaa His Tyr Thr Gln Lys Ser Leu Ser Leu Ser Pro Gly
    210                 215                 220

Lys
225

<210> SEQ ID NO 7
<211> LENGTH: 344
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr Gly Gly Gly Thr His Thr Cys Pro Pro Cys Pro Ala
        115                 120                 125

Pro Glu Leu Leu Gly Gly Pro Ser Val Phe Leu Phe Pro Pro Lys Pro
    130                 135                 140

Lys Asp Thr Leu Met Ile Ser Arg Thr Pro Glu Val Thr Cys Val Val
145                 150                 155                 160

Val Asp Val Ser His Glu Asp Pro Glu Val Lys Phe Asn Trp Tyr Val
                165                 170                 175

Asp Gly Val Glu Val His Asn Ala Lys Thr Lys Pro Arg Glu Glu Gln
            180                 185                 190

Tyr Asn Ser Thr Tyr Arg Val Val Ser Val Leu Thr Val Leu His Gln
        195                 200                 205

Asp Trp Leu Asn Gly Lys Glu Tyr Lys Cys Lys Val Ser Asn Lys Ala
    210                 215                 220

Leu Pro Val Pro Ile Glu Lys Thr Ile Ser Lys Ala Lys Gly Gln Pro
225                 230                 235                 240

Arg Glu Pro Gln Val Tyr Thr Leu Pro Pro Ser Arg Glu Glu Met Thr
                245                 250                 255

Lys Asn Gln Val Ser Leu Thr Cys Leu Val Lys Gly Phe Tyr Pro Ser
            260                 265                 270

Asp Ile Ala Val Glu Trp Glu Ser Asn Gly Gln Pro Glu Asn Asn Tyr
        275                 280                 285

Lys Thr Thr Pro Pro Val Leu Asp Ser Asp Gly Ser Phe Phe Leu Tyr
    290                 295                 300

Ser Lys Leu Thr Val Asp Lys Ser Arg Trp Gln Gln Gly Asn Val Phe
305                 310                 315                 320
```

```
Ser Cys Ser Val Met His Glu Ala Leu His Asn His Tyr Thr Gln Lys
            325                 330                 335

Ser Leu Ser Leu Ser Pro Gly Lys
            340

<210> SEQ ID NO 8
<211> LENGTH: 21
<212> TYPE: PRT
<213> ORGANISM: Apis sp.

<400> SEQUENCE: 8

Met Lys Phe Leu Val Asn Val Ala Leu Val Phe Met Val Val Tyr Ile
1               5                   10                  15

Ser Tyr Ile Tyr Ala
            20

<210> SEQ ID NO 9
<211> LENGTH: 22
<212> TYPE: PRT
<213> ORGANISM: Unknown
<220> FEATURE:
<223> OTHER INFORMATION: Description of Unknown: Tissue Plasminogen
      Activator leader sequence

<400> SEQUENCE: 9

Met Asp Ala Met Lys Arg Gly Leu Cys Cys Val Leu Leu Leu Cys Gly
1               5                   10                  15

Ala Val Phe Val Ser Pro
            20

<210> SEQ ID NO 10
<211> LENGTH: 20
<212> TYPE: PRT
<213> ORGANISM: Unknown
<220> FEATURE:
<223> OTHER INFORMATION: Description of Unknown: Native leader sequence

<400> SEQUENCE: 10

Met Gly Ala Ala Ala Lys Leu Ala Phe Ala Val Phe Leu Ile Ser Cys
1               5                   10                  15

Ser Ser Gly Ala
            20

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Ile Leu Gly Arg Ser Glu Thr Gln Glu
1               5

<210> SEQ ID NO 12
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Ile Leu Gly Arg Ser Glu Thr Gln Glu Cys Leu Phe Phe Asn Ala Asn
```

```
                1               5                  10                 15
            Trp Glu Lys Asp Arg Thr Asn Gln Thr Gly Val Glu Pro Cys Tyr Gly
                            20                  25                  30

Asp Lys Asp Lys Arg Arg His Cys Phe Ala Thr Trp Lys Asn Ile Ser
                        35                  40                  45

Gly Ser Ile Glu Ile Val Lys Gln Gly Cys Trp Leu Asp Asp Ile Asn
                    50                  55                  60

Cys Tyr Asp Arg Thr Asp Cys Val Glu Lys Lys Asp Ser Pro Glu Val
            65                  70                  75                  80

Tyr Phe Cys Cys Cys Glu Gly Asn Met Cys Asn Glu Lys Phe Ser Tyr
                                85                  90                  95

Phe Pro Glu Met Thr Gly Gly Thr His Thr Cys Pro Pro Cys Pro
                            100                 105                 110

Ala Pro Glu Leu Leu Gly Gly Pro Ser Val Phe Leu Phe Pro Pro Lys
                        115                 120                 125

Pro Lys Asp Thr Leu Met Ile Ser Arg Thr Pro Glu Val Thr Cys Val
                    130                 135                 140

Val Val Asp Val Ser His Glu Asp Pro Glu Val Lys Phe Asn Trp Tyr
            145                 150                 155                 160

Val Asp Gly Val Glu Val His Asn Ala Lys Thr Lys Pro Arg Glu Glu
                                165                 170                 175

Gln Tyr Asn Ser Thr Tyr Arg Val Val Ser Val Leu Thr Val Leu His
                            180                 185                 190

Gln Asp Trp Leu Asn Gly Lys Glu Tyr Lys Cys Lys Val Ser Asn Lys
                        195                 200                 205

Ala Leu Pro Val Pro Ile Glu Lys Thr Ile Ser Lys Ala Lys Gly Gln
                    210                 215                 220

Pro Arg Glu Pro Gln Val Tyr Thr Leu Pro Pro Ser Arg Glu Glu Met
            225                 230                 235                 240

Thr Lys Asn Gln Val Ser Leu Thr Cys Leu Val Lys Gly Phe Tyr Pro
                                245                 250                 255

Ser Asp Ile Ala Val Glu Trp Glu Ser Asn Gly Gln Pro Glu Asn Asn
                            260                 265                 270

Tyr Lys Thr Thr Pro Pro Val Leu Asp Ser Asp Gly Ser Phe Phe Leu
                        275                 280                 285

Tyr Ser Lys Leu Thr Val Asp Lys Ser Arg Trp Gln Gln Gly Asn Val
                    290                 295                 300

Phe Ser Cys Ser Val Met His Glu Ala Leu His Asn His Tyr Thr Gln
            305                 310                 315                 320

Lys Ser Leu Ser Leu Ser Pro Gly Lys
                                325

<210> SEQ ID NO 13
<211> LENGTH: 369
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Met Asp Ala Met Lys Arg Gly Leu Cys Cys Val Leu Leu Leu Cys Gly
1               5                  10                  15

Ala Val Phe Val Ser Pro Gly Ala Ala Ile Leu Gly Arg Ser Glu Thr
            20                  25                  30
```

| | | | | | | | | | | | | |
|---|---|---|---|---|---|---|---|---|---|---|---|---|
|Gln|Glu|Cys|Leu|Phe|Phe|Asn|Ala|Asn|Trp|Lys|Asp|Arg|Thr|Asn|
| | |35| | | |40| | | |45| | | |

Gln Thr Gly Val Glu Pro Cys Tyr Gly Asp Lys Asp Lys Arg Arg His
       50                  55                  60

Cys Phe Ala Thr Trp Lys Asn Ile Ser Gly Ser Ile Glu Ile Val Lys
 65                  70                  75                  80

Gln Gly Cys Trp Leu Asp Asp Ile Asn Cys Tyr Asp Arg Thr Asp Cys
                 85                  90                  95

Val Glu Lys Lys Asp Ser Pro Glu Val Tyr Phe Cys Cys Cys Glu Gly
            100                 105                 110

Asn Met Cys Asn Glu Lys Phe Ser Tyr Phe Pro Glu Met Glu Val Thr
            115                 120                 125

Gln Pro Thr Ser Asn Pro Val Thr Pro Lys Pro Thr Gly Gly Gly
        130                 135                 140

Thr His Thr Cys Pro Pro Cys Pro Ala Pro Glu Leu Leu Gly Gly Pro
145                 150                 155                 160

Ser Val Phe Leu Phe Pro Pro Lys Pro Lys Asp Thr Leu Met Ile Ser
                165                 170                 175

Arg Thr Pro Glu Val Thr Cys Val Val Val Asp Val Ser His Glu Asp
            180                 185                 190

Pro Glu Val Lys Phe Asn Trp Tyr Val Asp Gly Val Glu Val His Asn
            195                 200                 205

Ala Lys Thr Lys Pro Arg Glu Glu Gln Tyr Asn Ser Thr Tyr Arg Val
        210                 215                 220

Val Ser Val Leu Thr Val Leu His Gln Asp Trp Leu Asn Gly Lys Glu
225                 230                 235                 240

Tyr Lys Cys Lys Val Ser Asn Lys Ala Leu Pro Val Pro Ile Glu Lys
                245                 250                 255

Thr Ile Ser Lys Ala Lys Gly Gln Pro Arg Glu Pro Gln Val Tyr Thr
            260                 265                 270

Leu Pro Pro Ser Arg Glu Glu Met Thr Lys Asn Gln Val Ser Leu Thr
        275                 280                 285

Cys Leu Val Lys Gly Phe Tyr Pro Ser Asp Ile Ala Val Glu Trp Glu
290                 295                 300

Ser Asn Gly Gln Pro Glu Asn Asn Tyr Lys Thr Thr Pro Pro Val Leu
305                 310                 315                 320

Asp Ser Asp Gly Ser Phe Phe Leu Tyr Ser Lys Leu Thr Val Asp Lys
                325                 330                 335

Ser Arg Trp Gln Gln Gly Asn Val Phe Ser Cys Ser Val Met His Glu
            340                 345                 350

Ala Leu His Asn His Tyr Thr Gln Lys Ser Leu Ser Leu Ser Pro Gly
            355                 360                 365

Lys

<210> SEQ ID NO 14
<211> LENGTH: 1114
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14
atggatgcaa tgaagagagg gctctgctgt gtgctgctgc tgtgtggagc agtcttcgtt     60
tcgcccggcg ccgctatact tggtagatca gaaactcagg agtgtctttt tttaatgcta    120

```
attgggaaaa agacagaacc aatcaaactg gtgttgaacc gtgttatggt gacaaagata      180
aacggcggca ttgttttgct acctggaaga atatttctgg ttccattgaa tagtgaaaca      240
aggttgttgg ctggatgata tcaactgcta tgacaggact gattgtgtag aaaaaaaaga      300 cagcccctgaa gtatatttct gttgctgtga gggcaatatg tgtaatgaaa agttttctta     360
ttttccggag atggaagtca cacagcccac ttcaaatcca gttacaccta agccacccac      420
cggtggtgga actcacacat gcccaccgtg cccagcacct gaactcctgg ggggaccgtc      480
agtcttcctc ttccccccaa aacccaagga caccctcatg atctcccgga cccctgaggt      540
cacatgcgtg gtggtggacg tgagccacga agaccctgag gtcaagttca actggtacgt      600
ggacggcgtg gaggtgcata atgccaagac aaagccgcgg gaggagcagt acaacagcac      660
gtaccgtgtg gtcagcgtcc tcaccgtcct gcaccaggac tggctgaatg caaggagta      720 caagtgcaag gtctccaaca aagccctccc agtccccatc gagaaaacca tctccaaagc      780
caaagggcag ccccgagaac cacaggtgta caccctgccc ccatcccggg aggagatgac      840
caagaaccag gtcagcctga cctgcctggt caaaggcttc tatcccagcg acatcgccgt      900
ggagtgggag agcaatgggc agccggagaa caactacaag accacgcctc ccgtgctgga      960
ctccgacggc tccttcttcc tctatagcaa gctcaccgtg gacaagagca ggtggcagca     1020
ggggaacgtc ttctcatgct ccgtgatgca tgaggctctg cacaaccact acacgcagaa     1080
gagcctctcc ctgtctccgg gtaaatgaga attc                                 1114
```

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Gly Gly Gly Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Gly Gly Gly Gly
1               5

<210> SEQ ID NO 17
<211> LENGTH: 343
<212> TYPE: PRT
<213> ORGANISM: Homo sapiens

<400> SEQUENCE: 17

Met Val Arg Ala Arg His Gln Pro Gly Gly Leu Cys Leu Leu Leu
1               5                   10                  15

Leu Leu Cys Gln Phe Met Glu Asp Arg Ser Ala Gln Ala Gly Asn Cys
            20                  25                  30

Trp Leu Arg Gln Ala Lys Asn Gly Arg Cys Gln Val Leu Tyr Lys Thr
        35                  40                  45

```
Glu Leu Ser Lys Glu Glu Cys Cys Ser Thr Gly Arg Leu Ser Thr Ser
        50                  55                  60

Trp Thr Glu Glu Asp Val Asn Asp Asn Thr Leu Phe Lys Trp Met Ile
 65                  70                  75                  80

Phe Asn Gly Gly Ala Pro Asn Cys Ile Pro Cys Lys Glu Thr Cys Glu
                85                  90                  95

Asn Val Asp Cys Gly Pro Gly Lys Lys Cys Arg Met Asn Lys Lys Asn
                100                 105                 110

Lys Pro Arg Cys Val Cys Ala Pro Asp Cys Ser Asn Ile Thr Trp Lys
            115                 120                 125

Gly Pro Val Cys Gly Leu Asp Gly Lys Thr Tyr Arg Asn Glu Cys Ala
130                 135                 140

Leu Leu Lys Ala Arg Cys Lys Glu Gln Pro Glu Leu Glu Val Gln Tyr
145                 150                 155                 160

Gln Gly Arg Cys Lys Lys Thr Cys Arg Asp Val Phe Cys Pro Gly Ser
                165                 170                 175

Ser Thr Cys Val Val Asp Gln Thr Asn Asn Ala Tyr Cys Val Thr Cys
            180                 185                 190

Asn Arg Ile Cys Pro Glu Pro Ala Ser Ser Glu Gln Tyr Leu Cys Gly
            195                 200                 205

Asn Asp Gly Val Thr Tyr Ser Ser Ala Cys His Leu Arg Lys Ala Thr
210                 215                 220

Cys Leu Leu Gly Arg Ser Ile Gly Leu Ala Tyr Glu Gly Lys Cys Ile
225                 230                 235                 240

Lys Ala Lys Ser Cys Glu Asp Ile Gln Cys Thr Gly Gly Lys Lys Cys
                245                 250                 255

Leu Trp Asp Phe Lys Val Gly Arg Gly Arg Cys Ser Leu Cys Asp Glu
            260                 265                 270

Leu Cys Pro Asp Ser Lys Ser Asp Glu Pro Val Cys Ala Ser Asp Asn
            275                 280                 285

Ala Thr Tyr Ala Ser Glu Cys Ala Met Lys Glu Ala Ala Cys Ser Ser
290                 295                 300

Gly Val Leu Leu Glu Val Lys His Gly Ser Cys Asn Ser Ile Ser Glu
305                 310                 315                 320

Asp Thr Glu Glu Glu Glu Asp Glu Asp Gln Asp Tyr Ser Phe Pro
            325                 330                 335

Ile Ser Ser Ile Leu Glu Trp
            340

<210> SEQ ID NO 18
<211> LENGTH: 317
<212> TYPE: PRT
<213> ORGANISM: Homo sapiens

<400> SEQUENCE: 18

Met Val Arg Ala Arg His Gln Pro Gly Gly Leu Cys Leu Leu Leu Leu
 1               5                   10                  15

Leu Leu Cys Gln Phe Met Glu Asp Arg Ser Ala Gln Ala Gly Asn Cys
                20                  25                  30

Trp Leu Arg Gln Ala Lys Asn Gly Arg Cys Gln Val Leu Tyr Lys Thr
            35                  40                  45

Glu Leu Ser Lys Glu Glu Cys Cys Ser Thr Gly Arg Leu Ser Thr Ser
        50                  55                  60

Trp Thr Glu Glu Asp Val Asn Asp Asn Thr Leu Phe Lys Trp Met Ile
```

```
                65                  70                  75                  80
            Phe Asn Gly Gly Ala Pro Asn Cys Ile Pro Cys Lys Glu Thr Cys Glu
                                85                  90                  95

Asn Val Asp Cys Gly Pro Gly Lys Lys Cys Arg Met Asn Lys Lys Asn
                            100                 105                 110

Lys Pro Arg Cys Val Cys Ala Pro Asp Cys Ser Asn Ile Thr Trp Lys
                        115                 120                 125

Gly Pro Val Cys Gly Leu Asp Gly Lys Thr Tyr Arg Asn Glu Cys Ala
                    130                 135                 140

Leu Leu Lys Ala Arg Cys Lys Glu Gln Pro Glu Leu Glu Val Gln Tyr
            145                 150                 155                 160

Gln Gly Arg Cys Lys Lys Thr Cys Arg Asp Val Phe Cys Pro Gly Ser
                                165                 170                 175

Ser Thr Cys Val Val Asp Gln Thr Asn Asn Ala Tyr Cys Val Thr Cys
                            180                 185                 190

Asn Arg Ile Cys Pro Glu Pro Ala Ser Ser Glu Gln Tyr Leu Cys Gly
                        195                 200                 205

Asn Asp Gly Val Thr Tyr Ser Ser Ala Cys His Leu Arg Lys Ala Thr
                    210                 215                 220

Cys Leu Leu Gly Arg Ser Ile Gly Leu Ala Tyr Glu Gly Lys Cys Ile
            225                 230                 235                 240

Lys Ala Lys Ser Cys Glu Asp Ile Gln Cys Thr Gly Gly Lys Lys Cys
                                245                 250                 255

Leu Trp Asp Phe Lys Val Gly Arg Gly Arg Cys Ser Leu Cys Asp Glu
                            260                 265                 270

Leu Cys Pro Asp Ser Lys Ser Asp Glu Pro Val Cys Ala Ser Asp Asn
                        275                 280                 285

Ala Thr Tyr Ala Ser Glu Cys Ala Met Lys Glu Ala Ala Cys Ser Ser
                    290                 295                 300

Gly Val Leu Leu Glu Val Lys His Ser Gly Ser Cys Asn
            305                 310                 315

<210> SEQ ID NO 19
<211> LENGTH: 63
<212> TYPE: PRT
<213> ORGANISM: Homo sapiens

<400> SEQUENCE: 19

Gly Asn Cys Trp Leu Arg Gln Ala Lys Asn Gly Arg Cys Gln Val Leu
1               5                   10                  15

Tyr Lys Thr Glu Leu Ser Lys Glu Glu Cys Cys Ser Thr Gly Arg Leu
                20                  25                  30

Ser Thr Ser Trp Thr Glu Glu Asp Val Asn Asp Asn Thr Leu Phe Lys
            35                  40                  45

Trp Met Ile Phe Asn Gly Gly Ala Pro Asn Cys Ile Pro Cys Lys
        50                  55                  60

<210> SEQ ID NO 20
<211> LENGTH: 25
<212> TYPE: PRT
<213> ORGANISM: Homo sapiens

<400> SEQUENCE: 20

Glu Thr Cys Glu Asn Val Asp Cys Gly Pro Gly Lys Lys Cys Arg Met
1               5                   10                  15

Asn Lys Lys Asn Lys Pro Arg Cys Val
                20                  25
```

<210> SEQ ID NO 21
<211> LENGTH: 26
<212> TYPE: PRT
<213> ORGANISM: Homo sapiens

<400> SEQUENCE: 21

Lys Thr Cys Arg Asp Val Phe Cys Pro Gly Ser Ser Thr Cys Val Val
1               5                   10                  15

Asp Gln Thr Asn Asn Ala Tyr Cys Val Thr
            20                  25

<210> SEQ ID NO 22
<211> LENGTH: 262
<212> TYPE: PRT
<213> ORGANISM: Homo sapiens

<400> SEQUENCE: 22

Met Arg Pro Gly Ala Pro Gly Pro Leu Trp Pro Leu Pro Trp Gly Ala
1               5                   10                  15

Leu Ala Trp Ala Val Gly Phe Val Ser Ser Met Gly Ser Gly Asn Pro
            20                  25                  30

Ala Pro Gly Gly Val Cys Trp Leu Gln Gln Gly Gln Glu Ala Thr Cys
        35                  40                  45

Ser Leu Val Leu Gln Thr Asp Val Thr Arg Ala Glu Cys Cys Ala Ser
    50                  55                  60

Gly Asn Ile Asp Thr Ala Trp Ser Asn Leu Thr His Pro Gly Asn Lys
65                  70                  75                  80

Ile Asn Leu Leu Gly Phe Leu Gly Leu Val His Cys Leu Pro Cys Lys
                85                  90                  95

Asp Ser Cys Asp Gly Val Glu Cys Gly Pro Gly Lys Ala Cys Arg Met
            100                 105                 110

Leu Gly Gly Arg Pro Arg Cys Glu Cys Ala Pro Asp Cys Ser Gly Leu
        115                 120                 125

Pro Ala Arg Leu Gln Val Cys Gly Ser Asp Gly Ala Thr Tyr Arg Asp
    130                 135                 140

Glu Cys Glu Leu Arg Ala Ala Arg Cys Arg Gly His Pro Asp Leu Ser
145                 150                 155                 160

Val Met Tyr Arg Gly Arg Cys Arg Lys Ser Cys Glu His Val Val Cys
                165                 170                 175

Pro Arg Pro Gln Ser Cys Val Val Asp Gln Thr Gly Ser Ala His Cys
            180                 185                 190

Val Val Cys Arg Ala Ala Pro Cys Val Pro Ser Ser Pro Gly Gln Glu
        195                 200                 205

Leu Cys Gly Asn Asn Asn Val Thr Tyr Ile Ser Ser Cys His Met Arg
    210                 215                 220

Gln Ala Thr Cys Phe Leu Gly Arg Ser Ile Gly Val Arg His Ala Gly
225                 230                 235                 240

Ser Cys Ala Gly Thr Pro Glu Glu Pro Pro Gly Gly Glu Ser Ala Glu
                245                 250                 255

Glu Glu Glu Asn Phe Val
            260

<210> SEQ ID NO 23
<211> LENGTH: 116
<212> TYPE: PRT

<213> ORGANISM: Homo sapiens

<400> SEQUENCE: 23

```
Ile Leu Gly Arg Ser Glu Thr Gln Glu Cys Leu Phe Phe Asn Ala Asn
1               5                   10                  15

Trp Glu Lys Asp Arg Thr Asn Gln Thr Gly Val Glu Pro Cys Tyr Gly
            20                  25                  30

Asp Lys Asp Lys Arg Arg His Cys Phe Ala Thr Trp Lys Asn Ile Ser
        35                  40                  45

Gly Ser Ile Glu Ile Val Lys Gln Gly Cys Trp Leu Asp Asp Ile Asn
    50                  55                  60

Cys Tyr Asp Arg Thr Asp Cys Val Glu Lys Lys Asp Ser Pro Glu Val
65                  70                  75                  80

Tyr Phe Cys Cys Cys Glu Gly Asn Met Cys Asn Glu Lys Phe Ser Tyr
                85                  90                  95

Phe Pro Glu Met Glu Val Thr Gln Pro Thr Ser Asn Pro Val Thr Pro
            100                 105                 110

Lys Pro Pro Thr
        115
```

<210> SEQ ID NO 24
<211> LENGTH: 115
<212> TYPE: PRT
<213> ORGANISM: Homo sapiens

<400> SEQUENCE: 24

```
Gly Arg Gly Glu Ala Glu Thr Arg Glu Cys Ile Tyr Tyr Asn Ala Asn
1               5                   10                  15

Trp Glu Leu Glu Arg Thr Asn Gln Ser Gly Leu Glu Arg Cys Glu Gly
            20                  25                  30

Glu Gln Asp Lys Arg Leu His Cys Tyr Ala Ser Trp Arg Asn Ser Ser
        35                  40                  45

Gly Thr Ile Glu Leu Val Lys Lys Gly Cys Trp Leu Asp Asp Phe Asn
    50                  55                  60

Cys Tyr Asp Arg Gln Glu Cys Val Ala Thr Glu Glu Asn Pro Gln Val
65                  70                  75                  80

Tyr Phe Cys Cys Cys Glu Gly Asn Phe Cys Asn Glu Arg Phe Thr His
                85                  90                  95

Leu Pro Glu Ala Gly Gly Pro Glu Val Thr Tyr Glu Pro Pro Pro Thr
            100                 105                 110

Ala Pro Thr
        115
```

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 25

```
His His His His His His
1               5
```